(12) United States Patent
Ban et al.

(10) Patent No.: US 12,427,192 B2
(45) Date of Patent: Sep. 30, 2025

(54) WATER SOLUBLE ADJUVANT AND COMPOSITION CONTAINING SAME

(71) Applicant: Sumitomo Pharma Co., Ltd., Osaka (JP)

(72) Inventors: Hitoshi Ban, Osaka (JP); Yosuke Takanashi, Osaka (JP); Masashi Goto, Osaka (JP); Natsuko Suginobe, Osaka (JP); Yusuke Imazaki, Osaka (JP); Yoshiko Iwata, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 1031 days.

(21) Appl. No.: 17/600,919

(22) PCT Filed: Apr. 3, 2020

(86) PCT No.: PCT/JP2020/015359
§ 371 (c)(1),
(2) Date: Oct. 1, 2021

(87) PCT Pub. No.: WO2020/204172
PCT Pub. Date: Oct. 8, 2020

(65) Prior Publication Data
US 2022/0211844 A1    Jul. 7, 2022

(30) Foreign Application Priority Data
Apr. 5, 2019   (JP) ................. 2019-072910

(51) Int. Cl.
*A61K 39/39*      (2006.01)
*A61K 39/00*      (2006.01)
(Continued)

(52) U.S. Cl.
CPC .......... *A61K 39/39* (2013.01); *A61K 39/0011* (2013.01); *A61K 39/001153* (2018.08);
(Continued)

(58) Field of Classification Search
CPC combination set(s) only.
See application file for complete search history.

(56) References Cited

U.S. PATENT DOCUMENTS

2009/0136572 A1    5/2009   Saito et al.
2018/0280499 A1   10/2018   Kimura et al.
(Continued)

FOREIGN PATENT DOCUMENTS

JP    2019-500360     1/2019
WO   WO 2006/078059   7/2006
(Continued)

OTHER PUBLICATIONS

Israeli E, Agmon-Levin N, Blank M, Shoenfeld Y. Adjuvants and autoimmunity. Lupus. Nov. 2009; 18(13):1217-25. doi: 10.1177/0961203309345724. PMID: 19880572. (Year: 2009).*

(Continued)

*Primary Examiner* — Jeffrey Stucker
*Assistant Examiner* — Laura Ann Essex
(74) *Attorney, Agent, or Firm* — Fish & Richardson P.C.

(57) ABSTRACT

The present invention relates to a compound useful as a vaccine adjuvant for cancer vaccine, a preparation process thereof, a pharmaceutical composition comprising the compound, and use of the compound as a vaccine adjuvant for cancer vaccine.

39 Claims, 15 Drawing Sheets

Specification includes a Sequence Listing.

(51) Int. Cl.
  *A61P 35/00* (2006.01)
  *A61P 37/04* (2006.01)
  *C07D 239/49* (2006.01)
(52) U.S. Cl.
  CPC ............... *A61P 35/00* (2018.01); *A61P 37/04* (2018.01); *C07D 239/49* (2013.01); *A61K 2039/55566* (2013.01)

(56) References Cited

U.S. PATENT DOCUMENTS

| | | | |
|---|---|---|---|
| 2018/0362560 | A1 | 12/2018 | Bazin-Lee et al. |
| 2019/0375772 | A1 | 12/2019 | Bazin-Lee et al. |
| 2020/0121600 | A1 | 4/2020 | Fukushima |
| 2021/0277038 | A1 | 9/2021 | Bazin-Lee et al. |

FOREIGN PATENT DOCUMENTS

| | | |
|---|---|---|
| WO | WO 2009/067081 | 5/2009 |
| WO | WO 2012/031140 | 3/2012 |
| WO | WO 2017/061532 | 4/2017 |
| WO | WO 2018/046460 | 3/2018 |
| WO | WO 2018/181420 | 10/2018 |

OTHER PUBLICATIONS

Chen X, Venkatachalapathy M, Dehmelt L, Wu YW. Multidirectional Activity Control of Cellular Processes by a Versatile Chemo-optogenetic Approach. Angew Chem Int Ed Engl. Sep. 10, 2018;57(37):11993-11997. doi: 10.1002/anie.201806976. Epub Aug. 17, 2018. PMID: 30048030; PMCID: PMC6175152. (Year: 2018).*

Sachin Bhagchandani, Johnson JA, Irvine DJ. Evolution of Toll-like receptor 7/8 agonist therapeutics and their delivery approaches: From antiviral formulations to vaccine adjuvants. Adv Drug Deliv Rev. Aug. 2021;175:113803. doi: 10.1016/j.addr.2021.05.013. Epub May 29, 2021. PMID: 34058283. (Year: 2021).*

Cortez et al., "Incorporation of Phosphonate into Benzonaphthyridine Toll-like Receptor 7 Agonists for Adsorption to Aluminum Hydroxide," J. Med. Chem., Jun. 2016, 59(12), 5868-5878, 11 pages.

Dubensky Jr. et al., "Adjuvants for Cancer Vaccines," Seminars in Immunology, Jun. 2010, 22(3): 155-161.

International Preliminary Report on Patentability in International Appln. No. PCT/JP2020/015359, dated Sep. 28, 2021, 4 pages.

International Search Report in International Appln. No. PCT/JP2020/015359, mailed Jun. 23, 2020, 2 pages.

Khong et al., "Adjuvants for peptide-based cancer vaccines," Journal for Immuno Therapy of Cancer, Sep. 2016, 4:56, 11 pages.

Steinhagen et al., "TLR-based immune adjuvants," Vaccine, Apr. 2011, 29(17): 3341-3355.

Wu et al., "Rational design of small molecules as vaccine adjuvants," Sci Transl Med., Nov. 2014, 6(263): 263ra160, 1-12.

Extended European Search Report in European Appln. No. 20784003.4, dated Nov. 18, 2022, 8 pages.

Rampersaud et al., "Novel discrete PEG-based crosslinking reagents for conjugation of antibodies and proteins to biotin, fluorochromes, enzymes and gold that eliminate aggregation, improves solubility, reduces non-specific binding and enhances low level detection limits," Annual Meeting of the American-Society-For-Cell-Biology (ASCB), Dec. 3-7, 2011, Jan. 2011, 22:1 page.

Xin et al., "Conjugation of PEG-hexadecane markedly increases the immunogenicity of pneumococcal polysaccharide conjugate vaccine," Vaccine, 2017, 35(13):1698-1704.

Zalipsky, "Chemistry of polyethylene glycol conjugates with biologically active molecules," Advanced Drug Delivery Reviews, Sep. 1995, 16(2-3):157-182.

* cited by examiner

WATER SOLUBLE ADJUVANT AND COMPOSITION CONTAINING SAME

SEQUENCE LISTING

This application contains a Sequence Listing that has been submitted electronically as an ASCII text file named "38960-0028US1_SL_ST25.txt." The ASCII text file, created on Mar. 11, 2025, is 4,287 bytes in size. The material in the ASCII text file is hereby incorporated by reference in its entirety.

TECHNICAL FIELD

The present invention relates to a compound useful as vaccine adjuvant for vaccine (cancer vaccine or infection vaccine), a manufacturing process thereof, a pharmaceutical composition comprising the compound, and use of the compound as vaccine adjuvant for vaccine (cancer vaccine or infection vaccine).

BACKGROUND ART

In general, cancer vaccine therapy activates an immune cell specific to tumor by using protein or peptide obtained from tumor antigen to treat a cancer. Among the therapy, a therapy in which tumor antigen peptide is used as the antigen is referred to as cancer peptide vaccine therapy. In general, the therapy with only tumor antigen peptide brings on low immunogenicity. Thus, in order to induce cytotoxic T-lymphocyte (CTL) which is important for antitumor immunity, a vaccine adjuvant is used together. For example, W/O emulsion can easily retain an antigen peptide in its internal phase because it has aqueous phase in the internal phase. Thus, it has been reported that use of W/O emulsion as a vaccine adjuvant shows effective CTL induction (Patent Literature 1).

W/O emulsion to be used as vaccine adjuvant for tumor antigen peptide includes an emulsion composition for dilution (Patent Literature 1), as well as Incomplete Freund's Adjuvant (IFA) and Montanide™ (Non-Patent Literatures 1 and 2). In addition, Complete Freund's Adjuvant (CFA) which is prepared by adding inactivated Mycobacterium Tuberculosis to W/O emulsion is also known. However, CFA has not been allowed to be used in human due to its toxicity (Non-Patent Literature 2).

Conventionally, adjuvant compositions prepared by adding an inactivated bacterial body itself to an adjuvant like CFA had been used for enhancing the target activity, but recently vaccine adjuvants comprising a compound whose working mechanism is known have been developed. Among them, Toll like receptor 7 (TLR7) has been reported to activate Th1 cell to enhance cellular immunity which is needed for antitumor activity (Non-Patent Literature 3). With respect to TLR7, some small molecules have been known to act as a ligand, and imiquimod which has been on the market, as well as a compound having a pyrimidine structure have been reported to act as TLR7 agonist (Patent Literature 2).

There has been some trials to improve a TLR7 agonist to find a new compound having a physical property suitable for adjuvant. For example, it has been reported that a TLR7 agonist having a structure of conjugated phosphate group binds to insoluble metallic particle such as Alum adjuvant (Patent Literature 3, Non-patent Literatures 4 and 5).

PRIOR ART

Patent Reference

[Patent Literature 1] WO 2006/078059
[Patent Literature 2] WO2009/067081
[Patent Literature 3] WO2012/031140

Non-Patent Reference

[Non-Patent Literature 1] J Immunother Cancer. 2016 Sep. 20; 4: 56
[Non-Patent Literature 2] Semin Immunol. 2010 June; 22(3): 155-61.
[Non-Patent Literature 3] Vaccine. 2011 Apr. 12; 29(17): 3341-55.
[Non-Patent Literature 4] Sci Transl Med. 2014 Nov. 19; 6(263): 263ra160
[Non-Patent Literature 5] J. Med. Chem., 2016, 59 (12), pp 5868-5878

SUMMARY OF INVENTION

Technical Problem

The purpose of the present invention may be to provide a conjugated TLR7 agonist for enhancing adjuvant activity.

Solution to Problem

The present inventors have extensively studied to find a TLR7 agonist for enhancing adjuvant activity, and then have found that a TLR7 agonist to which water-solubility is added by conjugating a TLR7 agonist having a pyrimidine structure with polyethylene glycol (PEG) has an excellent adjuvant activity. Based upon the findings, the present invention has been achieved. According to the present invention, a pyrimidine derivative of the following formula (1) (hereinafter, also referred to as "the present compound") is provided.

The present invention is as described below.
(Item 1)
A compound of formula (1):

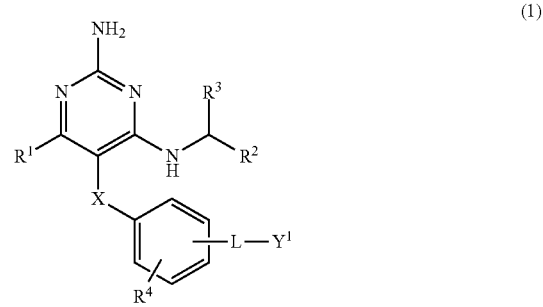

(1)

or a pharmaceutically acceptable salt thereof, wherein
X is methylene, oxygen atom, sulfur atom, SO, SO$_2$, or NR$^5$, wherein R$^5$ is hydrogen atom or C$_{1-6}$ alkyl,
R$^1$ is C$_{1-6}$ alkyl which may be substituted with 1-5 substituents selected independently from the group consisting of halogen, hydroxy, and C$_{1-6}$ alkoxy,
R$^2$ and R$^3$ are independently hydrogen atom or C$_{1-6}$ alkyl which may be substituted with 1-5 substituents selected independently from the group consisting of halogen, hydroxy, and C$_{1-6}$ alkoxy, R⁴ is hydrogen atom, halogen, hydroxy, $C_{1-6}$ alkyl (which may be substituted with 1-3 the same or different halogens), $C_{1-6}$ alkoxy (which may be substituted with 1-3 the same or different halogens) or cyano, L is a linker, and $Y^1$ is —$(CH_2CH_2O)_m$—$R^6$, wherein $R^6$ is hydrogen atom or $C_{1-6}$ alkyl, and m is an integer of 3-100.

(Item 2)

The compound of Item 1 or a pharmaceutically acceptable salt thereof, wherein X is methylene.

(Item 3)

The compound of Item 1 or 2 or a pharmaceutically acceptable salt thereof, wherein $R^1$ is $C_{1-3}$ alkyl which may be substituted with 1-3 the same or different halogens.

(Item 4)

The compound of Item 3 or a pharmaceutically acceptable salt thereof, wherein $R^1$ is methyl.

(Item 5)

The compound of any one of Items 1 to 4 or a pharmaceutically acceptable salt thereof, wherein $R^4$ is hydrogen atom, hydroxy, $C_{1-3}$ alkyl, or $C_{1-3}$ alkoxy.

(Item 6)

The compound of Item 5 or a pharmaceutically acceptable salt thereof, wherein $R^4$ is hydrogen atom, hydroxy, or methoxy.

(Item 7)

The compound of any one of Items 1 to 6 or a pharmaceutically acceptable salt thereof, wherein $R^2$ is $C_{1-6}$ alkyl.

(Item 8)

The compound of any one of Items 1 to 7 or a pharmaceutically acceptable salt thereof, wherein $R^3$ is hydrogen atom, or $C_{1-3}$ alkyl which may be substituted with. 1-3 hydroxy.

(Item 9)

The compound of any one of Items 1 to 8 or a pharmaceutically acceptable salt thereof, wherein L is —O—, —$NR^Y$—, —C(O)—, —C(O)O—, —OC(O)—, —C(O)$NR^Y$—, —$NR^YC(O)$—, —$CH_2NR^Y$—, —$CH_2O$—, —OC(O)O—, —$NR^7C(O)$ O—, —OC(O)$NR^Y$—, —$NR^7C(O)NR^Y$—, —OC(S)$NR^Y$—, or —$NR^7C(S)NR^Y$—, wherein $R^7$ is hydrogen atom or $C_{1-6}$ alkyl, and $R^Y$ is hydrogen atom, $C_{1-6}$ alkyl, or $Y^2$, wherein $Y^2$ is —$(CH_2CH_2O)_n$—$R^8$ (wherein $R^8$ is hydrogen atom or $C_{1-6}$ alkyl, and n is an integer of 3-100)

(Item 10)

The compound of Item 9 or a pharmaceutically acceptable salt thereof, wherein L is —C(O)$NR^Y$—, —$CH_2NR^Y$—, —C(O)O—, or —$CH_2O$—.

(Item 11)

The compound of Item 9 or a pharmaceutically acceptable salt thereof, wherein L is —C(O)$NR^Y$— or —$CH_2NR^Y$—.

(Item 12)

The compound of Item 9 or a pharmaceutically acceptable salt thereof, wherein

L is —$CH_2NR^Y$—, and $R^Y$ is hydrogen atom, $C_{1-6}$ alkyl, or $Y^2$.

(Item 13)

The compound of Item 9 or a pharmaceutically acceptable salt thereof, wherein

L is —$CH_2NR^Y$—, and $R^Y$ is hydrogen atom or $C_{1-6}$ alkyl.

(Item 14)

The compound of any one of Items 1 to 13 or a pharmaceutically acceptable salt thereof, wherein $Y^1$ is —$(CH_2CH_2O)_m$—$R^6$, $R^6$ is hydrogen atom or $C_{1-6}$ alkyl, and m is an integer of 3-40.

(Item 15)

The compound of Item 14 or a pharmaceutically acceptable salt thereof, wherein $Y^1$ is —$(CH_2CH_2O)_m$—$R^6$, $R^6$ is hydrogen atom or $C_{1-6}$ alkyl, and m is an integer of 3-20.

(Item 16)

The compound of Item 1 or a pharmaceutically acceptable salt thereof, wherein the compound is a compound of formula (2):

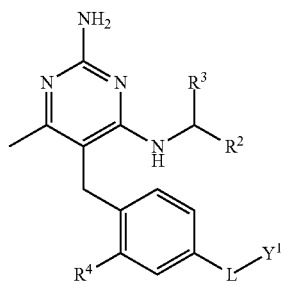

(2)

or formula (3):

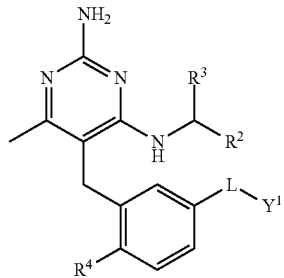

(3)

wherein $R^2$ is $C_{1-6}$ alkyl, $R^3$ is hydrogen atom, or $C_{1-3}$ alkyl which may be substituted with 1-3 hydroxy, $R^4$ is hydrogen atom, hydroxy, or methoxy, L is —$CH_2NR^Y$—, —C(O) $NR^Y$—, —C(O)O—, or —$CH_2O$—, $R^Y$ is hydrogen atom, $C_{1-6}$ alkyl, or $Y^2$, $Y^1$ is —$(CH_2CH_2O)_m$—$R^6$, $Y^2$ is —$(CH_2CH_2O)_n$—$R^8$, $R^6$ is hydrogen atom or $C_{1-6}$ alkyl, $R^8$ is hydrogen atom or $C_{1-6}$ alkyl, and m and n are independently an integer of 3-40.

(Item 17)

The compound of Item 1 or a pharmaceutically acceptable salt thereof, wherein the compound is a compound of formula (2):

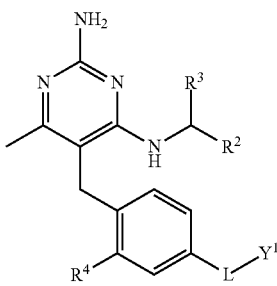

or formula (3):

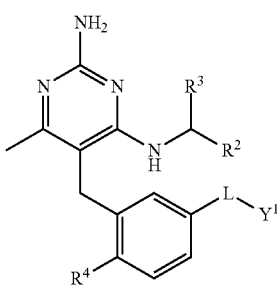

wherein
$R^2$ is $C_{1-6}$ alkyl,
$R^3$ is hydrogen atom, or $C_{1-3}$ alkyl which may be substituted with 1-3 hydroxy,
$R^4$ is hydrogen atom, hydroxy, or methoxy,
L is —$CH_2NR^Y$—,
$R^Y$ is hydrogen atom or $C_{1-6}$ alkyl,
$Y^1$ is —$(CH_2CH_2O)_m$—$R^6$,
$R^6$ is hydrogen atom or $C_{1-6}$ alkyl, and
m is an integer of 3-20.

(Item 18)
The compound of Item 1 or a pharmaceutically acceptable salt thereof, wherein the compound is a compound of formula (2):

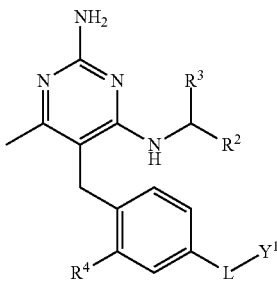

wherein
$R^2$ is $C_{1-6}$ alkyl,
$R^3$ is hydrogen atom, or $C_{1-3}$ alkyl which may be substituted with one hydroxy,
$R^4$ is hydrogen atom or methoxy,
L is —$CH_2NR^Y$—,
$R^Y$ is hydrogen atom or $C_{1-6}$ alkyl,
$Y^1$ is —$(CH_2CH_2O)_m$—$R^6$,
$R^6$ is hydrogen atom or $C_{1-6}$ alkyl, and
m is an integer of 3-40.

(Item 19)
The compound of Item 1 or a pharmaceutically acceptable salt thereof, which is selected from:
1-(4-{[2-amino-4-methyl-6-(pentylamino)pyrimidin-5-yl]methyl}-3-methoxyphenyl)-2-methyl-5,8,11,14-tetraoxa-2-azahexadecan-16-ol (Example 1),
1-{4-[(2-amino-4-{[(3S)-1-hydroxyhexan-3-yl]amino}-6-methylpyrimidin-5-yl)methyl]-3-methoxyphenyl}-2-methyl-5,8,11,14-tetraoxa-2-azahexadecan-16-ol (Example 2),
1-(3-{[2-amino-4-methyl-6-(pentylamino)pyrimidin-5-yl]methyl}-4-methoxyphenyl)-2-methyl-5,8,11,14-tetraoxa-2-azahexadecan-16-ol (Example 3),
1-(3-{[2-amino-4-methyl-6-(pentylamino)pyrimidin-5-yl]methyl}-4-hydroxyphenyl)-2-methyl-5,8,11,14-tetraoxa-2-azahexadecan-16-ol (Example 4),
4-[(2-amino-4-{[(2S)-1-hydroxypentan-2-yl]amino}-6-methylpyrimidin-5-yl)methyl]-N-(20-hydroxy-3,6,9,12,15,18-hexaoxaicosan-1-yl)-3-methoxybenzamide (Example 5),
2,5,8,11-tetraoxatridecan-13-yl 4-[(2-amino-4-{[(2S)-1-hydroxypentan-2-yl]amino}-6-methylpyrimidin-5-yl)methyl]-3-methoxybenzoate (Example 6),
5-{[2-methoxy-4-(2,5,8,11,14-pentaoxapentadecan-1-yl)phenyl]methyl}-6-methyl-$N^4$-pentylpyrimidine-2,4-diamine (Example 7),
1-(4-{[2-amino-4-methyl-6-(pentylamino)pyrimidin-5-yl]methyl}-3-methoxyphenyl)-2-methyl-5,8,11,14,17,20,23,26,29-nonaoxa-2-azahentriacontan-31-ol (Example 8),
1-(4-{[2-amino-4-methyl-6-(pentylamino)pyrimidin-5-yl]methyl}-3-methoxyphenyl)-2-methyl-5,8,11,14,17,20,23,26,29,32,35,38,41,44,47,50,53,56,59,62,65,68,71-tricosaoxa-2-azatriheptacontan-73-ol (Example 9),
1-(4-{[2-amino-4-methyl-6-(pentylamino)pyrimidin-5-yl]methyl}-3-methoxyphenyl)-2-methyl-5,8,11,14,17,20,23,26,29,32,35,38,41,44,47,50,53,56,59,62,65,68,71,74,77,80,83,86,89,92,95,98,101,104,107-pentatriacontaoxa-2-azanonahectan-109-ol (Example 10), and
12-[(4-{[2-amino-4-methyl-6-(pentylamino)pyrimidin-5-yl]methyl}-3-methoxyphenyl)methyl]-3,6,9,15,18,21-hexaoxa-12-azatricosan-1,23-diol (Example 11).

(Item 20)
The compound of Item 1 or a pharmaceutically acceptable salt thereof, which is selected from:
1-(4-{[2-amino-4-methyl-6-(pentylamino)pyrimidin-5-yl]methyl}-3-methoxyphenyl)-2-methyl-5,8,11,14-tetraoxa-2-azahexadecan-16-ol (Example 1),
1-{4-[(2-amino-4-{[(3S)-1-hydroxyhexan-3-yl]amino}-6-methylpyrimidin-5-yl)methyl]-3-methoxyphenyl}-2-methyl-5,8,11,14-tetraoxa-2-azahexadecan-16-ol (Example 2),
1-(3-{[2-amino-4-methyl-6-(pentylamino)pyrimidin-5-yl]methyl}-4-methoxyphenyl)-2-methyl-5,8,11,14-tetraoxa-2-azahexadecan-16-ol (Example 3), and
1-(3-{[2-amino-4-methyl-6-(pentylamino)pyrimidin-5-yl]methyl}-4-hydroxyphenyl)-2-methyl-5,8,11,14-tetraoxa-2-azahexadecan-16-ol (Example 4).

(Item 21)
A pharmaceutical composition comprising the compound of any one of Items 1 to 20 or a pharmaceutically acceptable salt thereof.

(Item 22)
The pharmaceutical composition of Item 21, which is an emulsion formulation, an oil-based suspension, a hydrogel formulation, or a lipid formulation.

(Item 23)
The pharmaceutical composition of Item 21, which is an emulsion formulation.
(Item 24)
The pharmaceutical composition of Item 23, wherein the emulsion formulation is a water-in-oil emulsion.
(Item 25)
The pharmaceutical composition of Item 24, wherein the emulsion formulation comprises (1) ethyl oleate, octyldodecyl myristate, sorbitan monooleate, glyceryl monooleate, polyoxyethylene hydrogenated castor oil 20, glycerin, and sodium dihydrogen phosphate, or (2) Montanide ISA 51VG.
(Item 26)
The pharmaceutical composition of Item 21, which is a lipid formulation.
(Item 27)
The pharmaceutical composition of Item 26, wherein the lipid formulation is a liposome formulation comprising phospholipid.
(Item 28)
The pharmaceutical composition of Item 26 or 27, wherein the lipid formulation is a liposome formulation comprising sterols.
(Item 29)
The pharmaceutical composition of Item 28, wherein the sterols is cholesterol.
(Item 30)
The pharmaceutical composition of any one of Items 27 to 29, wherein the liposome formulation comprises at least one additive selected from the group consisting of inorganic acid, inorganic acid salt, organic acid, organic acid salt, sugars, buffering agent, antioxidant, and polymers.
(Item 31)
The pharmaceutical composition of any one of Items 21 to 30, which further comprises an antigen.
(Item 32)
The pharmaceutical composition of Items 31, wherein the antigen is a pathogen-derived antigen or a tumor antigen.
(Item 33)
The pharmaceutical composition of Item 31, wherein the antigen is a tumor antigen.
(Item 34)
The pharmaceutical composition of Item 33, wherein the tumor antigen is a tumor antigen peptide.
(Item 35)
The pharmaceutical composition of Item 34, wherein the tumor antigen peptide comprises at least one peptide or a pharmaceutically acceptable salt thereof which is selected from the group consisting of the following amino acid sequences:

```
                                          (SEQ ID NO: 1)
          RMFPNAPYL, (SEQ ID NO: 8)
          ALLPAVPSL, (SEQ ID NO: 9)
          SLGEQQYSV, (SEQ ID NO: 10)
          RVPGVAPTL, (SEQ ID NO: 4)
          VLDFAPPGA, (SEQ ID NO: 11)
          CMTWNQMNL, (SEQ ID NO: 2)
          CYTWNQMNL, (SEQ ID NO: 18)
          TYAGCLSQIF,
``` formula (4):

```
    CRMFPNAPYL   (SEQ ID NO: 19)
    |
    CYTWNQMNL    (SEQ ID NO: 2)
``` wherein the bond between C-C is disulfide bond, and
formula (5):

```
    C
    |
    CYTWNQMNL   (SEQ ID NO: 2)
``` wherein the bond between C-C is disulfide bond; and
at least one peptide or a pharmaceutically acceptable salt thereof which is selected from the group consisting of the following amino acid sequences:

```
                                          (SEQ ID NO: 3)
          WAPVLDFAPPGASAYGSL, (SEQ ID NO: 12)
          CWAPVLDFAPPGASAYGSL, (SEQ ID NO: 13)
          WAPVLDFAPPGASAYGSLC, (SEQ ID NO: 14)
          CNKRYFKLSHLQMHSRKHTG, (SEQ ID NO: 15)
          CNKRYFKLSHLQMHSRKH, (SEQ ID NO: 16)
          CNKRYFKLSHLQMHSRK,
          and (SEQ ID NO: 17)
          KRYFKLSHLQMHSRKH.
```

(Item 36)
The pharmaceutical composition of Item 34, wherein the tumor antigen peptide comprises at least one peptide or a pharmaceutically acceptable salt thereof which is selected from the group consisting of the following amino acid sequences:

```
                                          (SEQ ID NO: 1)
          RMFPNAPYL, (SEQ ID NO: 8)
          ALLPAVPSL, (SEQ ID NO: 9)
          SLGEQQYSV, (SEQ ID NO: 10)
          RVPGVAPTL, (SEQ ID NO: 4)
          VLDFAPPGA,
```

```
                                            (SEQ ID NO: 11)
            CMTWNQMNL, (SEQ ID NO: 2)
            CYTWNQMNL,
``` and formula (4):

```
            CRMFPNAPYL    (SEQ ID NO: 19)
            |
            CYTWNQMNL     (SEQ ID NO: 2)
``` wherein the bond between C-C is disulfide bond, and
at least one peptide or a pharmaceutically acceptable salt thereof which is selected from the group consisting of the following amino acid sequences:

```
                                             (SEQ ID NO: 3)
            WAPVLDFAPPGASAYGSL, (SEQ ID NO: 12)
            CWAPVLDFAPPGASAYGSL, (SEQ ID NO: 13)
            WAPVLDFAPPGASAYGSLC, (SEQ ID NO: 14)
            CNKRYFKLSHLQMHSRKHTG (SEQ ID NO: 15)
            CNKRYFKLSHLQMHSRKH, (SEQ ID NO: 16)
            CNKRYFKLSHLQMHSRK,
and
                                            (SEQ ID NO: 17)
            KRYFKLSHLQMHSRKH.
```

(Item 37)

The pharmaceutical composition of Item 34, wherein the tumor antigen peptide is a combination of a peptide represented by the amino acid sequence of formula (4):

```
            CRMFPNAPYL    (SEQ ID NO: 19)
            |
            CYTWNQMNL     (SEQ ID NO: 2)
``` wherein the bond between C-C is disulfide bond, or a pharmaceutically acceptable salt thereof, and a peptide represented by the amino acid sequence of SEQ ID NO 3: WAPVLDFAPPGASAYGSL, or a pharmaceutically acceptable salt thereof.

(Item 38)

A vaccine adjuvant comprising the compound of any one of Items 1 to 20 or a pharmaceutically acceptable salt thereof.

(Item 39)

The vaccine adjuvant of Item 38, which is a vaccine adjuvant for cancer vaccine.

(Item 40)

The compound of any one of Items 1 to 20 or a pharmaceutically acceptable salt thereof, which is used as a vaccine adjuvant.

(Item 41)

The compound of any one of Items 1 to 20 or a pharmaceutically acceptable salt thereof, which is used as a vaccine adjuvant for cancer vaccine.

(Item 42)

CTL inducer comprising the compound of any one of Items 1 to 20 or a pharmaceutically acceptable salt thereof.

(Item 43)

An immunostimulant comprising the compound of any one of Items 1 to 20 or a pharmaceutically acceptable salt thereof.

(Item 44)

A method for inducing CTL in mammal, comprising administering the compound of any one of Items 1 to 20 or a pharmaceutically acceptable salt thereof to the mammal.

(Item 45)

A method for enhancing the CTL induction in mammal, comprising administering the compound of any one of Items 1 to 20 or a pharmaceutically acceptable salt thereof to the mammal.

(Item 46)

A method for enhancing specific immune response in mammal to an antigen, comprising administering the compound of any one of Items 1 to 20 or a pharmaceutically acceptable salt thereof to the mammal.

(Item 47)

Use of the compound of any one of Items 1 to 20 or a pharmaceutically acceptable salt thereof in the preparation of a vaccine adjuvant.

(Item 48)

Use of the compound of any one of Items 1 to 20 or a pharmaceutically acceptable salt thereof in the preparation of a vaccine adjuvant for cancer vaccine.

(Item 49)

A kit comprising a) the compound of any one of Items 1 to 20 or a pharmaceutically acceptable salt thereof, or a pharmaceutical composition comprising the compound of any one of Items 1 to 20 or a pharmaceutically acceptable salt thereof; and b) an antigen or a pharmaceutical composition comprising an antigen.

(Item 50)

A kit comprising a) the compound of Item 1 or a pharmaceutically acceptable salt thereof, or a pharmaceutical composition comprising the compound of Item 1 or a pharmaceutically acceptable salt thereof; and b) a tumor antigen or a pharmaceutical composition comprising a tumor antigen.

(Item 51)

A kit comprising a) the compound of Item 1 or a pharmaceutically acceptable salt thereof, or a pharmaceutical composition comprising the compound of Item 1 or a pharmaceutically acceptable salt thereof; and b) a pathogen-derived antigen or a pharmaceutical composition comprising a pathogen-derived antigen.

DESCRIPTION OF EMBODIMENTS

Figure 1:
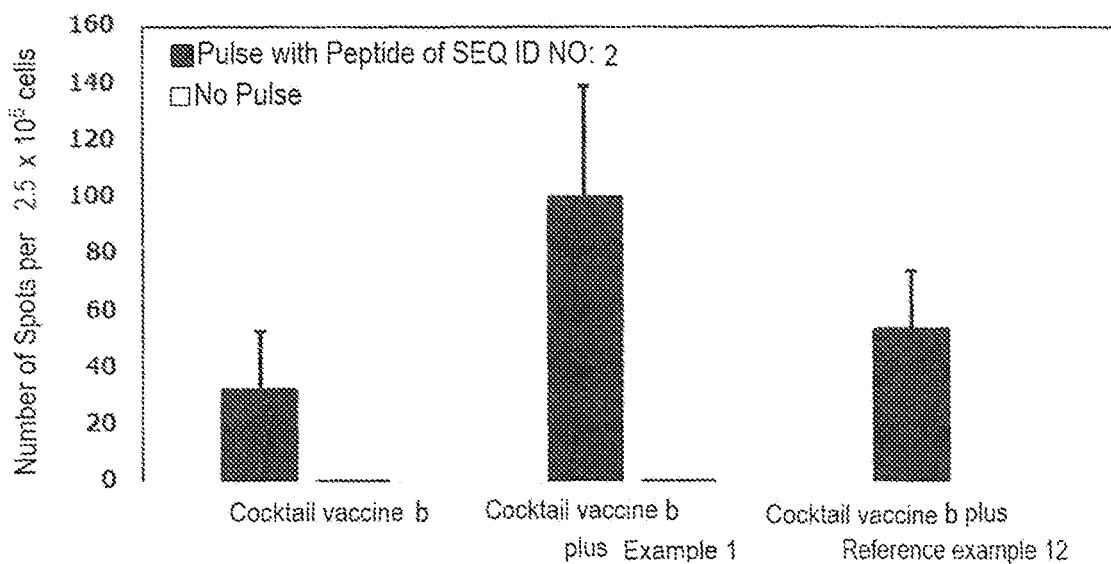
FIG. 1 shows the results of Test 3, i.e., Compound of formula 4 and Peptide SEQ ID No. 3 were mixed with Montanide ISA 51 VG to prepare a cocktail vaccine, the compound prepared in Example 1 or Reference example 12 was added to the cocktail vaccine to prepare a vaccine, and in vivo CTL induction for SEQ ID No. 2 by the prepared vaccine was tested in IFNγ ELISPOT assay with a HLA-A*24:02 transgenic mouse. The results are shown in FIG. 1.

Hereinafter, terms used herein are explained as follows.

The number of substituents that are defined posterior to "optionally-substituted" or "substituted" should not be limited, if it is possible to be substituted. Unless otherwise specified, the definition of each substituent group also extends over the case of partially-including the substituent group or the case of the substituent group existing on another substituent group.

The "halogen" used herein includes, for example, fluorine, chlorine, bromine, and iodine. It is preferably fluorine or chlorine, more preferably fluorine.

The "$C_{1-6}$ alkyl" means straight or branched chain saturated hydrocarbon group having 1 to 6 carbon atoms. The $C_{1-6}$ alkyl includes preferably "$C_{1-4}$ alkyl", more preferably "$C_{1-3}$ alkyl". The "$C_{1-6}$ alkyl" includes, for example, methyl, ethyl, propyl, 1-methylethyl, butyl, 2-methylpropyl, 1-methylpropyl, 1,1-dimethylethyl, pentyl, 3-methylbutyl, 2-methylbutyl, 2,2-dimethylpropyl, 1-ethylpropyl, 1,1-dimethylpropyl, hexyl, 4-methylpentyl, 3-methylpentyl, 2-methylpentyl, and 1-methylpentyl, and the "$C_1$-4 alky" includes the examples of the "$C_{1-6}$ alkyl" provided that the number of carbon atoms is 1-4. The "$C_{1-3}$ alkyl" includes the examples of the "$C_{1-6}$ alkyl" provided that the number of carbon atoms is 1-3.

The "$C_{1-6}$ alkoxy" means "$C_{1-6}$ alkyloxy", and the part "$C_{1-6}$ alkyl" is as defined in the said "$C_{1-6}$ alkyl". The "$C_{1-6}$ alkoxy" includes preferably "$C_{1-4}$ alkoxy", more preferably "$C_{1-3}$ alkoxy". The "$C_{1-6}$ alkoxy" includes, for example, methoxy, ethoxy, propoxy, 1-methylethoxy, butoxy, 2-methylpropoxy, 1-methylpropoxy, 1,1-dimethylethoxy, pentyloxy, 3-methylbutoxy, 2-methylbutoxy, 2,2-dimethylpropoxy, 1-ethylpropoxy, 1,1-dimethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, and 1,2-dimethylbutoxy, and the "$C_{1-4}$ alkoxy" includes the examples of the "$C_{1-6}$ alkoxy" provided that the number of carbon atoms is 1-4. The "$C_{1-3}$ alkoxy" includes the examples of the "$C_{1-6}$ alkoxy" provided that the number of carbon atoms is 1-3.

The "linker" means a bivalent group having two binding sites in the functional group. The bivalent group includes, for example, $C_{1-6}$ alkylene, $C_{2-7}$ alkenylene, $C_{2-7}$ alkynylene, $C_{3-10}$ cycloalkylene, $C_{6-10}$ arylene, $C_{5-10}$ heteroarylene, ether, amine, carbonyl, ester, amido, carbonate, carbamate, thiocarbamate, and thiourea. And, a bivalent group prepared by optionally-combining these exemplified bivalent groups may be used herein. The linker includes, preferably, —O—, —NR$^Y$—, —C(O)—, —C(O)O—, —OC(O)—, —C(O)NR$^Y$—, —NR$^Y$C(O)—, —CH$_2$NR$^Y$—, —CH$_2$O—, —OC(O)O—, —NR$^7$C(O)O—, —OC(O)NR$^Y$—, —NR$^7$C(O)NR$^Y$—, —OC(S)NR$^Y$—, and —NR$^7$C(S)NR$^Y$—, wherein R$^Y$ and R$^7$ are as defined in Item 9, and more preferably —C(O)NR$^Y$— and —CH$_2$NR$^Y$—, and even more preferably —CH$_2$NR$^Y$—. As for the two binding sites in these exemplified linkers, the left binding site is attached to the benzene ring in the compound of formula (1), and the right binding site is attached to Y$^1$ in the compound of formula (1). Specifically, when linker L is "—CH$_2$NR$^Y$—", the compound of formula (1) is represented as the following structure.

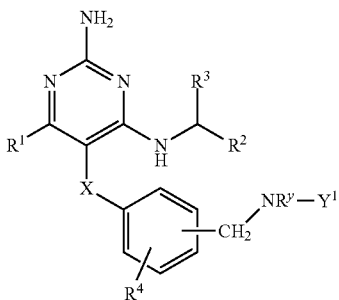

The "$C_{1-6}$ alkylene" means straight or branched chain saturated hydrocarbon group having 1 to 6 carbon atoms. The "$C_{1-6}$ alkylene" includes, for example, methylene, ethylene, propylene, 1-methylethylene, butylene, 2-methylpropylene, 1-methylpropylene, 1,1-dimethylethylene, pentylene, 3-methylbutylene, 2-methylbutylene, 2,2-dimethylpropylene, 1-ethylpropylene, 1,1-dimethylpropylene, hexylene, 4-methylpentylene, and 3-methylpentylene, and preferably methylene and ethylene.

The "$C_{2-7}$ alkenylene" means straight or branched chain unsaturated hydrocarbon group having 2 to 7 carbon atoms and 1 to 3 double bonds. The "$C_{2-7}$ alkenylene" includes, for example, vinylene, propenylene, methylpropenylene, butenylene, methylbutenylene, pentenylene, hexenylene, and heptenylene, and preferably vinylene and propenylene.

The "$C_{2-7}$ alkynylene" means straight or branched chain unsaturated hydrocarbon group having 2 to 7 carbon atoms and one triple bond. The "$C_{2-7}$ alkynylene" includes, for example, ethynylene, propynylene, methyl propynylene, butynylene, methylbutynylene, pentynylene, hexynylene, and heptynylene, and preferably ethynylene and propynylene.

The "$C_{3-10}$ cycloalkylene" means cyclic alkylene having 3 to 10 carbon atoms, which may have a bridged structure. The "$C_{3-10}$ cycloalkylene" includes, for example, cyclopropylene, cyclobutylene, cyclopentylene, cyclohexylene, cycloheptylene, cyclooctylene, and adamantylene, and preferably cyclopropylene and cyclobutylene.

The "$C_{6-10}$ arylene" means aromatic hydrocarbon group having 6 to 10 carbon atoms. The "$C_{6-10}$ arylene" includes, for example, phenylene, 1-naphthylene, and 2-naphthylene, and preferably phenylene.

The "$C_{5-10}$ heteroarylene" means monocyclic 5- to 7-membered aromatic heterocycle or bicyclic 8- to 10-membered aromatic heterocycle having 1 to 4 atoms selected independently from the group consisting of nitrogen atom, oxygen atom and sulfur atom. The "$C_{5-10}$ heteroarylene" includes, for example, pyridylene, pyridazinylene, isothiazolylene, pyrrolylene, furylene, thienylene, thiazolylene, imidazolylene, pyrimidinylene, thiadiazolylene, pyrazolylene, oxazolylene, isooxazolylene, pyrazinylene, triazinylene, triazolylene, imidazolidinylene, oxadiazolylene, triazolylene, tetrazolylene, indolylene, indazolylene, quinolylene, isoquinolylene, benzofuranylene, benzothienylene, benzooxazolylene, benzothiazolylene, benzoisooxazolylene, benzoisothiazolylene, benzotriazolylene, benzoimidazolylene, and 6,11-dihydrodibenzo[b,e]thiepinylene. Preferably, it includes pyridylene, pyrimidinylene, quinolylene, and isoquinolylene, and more preferably pyridylene, furylene, and thienylene.

In the present compound of formula (1), preferred X, $Y^1$, $Y^2$, $R^1$, $R^2$, $R^3$, $R^4$, $R^5$, $R^6$, $R^7$, $R^8$, $R^Y$, L, m, and n are shown below, but the technical scope of the present invention is not limited to the scope of compounds listed below.

X includes preferably methylene, oxygen atom, and $NR^5$ wherein $R^5$ is hydrogen atom or $C_{1-6}$ alkyl, and more preferably methylene.

$Y^1$ includes —$(CH_2CH_2O)_m$—$R^6$.

$Y^2$ includes —$(CH_2CH_2O)_n$—$R^8$.

$R^1$ includes preferably $C_{1-6}$ alkyl which may be substituted with 1-3 the same or different halogens. More preferably, it includes $C_{1-6}$ alkyl such as methyl, ethyl, propyl, 1-methylethyl, butyl, 2-methylpropyl, 1-methylpropyl, and 1,1-dimethylethyl, and even more preferably methyl.

$R^2$ includes preferably
(1) hydrogen atom, and
(2) $C_{1-6}$ alkyl which may be substituted with 1-3 substituents selected independently from halogen and hydroxy. More preferably, it includes hydrogen atom and $C_{1-6}$ alkyl, further preferably $C_{1-6}$ alkyl, and even more preferably $C_{3-4}$ alkyl.

$R^3$ includes preferably
(1) hydrogen atom, and
(2) $C_{1-6}$ alkyl which may be substituted with 1-3 substituents selected independently from halogen and hydroxy.

$R^3$ includes more preferably
(1) hydrogen atom, and
(2) $C_{1-3}$ alkyl which may be substituted with 1-3 hydroxy.

$R^3$ includes even more preferably
(1) hydrogen atom, and
(2) $C_{1-3}$ alkyl which may be substituted with one hydroxy.

$R^3$ includes even more preferably
(1) hydrogen atom, and
(2) $C_{1-2}$ alkyl which may be substituted with one hydroxy.

$R^4$ includes preferably
(1) hydrogen atom,
(2) halogen,
(3) hydroxy,
(4) $C_{1-6}$ alkyl which may be substituted with 1-3 the same or different halogens,
(5) $C_{1-6}$ alkoxy which may be substituted with 1-3 the same or different halogens, and
(6) cyano.

$R^4$ includes more preferably
(1) hydrogen atom,
(2) halogen,
(3) hydroxy,
(4) $C_{1-6}$ alkyl which may be substituted with 1-3 the same or different halogens, and
(5) $C_{1-6}$ alkoxy which may be substituted with 1-3 the same or different halogens.

$R^4$ includes even more preferably hydrogen atom, hydroxy, $C_{1-3}$ alkyl, and $C_{1-3}$ alkoxy.

$R^4$ includes even more preferably hydrogen atom, hydroxy, and methoxy, further even more preferably hydroxy and methoxy, and the most preferably hydrogen atom and methoxy.

$R^5$ includes preferably hydrogen atom and $C_{1-3}$ alkyl. More preferably, it includes hydrogen atom, methyl, ethyl, and propyl.

$R^6$ and $R^8$ include preferably independently hydrogen atom, and $C_{1-3}$ alkyl, more preferably independently hydrogen atom, methyl, ethyl, and propyl, and even more preferably hydrogen atom and methyl.

$R^7$ includes preferably hydrogen atom and $C_{1-3}$ alkyl. More preferably, it includes hydrogen atom, methyl, ethyl, and propyl.

L includes preferably
(1) —O—,
(2) —NR$^Y$—,
(3) —C(O)—,
(4) —C(O)O—,
(5) —OC(O)—,
(6) —C(O)NR$^Y$—,
(7) —NR$^Y$C(O)—,
(8) —CH$_2$NR$^Y$—,
(9) —CH$_2$O—,
(10) —OC(O)O—,
(11) —NR$^7$C(O)O—,
(12) —OC(O)NR$^Y$—,
(13) —NR$^7$C(O)NR$^Y$—,
(14) —OC(S)NR$^Y$—, and
(15) —NR$^7$C(S)NR$^Y$—.
L includes more preferably
(1) —O—,
(2) —NR$^Y$—,
(3) —C(O)—,
(4) —C(O)O—,
(5) —OC(O)—,
(6) —C(O)NR$^Y$—,
(7) —NR$^Y$C(O)—,
(8) —CH$_2$NR$^Y$—, and
(9) —CH$_2$O—.
L includes even more preferably
(1) —C(O)NR$^Y$—,
(2) —CH$_2$NR$^Y$—,
(3) —C(O)O—, and
(4) —CH$_2$O—.
L includes even more preferably
(1) —C(O)NR$^Y$—, and
(2) —CH$_2$NR$^Y$—.
L includes the most preferably —CH$_2$NR$^Y$—.

The substitution positions of X, L, and R$^4$ in the benzene ring may be preferably the following (1a) or (1aa).

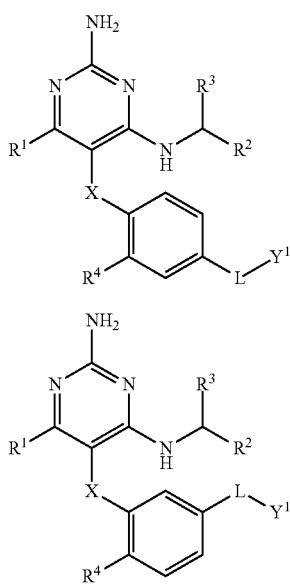

R$^Y$ includes preferably hydrogen atom, C$_{1-6}$ alkyl, and Y$^2$, more preferably hydrogen atom and C$_{1-6}$ alkyl, even more preferably hydrogen atom, methyl, ethyl, and propyl.

In another embodiment, R$^Y$ includes preferably hydrogen atom, C$_{1-6}$ alkyl, and Y$^2$, and more preferably hydrogen atom, methyl, and Y$^2$.

m and n include preferably independently an integer of 3-40, more preferably an integer of 4-40, and even more preferably an integer of 4-36.

In another embodiment, m and n include independently an integer of 3-40, preferably an integer of 3-20, and more preferably an integer of 5-20.

Preferred compounds of formula (1) include the following compounds or a pharmaceutically acceptable salt thereof.

In a preferred embodiment, the present compound of formula (1) includes the following (A).

(A)

A compound of formula (1) or a pharmaceutically acceptable salt thereof, wherein X is methylene, oxygen atom, sulfur atom, SO, SO$_2$, or NR$^5$, R$^1$ is C$_{1-6}$ alkyl which may be substituted with 1-5 substituents selected independently from the group consisting of halogen, hydroxy, and C$_{1-6}$ alkoxy, R$^2$ are R$^3$ are independently
(1) hydrogen atom, or
(2) C$_{1-6}$ alkyl which may be substituted with 1-5 substituents selected independently from the group consisting of halogen, hydroxy, and C$_{1-6}$ alkoxy, R$^4$ is
(1) hydrogen atom,
(2) halogen,
(3) hydroxy,
(4) C$_{1-6}$ alkyl which may be substituted with 1-3 the same or different halogens,
(5) C$_{3-6}$ alkoxy which may be substituted with 1-3 the same or different halogens, or
(6) cyano, R$^5$ is
(1) hydrogen atom, or
(2) C$_{1-6}$ alkyl, R$^6$ and R$^8$ are independently
(1) hydrogen atom, or
(2) C$_{1-6}$ alkyl, R$^7$ is
(1) hydrogen atom, or
(2) C$_{1-6}$ alkyl, L is
(1) —O—,
(2) —NR$^Y$—,
(3) —C(O)—,
(4) —C(O)O—,
(5) —OC(O)—,
(6) —C(O)NR$^Y$—,
(7) —NR$^Y$C(O)—,
(8) —CH$_2$NR$^Y$—,
(9) —CH$_2$O—,
(10) —OC(O)O—,
(11) —NR$^7$C(O)O—,
(12) —OC(O)NR$^Y$—,
(13) —NR$^7$C(O)NR$^Y$—,
(14) —OC(S)NR$^Y$—, or
(15) —NR$^7$C(S)NR$^Y$—, R$^Y$ is
(1) hydrogen atom,
(2) C$_{1-6}$ alkyl, or
(3) Y$^2$, Y$^1$ is —(CH$_2$CH$_2$O)$_m$—R$^6$,
Y$^2$ is —(CH$_2$CH$_2$O)$_n$—R$^8$, and
m and n are independently an integer of 3-100.

In a preferred embodiment, the present compound of formula (1) includes the following (B).

(B)

A compound of formula (1) or a pharmaceutically acceptable salt thereof, wherein X is methylene, oxygen atom, or $NR^5$, $R^1$ is $C_{1-6}$ alkyl which may be substituted with 1-3 the same or different halogens, $R^2$ is
(1) hydrogen atom, or
(2) $C_{1-6}$ alkyl, $R^3$ is
(1) hydrogen atom, or
(2) $C_{1-6}$ alkyl which may be substituted with 1-3 hydroxy, $R^4$ is
(1) hydrogen atom,
(2) halogen,
(3) hydroxy,
(4) $C_{1-6}$ alkyl which may be substituted with 1-3 the same or different halogens, or
(5) $C_{1-6}$ alkoxy which may be substituted with 1-3 the same or different halogens, $R^5$ is
(1) hydrogen atom, or
(2) $C_{1-3}$ alkyl, $R^6$ and $R^8$ are independently
(1) hydrogen atom, or
(2) $C_{1-3}$ alkyl, L is
(1) —O—,
(2) —$NR^Y$—,
(3) —C(O)—,
(4) —C(O)O—,
(5) —OC(O)—,
(6) —C(O) $NR^Y$—,
(7) —$NR^Y$C(O)—,
(8) —$CH_2NR^Y$—, or
(9) —$CH_2O$—, $R^Y$ is
(1) hydrogen atom,
(2) $C_{1-6}$ alkyl, or
(3) $Y^2$, $Y^1$ is —$(CH_2CH_2O)_m$—$R^6$, $Y^2$ is —$(CH_2CH_2O)_n$—$R^8$, and m and n are independently an integer of 3-40.

In a preferred embodiment, the present compound of formula (1) includes the following (C).

(C)

A compound of formula (1) or a pharmaceutically acceptable salt thereof, wherein X is methylene, $R^1$ is methyl, ethyl, propyl, 1-methylethyl, butyl, 2-methylpropyl, 1-methylpropyl, or 1,1-dimethylethyl, $R^2$ is $C_{1-6}$ alkyl, $R^3$ is
(1) hydrogen atom, or
(2) $C_{1-3}$ alkyl which may be substituted with one hydroxy, $R^4$ is
(1) hydrogen atom
(2) hydroxy
(3) $C_{1-3}$ alkyl, or
(4) $C_{1-3}$ alkoxy, $R^6$ and $R^8$ are independently hydrogen atom, methyl, ethyl or propyl, L is
(1) —C(O) $NR^Y$—,
(2) —$CH_2NR^Y$—, (3) —C(O)O—, or
(4) —$CH_2O$—, $R^Y$ is hydrogen atom, methyl, ethyl, propyl, or $Y^2$, $Y^1$ is —$(CH_2CH_2O)_m$—$R^6$, $Y^2$ is —$(CH_2CH_2O)_n$—$R^8$, and m and n are independently an integer of 3-40.

In a preferred embodiment, the present compound of formula (1) includes the following (D).

(D)

A compound of formula (2) or (3) or a pharmaceutically acceptable salt thereof,

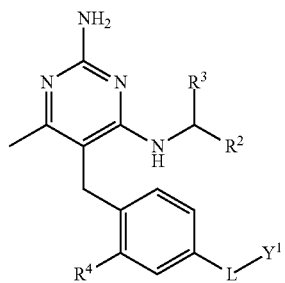

(2)

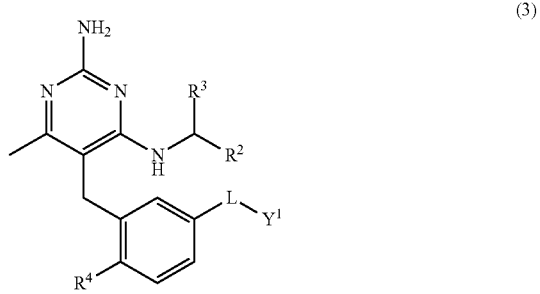

(3)

wherein $R^2$ is $C_{1-6}$ alkyl, $R^3$ is hydrogen atom, or $C_{1-3}$ alkyl which may be substituted with 1-3 hydroxy, $R^4$ is hydrogen atom, hydroxy, or methoxy, L is —$CH_2NR^Y$—, —C(O) $NR^Y$—, —C(O)O—, or —$CH_2O$—, $R^Y$ is hydrogen atom, methyl, ethyl, propyl, or $Y^2$, $Y^1$ is —$(CH_2CH_2O)_m$—$R^6$, $Y^2$ is —$(CH_2CH_2O)_n$—$R^8$, $R^6$ and $R^8$ are independently hydrogen atom, methyl, ethyl, or propyl, and m and n are independently an integer of 3-40.

In another embodiment, the present compound of formula (1) includes the following (E).

(E)

A compound of formula (2) or a pharmaceutically acceptable salt thereof, (2)

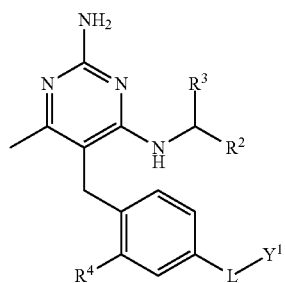

wherein $R^2$ is $C_{1-6}$ alkyl, $R^3$ is hydrogen atom, or $C_{1-3}$ alkyl which may be substituted with one hydroxy, $R^4$ is hydrogen atom, or methoxy, L is —$CH_2NR^Y$—, $R^Y$ is hydrogen atom, methyl, ethyl, or propyl, $Y^1$ is —$(CH_2CH_2O)_m$—$R^6$, $R^6$ is hydrogen atom, methyl, ethyl, or propyl, and m is an integer of 4-36.

The processes for preparing the compound of the present invention are shown below. For example, the compound of the formula (1) or a pharmaceutically acceptable salt thereof can be produced by the following processes.

Process A-1

In compounds according to formula (1) or a pharmaceutically acceptable salt thereof, the compound (a1-2) which has a linker of —$CR^{A1}R^{A2}NR^Y$— or —$CR^{A1}R^{A2}O$— can be prepared by the following process.

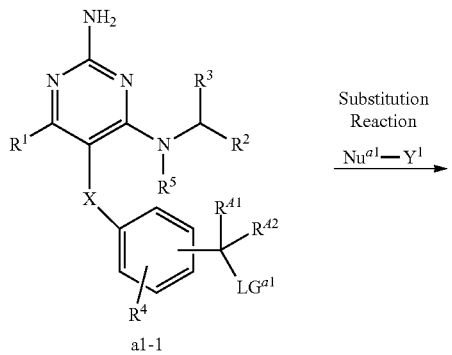

a1-1

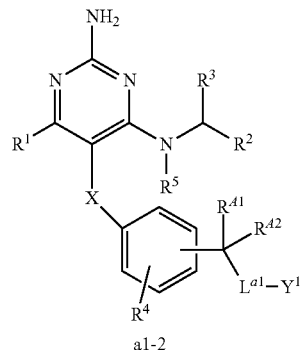

a1-2 wherein $R^1$, $R^2$, $R^3$, $R^4$, $R^5$, X, and $Y^1$ are as defined in Item 1, $R^{A1}$ and $R^{A2}$ are independently hydrogen atom or $C_{1-6}$ alkyl, $LG^{a1}$ is a leaving group, $Nu^{a1}$ is a nucleophile, and $L^{a1}$ is a linker prepared in the present process.

The present process is a substitution reaction to substitute a leaving group, $LG^{a1}$ with a nucleophile, $Nu^{a1}$—$Y^1$. In the present process, Compound (a1-2) can be obtained by reacting Compound (a1-1) and $Nu^{a1}$—$Y^1$ in the presence or absence of a suitable base in a suitable solvent. The leaving group includes, but should not be limited to, preferably fluorine, chlorine, bromine, iodine, methanesulfonate, ethanesulfonate, and p-toluenesulfonate, and more preferably chlorine, bromine, and methanesulfonate. The nucleophile includes, but should not be limited to, preferably amine which may be substituted with $R^Y$ defined in Item 9, alcohol, and thiol, and more preferably amine which may be substituted with $R^Y$ defined in Item 9, and alcohol. The base used herein can be selected from the bases exemplified below, preferably which includes sodium hydride and potassium hydride. The solvent used herein can be selected from the solvents exemplified below, preferably which includes DMF. The reaction time is generally about 5 minutes to about 48 hours, and preferably about 10 minutes to about 24 hours. The reaction temperature is generally about −78° C. to about 100° C., and preferably about 0° C. to about 100° C.

Process A-2

In compounds according to formula (1) or a pharmaceutically acceptable salt thereof, the compound (a2-2) which has a linker of —O—, —$NR^Y$—, —C(O)O—, —$CH_2NR^Y$—, or —$CH_2O$— can be prepared by the following process.

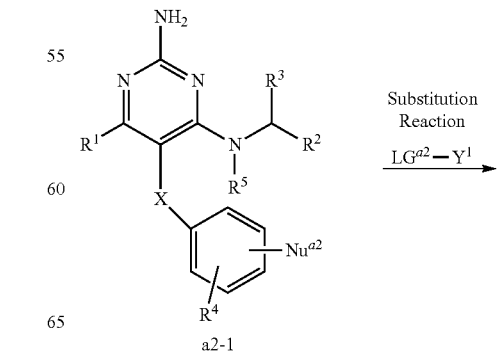

a2-1

-continued

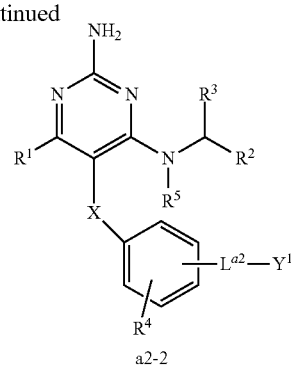

a2-2 wherein $R^1$, $R^2$, $R^3$, $R^4$, $R^5$, X, and $Y^1$ are as defined in Item 1, $LG^{a2}$ is a leaving group, $Nu^{a2}$ is a nucleophile, and $L^{a2}$ is a linker prepared in the present process.

The present process is a substitution reaction to substitute a leaving group, $LG^{a2}$ with a nucleophile, $Nu^{a2}$. In the present process, Compound (a2-2) can be obtained by reacting Compound (a2-1) and $LG^{a2}$-$Y^1$ in the presence or absence of a suitable base in a suitable solvent. $LG^{a2}$, $Nu^{a2}$, and $L^{a2}$ are identical to the leaving group, the nucleophile, and the linker mentioned in Process A-1, respectively. Each reaction condition of the present process complies with Process A-1.

The processes for preparing the compound of the present invention are shown below. For example, the compound of the formula (1) or a pharmaceutically acceptable salt thereof can be produced by the following processes.

Process B-1

In compounds according to formula (1) or a pharmaceutically acceptable salt thereof, the compound (b1-2) which has a linker of —$CH_2NR^Y$— can be prepared by the following process.

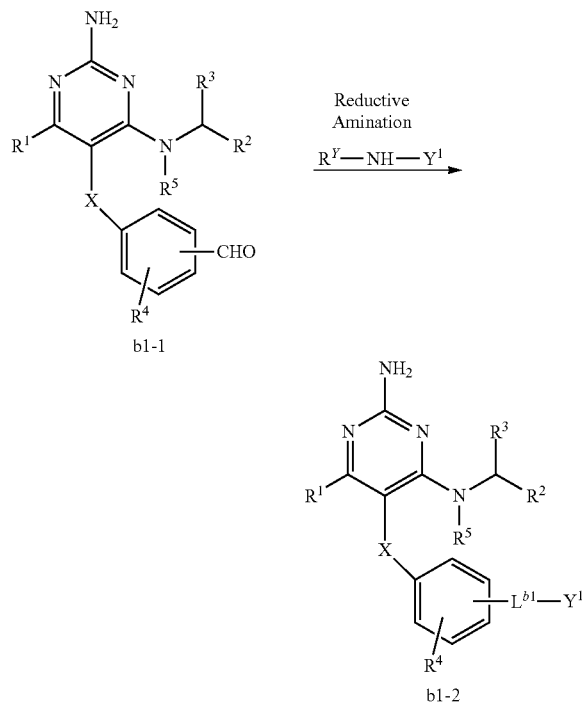

wherein $R^1$, $R^2$, $R^3$, $R^4$, $R^5$, X, and $Y^1$ are as defined in Item 1, $R^Y$ is as defined as Item 9, and $L^{b1}$ is a linker prepared in the present process.

The present process is a reductive amination with an aldehyde and an amine. In the present process, Compound (b1-2) can be obtained by reacting Compound (b1-1) and $R^Y$—NH—$Y^1$ in the presence of a suitable reductant in a suitable solvent. The reductant used herein includes, but not limited to, preferably sodium borohydride, triacetoxyborohydride, and picoline borane. The solvent used herein can be selected from the solvents exemplified below, preferably which includes THF and chloroform. The reaction time is generally about 5 minutes to about 48 hours, and preferably about 10 minutes to about 24 hours. The reaction temperature is generally about −78° C. to about 100° C., and preferably about 0° C. to about 100° C.

Process B-2

In compounds according to formula (1) or a pharmaceutically acceptable salt thereof, the compound (b2-2) which has a linker of —$NR^Y$— or —$CH_2NR^Y$— can be prepared by the following process.

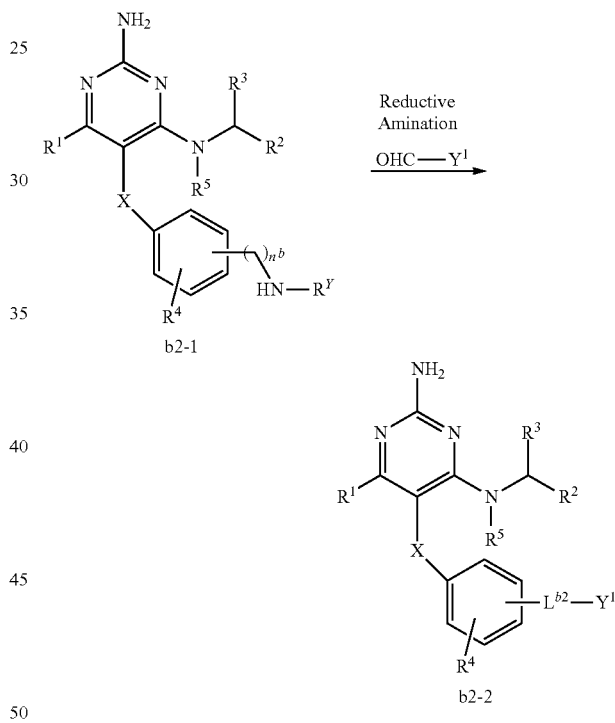

wherein $R^1$, $R^2$, $R^3$, $R^4$, $R^5$, X, and $Y^1$ are as defined in Item 1, $R^Y$ is as defined in Item 9, $n^b$ is 0 or 1, and $L^{b2}$ is a linker prepared in the present process.

The present process is a reductive amination with an aldehyde and an amine. In the present process, Compound (b2-2) can be obtained by reacting Compound (b2-1) and $Y^1$—CHO in the presence of a suitable reductant in a suitable solvent. Each reaction condition of the present process complies with Process B-1.

The processes for preparing the compound of the present invention are shown below. For example, the compound of the formula (1) or a pharmaceutically acceptable salt thereof can be produced by the following process.

Process C-1

In compounds according to formula (1) or a pharmaceutically acceptable salt thereof, the compound (c1-2) which has a linker of —O—, —NR$^Y$—, or —NR$^Y$C(O)— can be prepared by the following process.

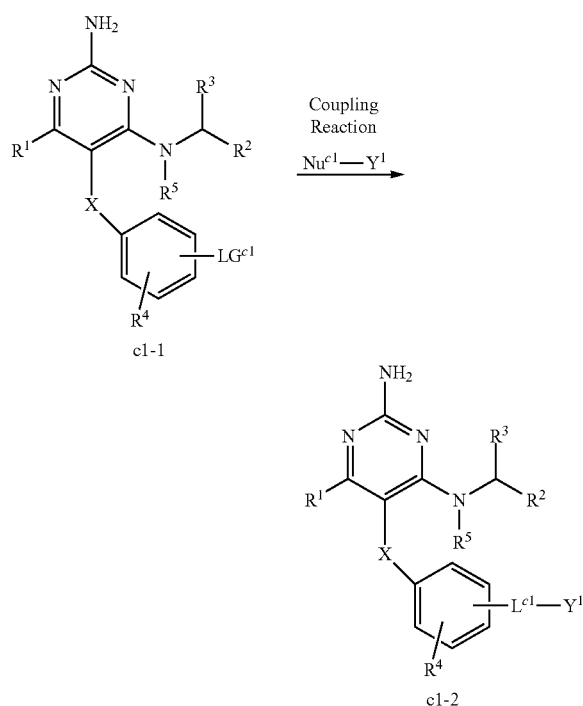

c1-1

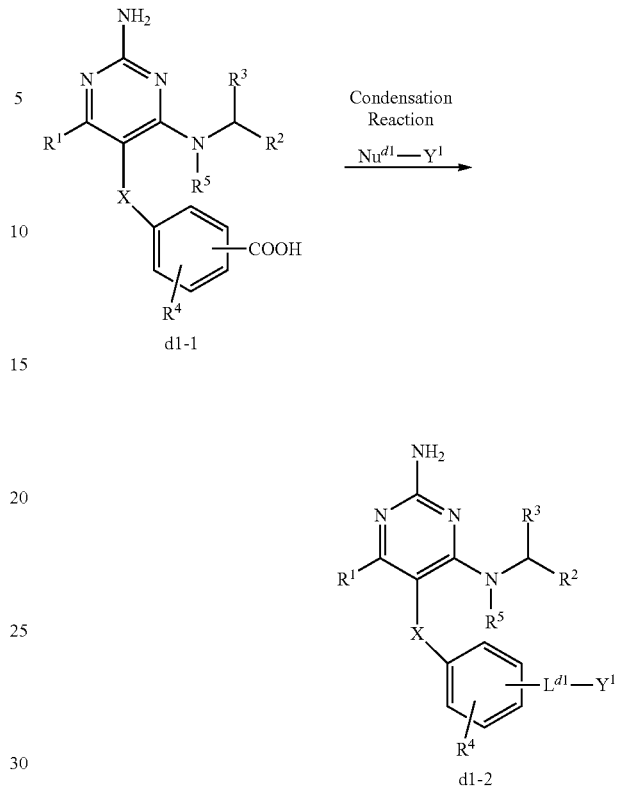

d1-1 c1-2 d1-2 wherein $R^1$, $R^2$, $R^3$, $R^4$, $R^5$, X, and $Y^1$ are as defined in Item 1, LG$^{c1}$ is a leaving group, Nu$^{c1}$ is a nucleophile, and L$^{c1}$ is a linker prepared in the present process.

The present process is a coupling reaction with a leaving group (LG$^{c1}$) and a nucleophile (Nu$_{c1}$—Y$^1$). In the present process, Compound (c1-2) can be obtained by reacting Compound (c1-1) and a nucleophile (Nu$^{c1}$—Y$^1$) in the presence of a suitable catalyst in the presence or absence of a suitable base in a suitable solvent. The catalyst used herein includes a transition metal such as palladium or a salt thereof, a complex containing it, and a carrier-supported (e.g. polymer-supported) one. The leaving group includes, but should not be limited to, preferably boronic acid, boronate, halogen, and trifluoromethanesulfonate, and more preferably boronic acid, boronate, bromine atom, iodine atom, and trifluoromethanesulfonate. The nucleophile includes, but should not be limited to, amine which may be substituted with R$^Y$ defined in Item 9, alcohol, alkylmagnesium, alkylzinc, and alkyllithium, and more preferably amine which may be substituted with $C_{1-6}$ alkyl, and alcohol. The solvent used herein can be selected from the solvents exemplified below, preferably which includes dioxane-water mixture. The reaction time is generally about 5 minutes to about 48 hours, and preferably about 10 minutes to about 24 hours. The reaction temperature is generally about −78° C. to about 100° C., and preferably about 0° C. to about 100° C.

The processes for preparing the compound of the present invention are shown below. For example, the compound of the formula (1) or a pharmaceutically acceptable salt thereof can be produced by the following processes.

Process D-1

In compounds according to formula (1) or a pharmaceutically acceptable salt thereof, the compound (d1-2) which has a linker of —C(O)O— or —C(O)NR$^Y$-linker can be prepared by the following process.

wherein $R^1$, $R^2$, $R^3$, $R^4$, $R^5$, X, and $Y^1$ are as defined in Item 1, Nu$^{d1}$ is a nucleophile, and L$^{d1}$ is a linker prepared in the present process.

The present process is a condensation reaction with Compound (d1-1) which has a carboxylic acid and Nu$^{d1}$—Y$^1$. In the present process, Compound (d1-2) can be obtained by reacting Compound (d1-1) and a nucleophile (Nu$^{d1}$—Y$^1$) in the presence of a suitable condensation agent in the presence or absence of a suitable base in a suitable solvent. The nucleophile includes, but should not be limited to, preferably amine which may be substituted with R$^Y$ defined in Item 9, alcohol, and thiol, and more preferably amine which may be substituted with one $C_{1-6}$ alkyl, and alcohol. The condensation agent used herein can be selected from condensation agents used in conventional manners, preferably which includes HBTU, HATU, and 1-ethyl-3-(3-dimethylaminopropyl)carbodiimide (including its hydrochloride). The base used herein can be selected from the bases exemplified below, preferably which includes tert-alkylamine, more preferably DIPEA and triethylamine. The solvent used herein can be selected from the solvents exemplified below, preferably which includes DMF, dichloromethane, chloroform, and THF. The reaction time is generally about 5 minutes to about 48 hours, and preferably about 10 minutes to about 24 hours. The reaction temperature is generally about −78° C. to about 100° C., and preferably about 0° C. to about 100° C.

Process D-2

In compounds according to formula (1) or a pharmaceutically acceptable salt thereof, the compound (d2-2) which has a linker of —OC(O)— or —NR$^Y$C(O)— can be prepared by the following process.

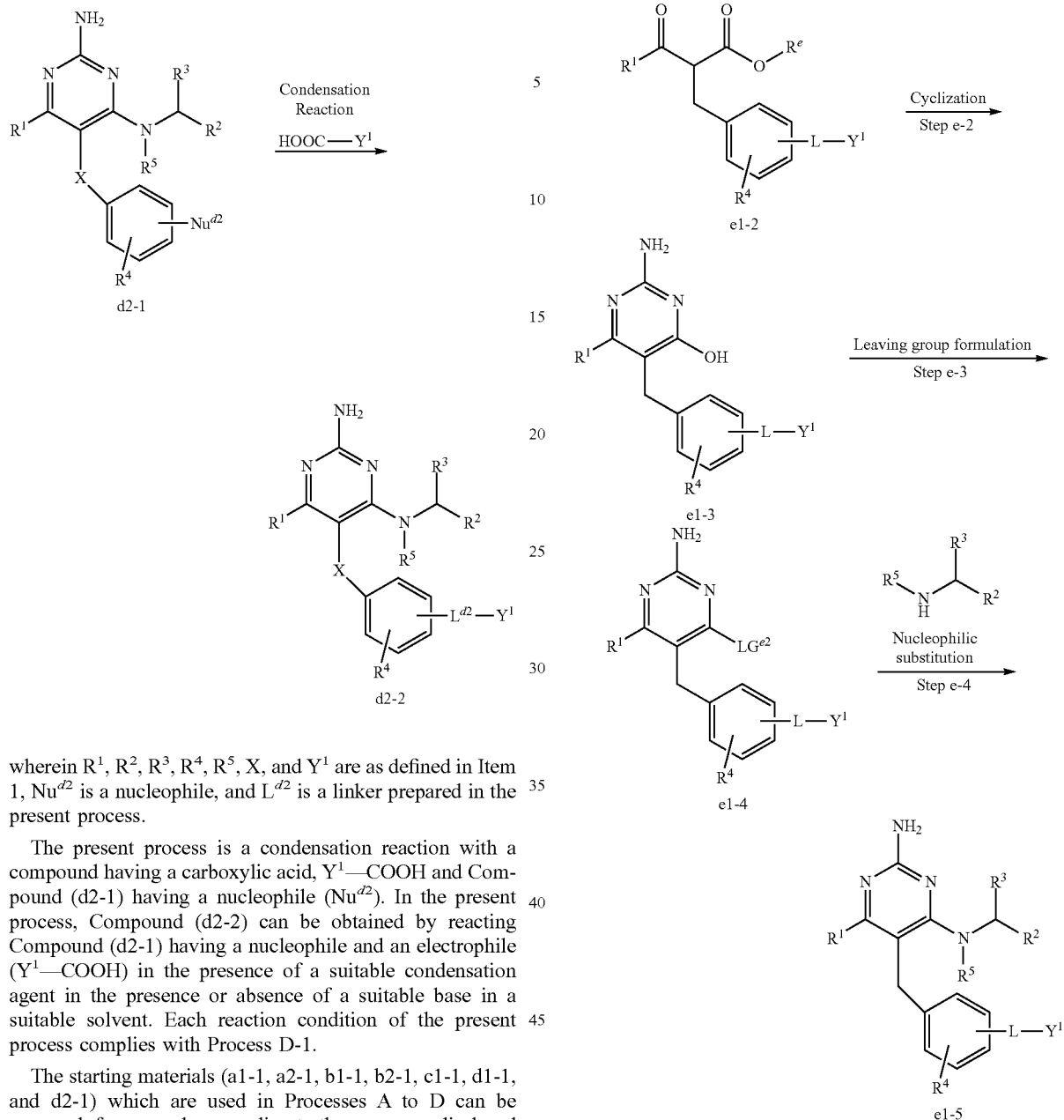

wherein $R^1$, $R^2$, $R^3$, $R^4$, $R^5$, X, and $Y^1$ are as defined in Item 1, $Nu^{d2}$ is a nucleophile, and $L^{d2}$ is a linker prepared in the present process.

The present process is a condensation reaction with a compound having a carboxylic acid, $Y^1$—COOH and Compound (d2-1) having a nucleophile ($Nu^{d2}$). In the present process, Compound (d2-2) can be obtained by reacting Compound (d2-1) having a nucleophile and an electrophile ($Y^1$—COOH) in the presence of a suitable condensation agent in the presence or absence of a suitable base in a suitable solvent. Each reaction condition of the present process complies with Process D-1.

The starting materials (a1-1, a2-1, b1-1, b2-1, c1-1, d1-1, and d2-1) which are used in Processes A to D can be prepared, for example, according to the processes disclosed in WO 2009/067081.

For example, the present compounds according to formula (1) can be prepared by the following process.

Process E-1

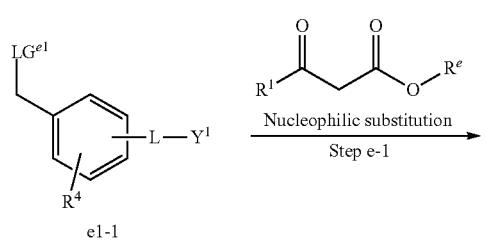

wherein $R^1$, $R^2$, $R^3$, $R^4$, $R^5$, L, and $Y^1$ are as defined in Item 1, $LG^{e1}$ and $LG^{e2}$ are leaving groups, and $R^e$ is $C_{1-6}$ alkyl.

The compound (e1-1) which is the starting material of Step e-1 can be derived as a commercial product or can be prepared according to Processes A to D with the corresponding starting compounds.

Step e-1 to Step e-4 are similar processes disclosed in, for example, WO 2009/067081.

The base used in each step of the above processes should be suitably selected based on the reaction, the starting compound, etc., which includes alkaline bicarbonates such as sodium bicarbonate, and potassium bicarbonate; alkaline carbonate such as sodium carbonate, and potassium carbonate; metallic hydrides such as sodium hydride, and potassium hydride; alkaline metal hydroxides such as sodium hydroxide, and potassium hydroxide; alkaline metal alkoxides such as sodium methoxide, and sodium t-butoxide; organic metal bases such as butyllithium, and lithium diisopropylamide; and organic bases such as triethylamine, diisopropylethylamine, pyridine, 4-dimethylaminopyridine (DMAP), and 1,8-diazabicyclo[5.4.0]undec-7-ene (DBU).

The condensation agent may be those described in Jikken Kagaku Kouza (The Chemical Society of Japan ed., Maruzen) Vol. 22, which includes, for example, phosphates such as diethyl cyanophosphate and diphenylphosphoryl azide; carbodiimides such as 1-ethyl-3-(3-dimethylaminopropyl)-carbodiimide hydrochloride (WSC·HCl) and dicyclohexylcarbodiimide (DCC); combinations of a disulfide such as 2,2'-dipyridyldisulfide and a phosphine such as triphenylphosphine; phosphorus halides such as N,N'-bis(2-oxo-3-oxazolidinyl)phosphinic chloride (BOPCl); combinations of an azodicarboxylate diester such as diethyl azodicarboxylate and a phosphine such as triphenylphosphine; 2-halo-1-lower alkylpyridinium halides such as 2-chloro-1-methylpyridinium iodide; 1,1'-carbonyldiimidazole (CDI); diphenylphosphoryl azide (DPPA); diethylphosphoryl cyanide (DEPC); tetrafluoroborates such as 2-(1H-benzotriazol-1-yl)-1,1,3,3-tetramethyluronium tetrafluoroborate (TBTU) and 2-chloro-1,3-dimethylimidazolidinium tetrafluoroborate (CIB); phosphates such as 2-(1H-benzotriazol-1-yl)-1,1,3,3-tetramethyluronium hexafluorophosphate (HBTU), benzotriazol-1-yloxytris(dimethylamino)phosphonium hexafluorophosphate (BOP), benzotriazol-1-yloxytris(pyrrolidino) phosphonium hexafluorophosphate (PYBOP), and 2-(7-aza-1H-benzotriazol-1-yl)-1,1,3,3-tetramethyluronium hexafluorophosphate (HATU).

The solvent used in each step of the above processes should be suitably selected based on the reaction, the starting compound, etc., which includes, for example, alcohol solvents such as methanol, ethanol, and isopropanol; ketone solvents such as acetone and methylketone; halogenated hydrocarbon solvents such as methylene chloride and chloroform; ether solvents such as tetrahydrofuran (THF) and dioxane; aromatic hydrocarbon solvents such as toluene and benzene; aliphatic hydrocarbon solvents such as hexane and heptane; ester solvents such as ethyl acetate and propyl acetate; amide solvents such as N,N-dimethylformamide (DMF) and N-methyl-2-pyrrolidone; sulfoxide solvents such as dimethylsulfoxide (DMSO); nitrile solvents such as acetonitrile; and water. The solvent used herein may be one of these solvents or a mixture of two or more solvents selected from these solvents. And, if possible in the reaction, an organic base may be used as a solvent used herein.

The "pharmaceutically acceptable salt" includes an acid addition salt and a base addition salt. For example, the acid addition salt includes an inorganic acid salt such as hydrochloride, hydrobromide, sulfate, hydroiodide, nitrate, and phosphate; and an organic acid salt such as citrate, oxalate, phthalate, fumarate, maleate, succinate, malate, acetate, formate, propionate, benzoate, trifluoroacetate, methanesulfonate, benzenesulfonate, para-toluenesulfonate, and camphorsulfonate; and the base addition salt includes an inorganic base salt such as sodium salt, potassium salt, calcium salt, magnesium salt, barium salt, and aluminium salt; and an organic base salt such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, and N,N-dibenzylethylamine. Furthermore, they include a basic or acidic amino acid salt such as arginine, lysine, ornithine, aspartate, and glutamate.

The suitable salts of starting compounds or desired compounds, and pharmaceutically acceptable salts are conventional non-toxic salts, which include an acid addition salt such as an organic acid salt (e.g. acetate, trifluoroacetate, maleate, fumarate, citrate, tartrate, methanesulfonate, benzenesulfonate, formate, para-toluenesulfonate, etc.) and an inorganic acid salt (e.g. hydrochloride, hydrobromide, hydroiodide, sulfate, nitrate, phosphate, etc.); a salt with an amino acid (e.g. arginine, aspartate, glutamate, etc.); a metallic salt such as an alkaline metal salt (e.g. sodium salt, potassium salt, etc.) and an alkaline-earth metal salt (e.g. calcium salt, magnesium salt, etc.); ammonium salt; and an organic base salt (e.g. trimethylamine salt, triethylamine salt, pyridine salt, picoline salt, dicyclohexylamine salt, N,N'-dibenzylethylenediamine salt, etc.); and furthermore, what a skilled person selects suitably.

If it is desirable to fix the compound of the present invention as a salt, when the compound of the present invention is obtained as a salt, it may be purified without further reaction, and when it is obtained in a free form, it may be dissolved or suspended in an appropriate organic solvent and an acid or base may be added therein to form a salt in a general manner.

The compound of the present invention or a pharmaceutically acceptable salt thereof may sometimes exist in form of solvate with water or various solvents. Such solvates are also included in the present invention.

The compound of formula (1) in which any one or more 1H atoms are replaced by $^2$H(D) atoms is also within the scope of the present invention of formula (1).

The present invention encompasses the compound of formula (1) or a pharmaceutically acceptable salt thereof. In addition, the present invention encompasses a hydrate thereof and a solvate thereof such as ethanolate thereof. Furthermore, the present invention encompasses all tautomers, stereoisomers, and crystal forms thereof.

The present compound (1) also includes an optical isomer which is based on chiral center, an atropisomer which is based on axiality caused by intramolecular rotational hindrance or planar-chirality, other stereoisomers, tautomer, and geometric isomer, all possible isomers of which and a mixture thereof are encompassed in the present invention.

The optical isomer mixture of the present compounds can be prepared in a conventional manner. The compounds having an asymmetric structure can be prepared, for example, by using a starting material having an asymmetric center or by introducing an asymmetric structure anywhere along the process. For example, in case of optical isomers, optical isomers can be obtained by using an optically active starting material or resolving a mixture of optical isomers at an appropriate step. In case that the compound of formula (1) or its intermediate has a basic functional group, the optical resolution thereof includes, for example, diastereomer method, wherein the compound is transformed to a salt thereof by reacting with an optically active acid (for example, a monocarboxylic acid such as mandelic acid, N-benzyloxyalanine, and lactic acid; dicarboxylic acid such as tartaric acid, o-diisopropylidene-tartaric acid, and malic acid; or a sulfonic acid such as camphorsulfonic acid and bromocamphorsulfonic acid), in an inert solvent (for example, an alcohols such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof). In case that the compound of formula (1) or its intermediate has an acidic functional group such as carboxyl group, the compound can be also optically resolved after forming its salt with an optically active amine (for example, an organic amine such as 1-phenylethylamine, kinin, quinidine, cinchonidine, cinchonine, and strychnine).

The present compounds of formula (1) and their intermediates can be isolated and purified in a manner known by a skilled person. It includes, for example, extraction, partition, reprecipitation, column chromatography (e.g. silica gel column chromatography, ion exchange column chromatography, and preparative liquid chromatography), and recrystallization.

The solvent for recrystallization used herein includes, for example, an alcohols solvent such as methanol, ethanol, and 2-propanol; an ether solvent such as diethyl ether; an ester solvent such as ethyl acetate; an aromatic hydrocarbon solvent such as benzene and toluene; a ketone solvent such as acetone; a halogenated solvent such as dichloromethane and chloroform; a hydrocarbon solvent such as hexane; an aprotic solvent such as dimethylformamide and acetonitrile; water; and a mixed solvent thereof. As other methods for purification, for example, methods described in Jikken Kagaku Kouza (The Chemical Society of Japan ed., Maruzen) Vol. 1 can be used. And, the structural determination of the present compounds can be easily done by spectroscopic analytical method such as nuclear magnetic resonance method, infrared absorption technique, and circular dichroism spectra analysis, and mass spectrometry, considering the structure of each starting compound.

In addition, each intermediate or each final product in the above preparation processes can be also transformed to another compound of the present invention by suitably modifying its functional group, especially extending various side-chains from amino, hydroxy, carbonyl, halogen, etc.; and optionally making the above-mentioned protection and deprotection if necessary. The modification of functional group and the extension of side-chain can be done by a conventional method (for example, see Comprehensive Organic Transformations, R. C. Larock, John Wiley & Sons Inc. (1999), etc.).

The temperature for forming a salt is selected from the range of generally −50° C. to boiling point of a solvent used herein, preferably 0° C. to the boiling point, and more preferably room temperature to the boiling point. In order to enhance the optical purity, it is desirable to make the temperature raised to around boiling point of a solvent used herein. In collecting a precipitated crystal on a filter, an optional cooling can make the yield increased. The amount of an optically active acid or amine used herein is suitably about 0.5-about 2.0 equivalents against that of the substance compound, preferably around one equivalent. If appropriate, the obtained crystal may be recrystallized in an inert solvent (for example, an alcohols such as methanol, ethanol, and 2-propanol; an ether solvent such as diethyl ether; an ester solvent such as ethyl acetate; a hydrocarbon solvent such as toluene; an aprotic solvent such as acetonitrile; or a mixed solvent thereof) to obtain its highly pure salt thereof. And, if appropriate, the optically-resolved salt can be also treated with an acid or a base to obtain its free form.

Among the starting materials and the intermediates in each preparation process mentioned above, the compounds that are not described in each process are commercially available or can be prepared by a skilled person with a commercial available material in a known manner or a similar manner thereto.

The present invention provides the above-defined compound of formula (1) or a pharmaceutically acceptable salt thereof which is useful as vaccine adjuvant, preferably vaccine adjuvant for cancer vaccine.

In addition, the present invention provides a pharmaceutical composition comprising the above-defined compound of formula (1) or a pharmaceutically acceptable salt thereof in combination with a pharmaceutically acceptable diluent or carrier (hereinafter, referred to as the present pharmaceutical composition).

The present compound or a pharmaceutically acceptable salt thereof may be used as an adjuvant for maintaining or enhancing the immunostimulatory of an active ingredient having an immunostimulating activity.

Namely, the present compound or a pharmaceutically acceptable salt thereof has an activity for inducing or enhancing antigen-specific antibody, specifically antigen-specific IgG, and in more detail Th1-type antigen-specific IgG (e.g. IgG2c).

And, the present compound or a pharmaceutically acceptable salt thereof has an activity for increasing cytotoxic T-lymphocyte (CTL). Or, the present compound or a pharmaceutically acceptable salt thereof has an activity for inducing CTL in mammal or enhancing the CTL induction in mammal.

And, the present compound or a pharmaceutically acceptable salt thereof has an activity for enhancing CD4-positive (i.e., MHC class II-restricted) and/or CD8-positive (i.e., MHC Class I-restricted) T-cell.

And, the present compound or a pharmaceutically acceptable salt thereof has an activity for increasing antigen-specific T-cell.

And, the present compound or a pharmaceutically acceptable salt thereof has an activity for increasing memory T-cell, specifically, CD8-positive effector memory T-cell.

And, the present compound or a pharmaceutically acceptable salt thereof has a character to increase CTL more highly than the same moles of a compound having no PEG structure when administered to mammal.

And, the present compound or a pharmaceutically acceptable salt thereof has an activity for activating immunocompetent cells.

The present pharmaceutical composition may comprise a tumor antigen. As the tumor antigen, tumor antigen protein, or tumor antigen peptide derived from the tumor antigen protein may be used. The tumor antigen peptide used herein includes, preferably the antigen peptide mentioned below, more preferably tumor antigen peptide derived from NY-ESO-1, MAGE-3, WT1, OR7C1, and Her2/neu, and even more preferably tumor antigen peptide derived from WT1. Further, a peptide derived from a neoantigen which results from tumor genetic abnormality may be also used with the compound of the present invention or a pharmaceutically acceptable salt thereof.

In addition, a pharmaceutical composition comprising the present compound or a pharmaceutically acceptable salt thereof and a tumor antigen has an action for inhibiting the growth of tumor which expresses the antigen or the occurrence of tumor which expresses the antigen.

Thus, the present compound or a pharmaceutically acceptable salt thereof is useful as a medicament for treating or preventing cancer by using as a pharmaceutical composition in combination with the tumor antigen mentioned below.

The tumor antigen peptide used herein should not be limited to a particular one, but which may be selected from the peptides and the like disclosed in WO 2014/157692 or WO 2014/157704 A1.

In one embodiment of the tumor antigen peptide, it includes, for example, peptides or pharmaceutically acceptable salts thereof of the following amino acid sequences:

RMFPNAPYL, (SEQ ID NO: 1)

ALLPAVPSL, (SEQ ID NO: 8)

SLGEQQYSV, (SEQ ID NO: 9)

RVPGVAPTL, (SEQ ID NO: 10)

VLDFAPPGA, (SEQ ID NO: 4)

CMTWNQMNL, (SEQ ID NO: 11)

CYTWNQMNL, (SEQ ID NO: 2)

WAPVLDFAPPGASAYGSL, (SEQ ID NO: 3)

CWAPVLDFAPPGASAYGSL, (SEQ ID NO: 12)

WAPVLDFAPPGASAYGSLC, (SEQ ID NO: 13)

CNKRYFKLSHLQMHSRKHTG (SEQ ID NO: 14)

CNKRYFKLSHLQMHSRKH, (SEQ ID NO: 15)

CNKRYFKLSHLQMHSRK, (SEQ ID NO: 16)

KRYFKLSHLQMHSRKH, (SEQ ID NO: 17)
and

TYAGCLSQIF. (SEQ ID NO: 18)

And, peptides or pharmaceutically acceptable salt thereof of the following amino acid sequences of formula (4):

CRMFPNAPYL (SEQ ID NO: 19)
|
CYTWNQMNL (SEQ ID NO: 2)

wherein the bond between C-C is disulfide bond, and formula (5):

C
|
CYTWNQMNL (SEQ ID NO: 2)

wherein the bond between C-C is disulfide bond may be used as a tumor antigen peptide in the present invention.

The tumor antigen peptides can be prepared in a general manner used in peptide chemical field. The synthetic methods include what a reference (Peptide Synthesis, Interscience, New York, 1966; The Proteins, Vol. 2, Academic Press Inc., New York, 1976), etc. discloses.

In another embodiment, the pharmaceutical composition of the present invention may include an antigen. The antigen includes a pathogen-derived antigen, for example, a protein derived from virus or bacterium or its partial protein. And, a complex of the antigen and carrier, etc. is included in the scope of the antigen in the present invention. The complex includes an antigen (including protein and peptide, but not limited thereto) bridged to a protein which is a carrier via a linker which is well known by a skilled person, and an antigen contained in virus-like particle (VLP). Thus, the present compound or a pharmaceutically acceptable salt thereof is useful as a medicament for treating or preventing infection of virus or bacterium by using in combination with the above-mentioned antigen.

Examples of the administration route of the pharmaceutical composition of the present invention includes parenteral administration, specifically intravascular (e.g., intravenous), subcutaneous, intradermal, intramuscular, intratumor, lymph node, and transdermal administrations.

In one embodiment, the pharmaceutical composition of the present invention may comprise a compound of the formula (1) or a pharmaceutically acceptable salt thereof and a pharmaceutically acceptable diluent or carrier.

The drug formulation of the present pharmaceutical composition includes a liquid formulation.

The liquid formulation of the present invention includes an aqueous solution formulation/an aqueous suspension formulation, an oily solution formulation/an oily suspension formulation, a hydrogel formulation, a lipid formulation, and an emulsion formulation.

The aqueous solution formulation or the aqueous suspension formulation includes, for example, a formulation prepared by dissolving or dispersing an antigen (tumor antigen or pathogen-derived antigen), and/or the compound of formula (1) or a pharmaceutically acceptable salt thereof in water.

The oily solution formulation or the oily suspension formulation includes, for example, a formulation prepared by dissolving or dispersing an antigen (tumor antigen or pathogen-derived antigen), and/or the compound of formula (1) or a pharmaceutically acceptable salt thereof in an oily ingredient.

The hydrogel formulation includes, for example, a formulation prepared by dissolving or dispersing an antigen (tumor antigen or pathogen-derived antigen), and/or the compound of formula (1) or a pharmaceutically acceptable salt thereof in water and adding viscosity to the formulation.

The lipid formulation includes, for example, a liposome formulation comprising an antigen (tumor antigen or pathogen-derived antigen), and/or the compound of formula (1) or a pharmaceutically acceptable salt thereof.

The emulsion formulation includes, for example, a formulation including an aqueous solution and an oily composition, which comprises an antigen (tumor antigen or pathogen-derived antigen), and/or the compound of formula (1) or a pharmaceutically acceptable salt thereof.

In another embodiment of the present liquid formulation, the liquid formulation of the present invention includes, an aqueous solution formulation or an aqueous suspension formulation prepared by dissolving or dispersing a tumor antigen, and/or the compound of formula (1) or a pharmaceutically acceptable salt thereof in water; an oily solution formulation or an oily suspension formulation prepared by dissolving or dispersing a tumor antigen, and/or the compound of formula (1) or a pharmaceutically acceptable salt thereof in an oily ingredient; and an emulsion formulation comprising an aqueous solution and an oily composition.

The additive used in the present aqueous solution formulation or aqueous suspension formulation includes, for example, purified water, water for injection, a buffering agent, a pH adjusting agent, a stabilizer, an isotonizing agent, a solubilizer, and a solubilizing agent.

The additive used in the present oily solution formulation or oily suspension formulation includes, for example, a buffering agent, a pH adjusting agent, a stabilizer, an isotonizing agent, animal or vegetable oil and fat, hydrocarbons, a fatty acid, fatty acid esters, a solubilizer, and a solubilizing agent.

The additive used in the present hydrogel formulation includes, for example, purified water, water for injection, a buffering agent, a pH adjusting agent, a stabilizer, an isotonizing agent, a solubilizer, a solubilizing agent, and a thickener.

The additive used in the present liposome formulation includes, for example, purified water, water for injection, a buffering agent, a pH adjusting agent, a stabilizer, an isotonizing agent, a solubilizer, a solubilizing agent, and lipids.

The present emulsion formulation used herein includes oil-in-water emulsion (also referred to as O/W emulsion), water-in-oil emulsion (also referred to as W/O emulsion), water-in-oil-in-water emulsion (also referred to as W/O/W emulsion), and oil-in-water-in-oil emulsion (also referred to as O/W/O emulsion). The present emulsion formulation includes, preferably water-in-oil emulsion (W/O emulsion). The present emulsion formulation can be prepared by emulsifying an aqueous phase and an oil phase in a general manner. An antigen (tumor antigen or pathogen-derived antigen), and/or the compound of formula (1) or a pharmaceutically acceptable salt thereof may be contained in an oil phase and/or an aqueous phase.

The additive used in the present emulsion formulation includes, for example, water, a buffering agent, a pH adjusting agent, a stabilizer, an isotonizing agent, animal or vegetable oil and fat, hydrocarbons, a fatty acid, fatty acid esters, glycerinfatty acid esters, a hydrophilic surfactant, and a lipophilic surfactant, wherein
  the water includes purified water and water for injection,
  the buffering agent includes phosphate and organic acid salt,
  the pH adjusting agent includes hydrochloric acid and sodium hydroxide,
  the stabilizer includes glycerin, propylene glycol, and sulfite,
  the isotonizing agent includes sodium chloride, glucose, sucrose, and mannitol,
  the animal or vegetable oil and fat includes olive oil, soybean oil, and liver oil,
  the hydrocarbon includes liquid paraffin, squalene, and squalane,
  the fatty acid includes oleic acid and myristic acid,
  the fatty acid ester includes ethyl oleate, octyldodecyl myristate, cetyl 2-ethyl-hexanoate, and isopropyl myristate,
  the glycerin fatty acid ester includes medium-chain triglyceride, medium-chain diglyceride, and medium-chain monoglyceride,
  the hydrophilic surfactant includes polyoxyethylene castor oil, polyoxyethylene hydrogenated castor oil, polyoxyethylene sorbitan fatty acid ester, and polysorbates, and
  the lipophilic surfactant includes glyceryl monooleate, glyceryl dioleate, sorbitan monooleate (Span™ 80), sorbitan sesquioleate, sorbitan dioleate, sorbitan trioleate (Span™ 85), PEG-30 dipolyhydroxy stearate, and plant-derived surfactant (saponin, etc.).

Specific composition of additives in the present emulsion formulation used herein includes, but not limited to, an emulsified composition for dilution disclosed in WO 2006/078059, Montanide ISA 51 VG (Seppic), Montanide ISA 720 VG (Seppic), and Incomplete Freund's Adjuvant (IFA).

The present W/O emulsion formulation includes a preparation comprising the compound of formula (1) or a pharmaceutically acceptable salt thereof, ethyl oleate, octyldodecyl myristate, sorbitan monooleate, glyceryl monooleate, polyoxyethylene hydrogenated castor oil 20, glycerin, and sodium dihydrogen phosphate; and a preparation comprising the compound of formula (1) or a pharmaceutically acceptable salt thereof, and Montanide ISA 51 VG.

In the liposome formulation of the present invention, the liposome means a microvesicle composed of lipid multiple layers such as bilayer membrane of amphiphilic lipid molecule (lipid bilayer), which has an internal phase. The preferred lipid multiple layer is lipid bilayer.

The present liposome formulation includes amphiphilic lipid molecule. The amphiphilic lipid molecule includes, preferably one or more "phospholipids". The "phospholipid" includes, for example, phosphatidylcholine, phosphatidylglycerol, phosphatidic acid, phosphatidylethanolamine, phosphatidylserine, phosphatidylinositol, and sphingomyelin. The "phospholipid" includes, preferably phosphatidylcholine, phosphatidylglycerol, phosphatidylethanolamine, sphingomyelin, and phosphatidylserine. The "phospholipid" includes, more preferably phosphatidylcholine, sphingomyelin, and phosphatidylserine.

The fatty acid residue of the "phospholipid" includes, but not limited to, $C_{14-18}$ saturated or unsaturated fatty acid residue, for example, an acyl group derived form a fatty acid such as myristic acid, palmitic acid, stearic acid, oleic acid, and linoleic acid. And, naturally-derived phospholipid such as egg-yolk lecithin and soybean lecithin, and the phospholipid whose unsaturated fatty acid residue is hydrogenated such as hydrogenated egg-yolk lecithin and hydrogenated soybean lecithin (also referred to as hydrogenated soybean phospholipid, or hydrogenated soybean phosphatidylcholine) may be also used herein.

The content of phospholipid per the whole component of the liposome membrane (mole fraction) includes, but not limited to, preferably 30-80%, and more preferably 40-70%.

The liposome internally-including the present compound may contain sterols.

The sterols includes cholesterol, S-sitosterol, stigmasterol, campesterol, brassicasterol, ergosterol, and fucosterol, and preferably cholesterol. The content of sterols per the whole component of the liposome membrane (mole fraction) includes, but not limited to, preferably 0-60%, more preferably 10-50%, and even more preferably 30-50%.

The liposome internally-including the present compound may contain a polymer-modified lipid. The polymer-modified lipid means a lipid modified with polymer. The polymer-modified lipid is denoted by "lipid-polymer". The polymer part in polymer-modified lipid is preferably a hydrophilic polymer, and more preferably hydrophilic polymer where the polymer-terminal which is not bonded to lipid is alkoxylated. The polymer part in polymer-modified lipid is more preferably a hydrophilic polymer where the polymer-terminal which is not bonded to lipid is methoxylated, ethoxylated, or propoxylated. The polymer part in polymer-modified lipid is the most preferably a hydrophilic polymer where the polymer-terminal which is not bonded to lipid is methoxylated. The polymer part in polymer-modified lipid includes, but not limited to, for example, polyethylene glycol, polypropylene glycol, polyvinyl alcohol, polyvinylpyrrolidone, methoxypolyethylene glycol, methoxypolypropylene glycol, methoxypolyvinyl alcohol, methoxypolyvinylpyrrolidone, ethoxypolyethylene glycol, ethoxypolypropylene glycol, ethoxypolyvinyl alcohol, ethoxypolyvinylpyrrolidone, propoxypolyethylene glycol, propoxypolypropylene glycol, propoxypolyvinyl alcohol, and propoxypolyvinylpyrrolidone. The polymer part in polymer-modified lipid includes, preferably polyethylene glycol, methoxypolyethylene glycol, methoxypolypropylene glycol, ethoxypolyethylene glycol, ethoxypolypropylene glycol, propoxypolyethylene glycol, and propoxypolypropylene glycol. The polymer part in polymer-modified lipid includes, more preferably polyethylene glycol, methoxypolyethylene glycol, ethoxypolyethylene glycol, ethoxypolypropylene glycol, and propoxypolyethylene glycol. The polymer part in polymer-modified lipid includes, even more preferably polyethylene glycol and methoxypolyethylene glycol. The polymer part in polymer-modified lipid includes, the most preferably methoxypolyethylene glycol. The molecular weight of polymer part in polymer-modified lipid includes, but not limited to, for example, 100-10000 daltons, preferably 500-8000 daltons, more preferably 1000-7000 daltons, even more preferably 1500-5000 daltons, and the most preferably 1500-3000 daltons. The lipid part of polymer-modified lipid includes, but not limited to, for example, phosphatidylethanolamine and diacylglycerol. The lipid part of polymer-modified lipid includes, preferably phosphatidylethanolamine having $C_{14-18}$ saturated or unsaturated fatty acid residue and diacylglycerol having $C_{14-18}$ saturated or unsaturated fatty acid residue, more preferably phosphatidylethanolamine having $C_{14-18}$ saturated fatty acid residue and diacylglycerol having $C_{14-18}$ saturated fatty acid residue, and even more preferably phosphatidylethanolamine having palmitoyl group or stearoyl group and diacylglycerol having palmitoyl group or stearoyl group. The lipid part of polymer-modified lipid includes, the most preferably distearoylphosphatidylethanolamine.

The content of polymer-modified lipid per the whole component of the liposome membrane (mole fraction) includes, but not limited to, preferably 0-20%, more preferably 1-10%, and even more preferably 2-6%.

The liposome internally-including the present compound may contain a pharmaceutically acceptable additive. The additive includes, for example, an inorganic acid, an inorganic acid salt, an organic acid, an organic acid salt, sugars, a buffering agent, an antioxidant, and polymers. The inorganic acid includes, for example, phosphoric acid, hydrochloric acid, and sulfuric acid. The inorganic acid salt includes, for example, disodium hydrogen phosphate, sodium chloride, ammonium sulfate, and magnesium sulfate. The organic acid includes, for example, citric acid, acetic acid, succinic acid, and tartaric acid. The organic acid salt includes, for example, sodium citrate, sodium acetate, disodium succinate, and sodium tartrate. The sugar includes, for example, glucose, sucrose, mannitol, sorbitol, and trehalose. The buffering agent includes, for example, L-arginine, L-histidine, trometamol (trishydroxymethylaminomethane, Tris), and a salt thereof. The antioxidant includes, for example, sodium sulfite, L-cysteine, sodium thioglycolate, sodium thiosulfate, ascorbic acid, and tocopherol. The polymers includes, for example, polyvinyl alcohol, polyvinylpyrrolidone, carboxy vinyl polymer, and carboxymethylcellulose sodium.

In the present oily suspension formulation, an antigen (tumor antigen or pathogen-derived antigen) and/or the compound of formula (1) or a pharmaceutically acceptable salt thereof may be contained in an oily ingredient, in solution state or dispersion state, or in the both state. The additive used in the present oily suspension formulation includes, for example, a buffering agent, a pH adjusting agent, a stabilizer, an isotonizing agent, animal or vegetable oil and fat, hydrocarbons, a fatty acid, fatty acid esters, a solubilizer and a solubilizing agent, wherein the buffering agent includes phosphate and organic acid salt, the pH adjusting agent includes hydrochloric acid and sodium hydroxide, the stabilizer includes glycerin, propylene glycol, and sulfite, the isotonizing agent includes sodium chloride, glucose, sucrose, and mannitol, the animal or vegetable oil and fat includes olive oil, soybean oil, and liver oil, the hydrocarbons includes liquid paraffin, squalene, and squalane, the fatty acid includes oleic acid and myristic acid, the fatty acid esters includes ethyl oleate, octyldodecyl myristate, cetyl 2-ethyl-hexanoate, isopropyl myristate, sucrose fatty acid ester, glycerin fatty acid ester, sorbitan fatty acid ester, and propylene glycol fatty acid ester, the solubilizer or solubilizing agent includes glycerin, propylene glycol, macrogol, and ethanol.

The present hydrogel formulation includes, for example, a formulation prepared by dissolving or dispersing an antigen (tumor antigen or pathogen-derived antigen), and/or the compound of formula (1) or a pharmaceutically acceptable salt thereof in water and adding viscosity to the formulation. The additive used in the present hydrogel formulation includes, for example, purified water, water for injection, a buffering agent, a pH adjusting agent, a stabilizer, an isotonizing agent, a solubilizer, a solubilizing agent, and a thickener, wherein the buffering agent includes phosphate and organic acid salt, the pH adjusting agent includes hydrochloric acid and sodium hydroxide, the stabilizer includes glycerin, propylene glycol, and sulfite, the isotonizing agent includes sodium chloride, glucose, sucrose, and mannitol, the solubilizer or solubilizing agent includes glycerin, propylene glycol, macrogol, and ethanol, the thickener includes carmellose sodium, poloxamers, and povidones.

The compound of formula (1), or a pharmaceutically acceptable salt thereof, or a pharmaceutical composition of the present invention may be used in combination with further another medicament (also referred to as combination drug) besides the above tumor antigen.

In an embodiment, the compound of formula (1), or a pharmaceutically acceptable salt thereof, or a pharmaceutical composition of the present invention may be administered in combination with an "immunomodulator", besides the above-mentioned tumor antigen. As used herein, the term "immunomodulator" means any agent that controls transmission of costimulatory signals generated during T cell activation by antigen-presenting cells by interacting with molecules which are involved in the transmission of the costimulatory signals and are present on the antigen-presenting cells and/or T cells, as well as any agent that directly or indirectly controls function of molecules involved in establishment of immune tolerance (immunosuppression) in the immune system. Since a tumor antigen peptide is effective for increasing tumor-reactive CTLs in a tumor, it is potentially useful as an agent for coadministration with an immunomodulator, for lowering a necessary dose of an immunomodulator or reducing adverse event caused by an immumonodulator. Thus, the present disclosure provides, through the use of a WT1 antigen peptide in combination with an immumomodulator, patients with a therapy having improved efficacy and safety.

The "immunomodulator" can be an agent in the form of an antibody, a nucleic acid, a protein, a peptide, or a small molecule, but is not limited thereto. The "antibody" as the "immunomodulator" includes an antibody fragment. Examples of the antibody fragment include heavy and light chain variable regions of an antibody (VH and VL), F(ab')2, Fab', Fab, Fv, Fd, sdFv, and scFV. The "protein" as the "immunomodulator" means any protein other than antibodies. Examples of the "immunomodulator" include, for example, immune checkpoint inhibitors, costimulatory molecule agonists, immune activating agents, and small molecule inhibitors.

The "immune checkpoint inhibitor" inhibits immunosuppressive effect induced by cancer cells or antigen presenting cells. Examples of the immune checkpoint inhibitor include, but not limited to, agents against a molecule selected from the group consisting of: (1) CTLA-4 (e.g., ipilimumab and tremelimumab); (2) PD-1 (e.g., nivolumab, pembrolizumab, AMP-224, AMP-514 (MEDI0680), and pidilizumab (CT-011)); (3) LAG-3 (e.g., IMP-321 and BMS-986016); (4) BTLA; (5) KIR (e.g., IPH2101); (6) TIM-3 (e.g., LY3321367 and CA-327); (7) PD-L1 (e.g., durvalumab (MEDI4736), MPDL3280A, BMS-936559, avelumab (MSB0010718C), BMS-1001, BMS-1116, and CA-170, CA-327); (8) PD-L2; (9) B7-H3 (e.g., MGA-271); (10) B7-H4; (11) HVEM; (12) GAL9; (13) CD160; (14) VISTA (e.g., onvatilimab (JNJ-61610588), HMBD-002, and CA-170); (15) BTNL2; (16) TIGIT; (17) PVR; (18) BTN1A1; (19) BTN2A2; (20) BTN3A2 (Nat Rev Drug Discov. 2013; 12: 130-146; Nikkei Medical Cancer Review 2014; 9; Nat Rev Immunol. 2014; 14: 559-69); (21) CSF1-R; (22) VSIG-3; (23) CD112; (24) CD112R; and (25) CD96.

The "costimulatory molecule agonist" enhances T cell activation by transmission of an auxiliary signal via a costimulatory molecule on the T cells and/or antigen-presenting cells, and attenuates the immunosuppressive effect of cancer cells or antigen presenting cells. Examples of the costimulatory molecule agonist include, but not limited to, agents against a molecule selected from the group consisting of: (1) 4-1BB; (2) 4-1BB-L; (3) OX40; (4) OX40-L; (5) GITR; (6) CD28; (7) CD40; (8) CD40-L; (9) ICOS; (10) ICOS-L; (11) LIGHT; (12) CD27; and (13) DNAM-1.

The "immune activating agent" efficiently stimulates killer T cells in the lymph nodes by directly or indirectly activating immune cells such as T cells and dendritic cells. Examples of the immune activating agent include, but not limited to, Toll-like receptor (TLR) agonists, stimulator of interferon genes (STING) agonists, cytokines, and agents against heat shock protein (HSP).

Examples of the "Toll-like receptor (TLR) agonist" include, but not limited to, TLR1/2 agonists, TLR2 agonists, TLR3 agonists (e.g., PolyI:C), TLR4 agonists (e.g., S-type lipopolysaccharide, paclitaxel, lipid A, and monophosphoryl lipid A), TLR5 agonists (e.g., flagellin), TLR6/2 agonists (e.g., MALP-2), TLR7 agonist, TLR7/8 agonists (e.g., gardiquimod, imiquimod, loxoribine, and resiquimod (R848)), TLR7/9 agonists (e.g., hydroxychloroquine sulfate), TLR8 agonists (e.g., motolimod (VTX-2337)), TLR9 agonists (e.g., CpG-ODN), and TLR11 agonists (e.g., profilin).

Examples of the "cytokine" include, but not limited to, IL-1a, IL-1p, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (INF)-α, INF-β, INF-γ, SCF, GM-CSF, G-CSF, M-CSF, erythropoietin, thrombopoietin, macrophage inflammatory protein (MIP), and monocyte chemoattractant protein (MCP).

Examples of the "heat shock protein (HSP)" include, but not limited to, HSP70, HSP90, HSP90a, HSP903, HSP105, HSP72, and HSP40. Agents against a heat shock protein include HSP inhibitors. Examples of inhibitors to HSP90 include, but not limited to, tanespimycin (17-AAG), luminespib (AUY-922, NVP-AUY922), alvespimycin (17-DMAG) hydrochloride, ganetespib (STA-9090), BIIB021, onalespib (AT13387), geldanamycin, NVP-BEP800, SNX-2112 (PF-04928473), PF-4929113 (SNX-5422), KW-2478, XL888, VER155008, VER-50589, CH5138303, VER-49009, NMS-E973, PU-H71, HSP990 (NVP-HSP990), and KNK437.

Examples of the "small molecule inhibitor" include, but not limited to, histone deacetylase inhibitors, histone demethylase inhibitors, histone acetyltransferase inhibitors, histone methyltransferase inhibitors, DNA methyltransferase inhibitors, anthracycline antibiotics, platinum agents, MAPK inhibitors, β-catenin inhibitors, STAT3 inhibitors, NF-kB inhibitors, JAK inhibitors, mTOR inhibitors, IDO inhibitors, COX-2 inhibitors, CXCR4 inhibitors, and arginase inhibitors.

Examples of the "histone deacetylase inhibitor" include, but not limited to, vorinostat (SAHA, MK0683), entinostat (MS-275), panobinostat (LBH589), trichostatin A (TSA), mocetinostat (MGCD0103), BG45, BRD73954, belinostat (PXD101), romidepsin (FK228, depsipeptide), 4SC-202, HPOB, LMK-235, CAY10603, tasquinimod, TMP269, nexturastat A, rocilinostat (ACY-1215), RGFP966, RG2833 (RGFP109), scriptaid, tubastatin A, pracinostat (SB939), CUDC-101, M344, PCI-34051, dacinostat (LAQ824), tubastatin A hydrochloride, abexinostat (PCI-24781), CUDC-907, AR-42, sodium phenylbutyrate, resminostat, tubacin, quisinostat (JNJ-26481585) dihydrochloride, MC1568, givinostat (ITF2357), droxinostat, chidamide (C S055, HBI-8000), CHR-2485, CHR-3996, DAC-060, FRM-0334 (EVP-0334), MGCD-290, CXD-101 (AZD-9468), CG200745, arginine butyrate, sulforaphane, SHP-141, CUDC-907, YM753 (OBP-801), sodium valproate, apicidin, and CI994 (tacedinaline).

Examples of the "histone demethylase inhibitor" include, but not limited to, GSK J4 HCl, OG-L002, JIB-04, IOX1, SP2509, ORY-1001 (RG-6016), GSK J1, ML324, and GSK-LSD1 2HCl.

Examples of the "histone acetyltransferase inhibitor" include, but not limited to, C646, MG149, remodelin, and anacardic acid.

Examples of the "histone methyltransferase inhibitor" include, but not limited to, pinometostat (EPZ5676), EPZ005678, GSK343, BIX01294, tazemetostat (EPZ6438), 3-deazaneplanocin A (DZNeP) HCl, UNC1999, MM-102, SGC0946, entacapone, EPZ015666, UNC0379, EI1, MI-2 (menin-MLL inhibitor), MI-3 (menin-MLL inhibitor), PFI-2, GSK126, EPZ04777, BRD4770, GSK-2816126, and UNC0631.

Examples of the "DNA methyltransferase inhibitor" include, but not limited to, decitabine, azatidine, RG108, thioguanine, zebularine, SGI-110, CC-486, SGI-1027, lomeguatrib, and procainamide hydrochloride.

The "anthracycline antibiotic" is intercalated between DNA strands to inhibit DNA relaxation. Examples of the anthracycline antibiotic include, but not limited to, doxorubicin, liposomal doxorubicin, daunorubicin, pirarubicin, epirubicin, idarubicin, aclarubicin, amrubicin, aloin, and mitoxantrone.

Examples of the "platinum agents" include, but not limited to, cisplatin, carboplatin, miboplatin, nedaplatin, satraplatin (JM-126), oxaliplatin (ELOXATIN), triplatin tetranitrate, and DDS formulations thereof.

Examples of the "MAPK inhibitor" include, but not limited to, SB203580, doramapimod (BIRB796), SB202190 (FHPI), LY2228820, VX-702, SB239063, pexmetinib (ARRY-614), PH-797804, VX-745, and TAK-715.

Examples of the "β-catenin inhibitor" include, but not limited to, XAV-939, ICG-001, IWR-1-endo, Wnt-C59 (C59), LGK-974, KY02111, IWP-2, IWP-L6, WIKI4, and FH535.

Examples of the "STAT3 inhibitor" include, but not limited to, S3I-201, Stattic, niclosamide, nifuroxazide, napabucasin (BB1608), cryptotanshinone, HO-3867, WHI-P154, FLLL32, STA-21, WP1066, and SH-4-54.

Examples of the "NF-kB inhibitor" include, but not limited to, QNZ (EVP4593), sodium 4-aminosalicylate, JSH-23, phenethyl caffeate, sodium salicylate, andrographolide, and SC75741.

Examples of the "JAK inhibitor" include, but not limited to, ruxolitinib (INCB018424), tofacitinib (CP-690550) citrate, AZD1480, fedratinib (SAR302503, TG101348), AT9283, tyrphostin B42 (AG-490), momelotinib (CYT387), tofacitinib (CP-690550, tasocitinib), WP1066, TG101209, gandotinib (LY2784544), NVP-BSK805 2HCl, baricitinib (LY3009104, INCB02850), AZ960, CEP-33779, pacritinib (SB1518), WHI-P154, XL019, S-ruxolitinib (INCB018424), ZM39923 HCl, decernotinib (VX-509), cerdulatinib (PRT062070, PRT2070), filgotinib (GLPG0634), FLLL32, peficitinib (ASP015K, JNJ-54781532), GLPG0634 analogue, Go6976, and Curcumol.

Examples of the "mTOR inhibitor" include, but not limited to, sirolimus (rapamycin), deforolimus (AP23573, MK-8669), everolimus (RAD-001), temsirolimus (CCI-779, NSC683864), zotarolimus (ABT-578), biolimus A9 (umirolimus), AZD8055, KU-0063794, voxtalisib (XL765, SAR245409), MHY1485, dactolisib (BEZ235, NVP-BEZ235), PI-103, and torkinib (PP242).

Examples of the "IDO inhibitor" include, but not limited to, NLG919, INCB024360 analog, indoximod (NLG-8189), and epacadostat (INCB024360).

Examples of the "COX-2 inhibitor" include, but not limited to, valdecoxib, rofecoxib, carprofen, celecoxib, lumiracoxib, tolfenamic acid, nimesulide, niflumic acid, asaraldehyde, lornoxicam, sodium meclofenamate, amfenac sodium hydrate, diclofenac sodium, ketoprofen, ketorolac, naproxen sodium, indomethacin, ibuprofen, aspirin, mefenamic acid, bromfenac sodium, oxaprozin, zaltoprofen, and nepafenac.

Examples of the "CXCR4 inhibitor" include, but not limited to, WZ811, plerixafor (AMD3100), and plerixafor 8HCl (AMD3100 8HCl).

The compound of formula (1), or a pharmaceutically acceptable salt thereof, or the composition as described herein may also be used in combination with one or more drugs selected from the group consisting of "hormone therapy agent", "immunotherapeutic agent", "biopharmaceutical", "cell growth factor", "cell growth factor inhibitor", "cell growth factor receptor inhibitor", "radiotherapeutic agent", "auxiliary agent", and "chemotherapeutic agent". For example, one to five drugs, one to three drugs, or one drug selected from the above group of drugs may be used in combination with the peptide or the compound of formula (1), or a pharmaceutically acceptable salt thereof, or a combination thereof as described herein.

Examples of the "hormone therapy agent" include adrenal cortical hormone agents (e.g., steroidal anti-inflammatory agents, estrogen preparations, progesterone preparations, and androgen preparations), anti-estrogen agents, estrogen-controlling agents, estrogen synthesis inhibitors, anti-androgen agents, androgen-controlling agents, androgen synthesis inhibitors, LH-RH agonist preparations, LH-RH antagonist preparations, aromatase inhibitors, steroid-lactonase inhibitors, contraceptive pills, retinoids, and agents which delay metabolism of a retinoid.

Examples of the "hormone therapy agent" include fosfestrol, diethylstilbestrol, fluoxymesterol, chlorotrianisene, methyl testosterone, medroxyprogesterone acetate, megestrol acetate, chlormadinone acetate, cyproterone acetate, danazol, allylestrenol, gestrinone, mepartricin, raloxifene, ormeloxifene, levormeloxifene, tamoxifen citrate, toremifene citrate, iodoxyfene, pill formulations, mepitiostane, testololactone, aminoglutethimide, goserelin acetate, buserelin, leuprorelin, leuprolide, droloxifene, epitiostanol, ethinylestradiol sulfonate, estramustine, fadrozole hydrochloride, anastrozole, terorazole, ketoconazole, letrozole, exemestane, vorozole, formestane, exemestane, flutamide, bicalutamide, nilutamide, enzalutamide, mifepristone, finasteride, dexamethasone, prednisolone, betamethasone, triamcinolone, abiraterone, liarozole, bexarotene, and DN101.

Examples of the "immunotherapeutic agent" include picibanil, krestin, sizofiran, lentinan, ubenimex, interferon (IL)-α, interferon (IL)-β, interferon (IL)-γ, interleukin, macrophage colony stimulating factor, granulocyte-colony stimulating factor, erythropoietin, lymphotoxin, BCG vaccine, *Corynebacterium parvum*, levamisole, polysaccharide K, procodazole, anti-CTLA4 antibody, anti-PD-1 antibody, and TLR agonists (e.g., TLR7 agonists, TLR8 agonists, TLR9 agonists).

Examples of the "biopharmaceutical" include, but not limited to, interleukin-2 (aldesleukin), interferon-α, interferon-β, interferon-γ, erythropoietin (EPO), granulocyte-colony stimulating factor (filgrastim), granulocyte-macrophage-colony stimulating factor (sargramostim), IL13-PE38QQR, Bacille Calmette-Guerin, levamisole, octreotide, CPG7909, Provenge, GVAX, Myvax, Favld, lenalidomide, trastuzumab, rituximab, gemtuzumab ozogamicin, alemtuzumab, endostatin, ibritumomab tiuxetan, tositumomab, cetuximab, zanolimumab, ofatumumab, HGS-ETR1, pertuzumab, M200, SGN-30, matuzumab, adecatumumab, denosumab, zalutumumab, MDX-060, nimotuzumab, MORAb-003, Vitaxin, MDX-101, MDX-010, DPC4 antibodies, NF-1 antibodies, NF-2 antibodies, Rb antibodies, p53 antibodies, WT1 antibodies, BRCA1 antibodies, BRCA2 antibodies, ganglioside (GM2), prostate specific antigens (PSA), α-fetoprotein (AFP), carcinoembryonic antigens (CEA), melanoma-associated antigens (MART-1, gap100, MAGE 1,3 tyrosine), papilloma virus E6 and E7 fragments, and DDS formulations thereof.

Regarding the "cell growth factor", "cell growth factor inhibitor" and "cell growth factor receptor inhibitor", cell growth factor may be any agent that promotes cell proliferation. For example, a cell growth factor may be a peptide having a molecular weight of not more than 20,000 which can bind to a receptor to function at a low concentration.

Examples of the "cell growth factor" include, but not limited to, epidermal growth factor (EGF), insulin-like growth factor (IGF (e.g., insulin, IGF-1, and IGF-2)), transforming growth factor (TGF (e.g., TGF-α and TGF-β)), nerve growth factor (NGF), brain-derived neurotrophic factor (BDNF), vascular endothelial growth factor (VEGF), colony stimulating factor (CSF (e.g., granulocyte-colony stimulating factor (G-CSF)), granulocyte-macrophage-colony stimulating factor (GM-CSF)), platelet-derived growth factor (PDGF), erythropoietin (EPO), fibroblast growth factor (FGF (e.g., acidic FGF, basic FGF, keratinocyte growth factor (KGK), and FGF-10)), hepatocyte growth factor (HGF), heregulin, and angiopoietin. The term "cell growth factor" is synonymous with the term "growth factor".

Examples of the "cell growth factor inhibitor" include, but not limited to, epidermal growth factor inhibitors (EGF inhibitors), insulin-like growth factor inhibitors (IGF inhibitors), nerve growth factor inhibitors (NGF inhibitors), brain-derived neurotrophic factor inhibitors (BDNF inhibitors), vascular endothelial cell growth factor inhibitors (VEGF inhibitors), colony stimulating factor inhibitors (CSF inhibitors), platelet-derived growth factor inhibitors (PDGF inhibitors), erythropoietin inhibitors (EPO inhibitors), fibroblast growth factor inhibitors (FGF inhibitors), hepatocyte growth factor inhibitors (HGF inhibitors), heregulin inhibitors, and angiopoietin inhibitors. The term "cell growth factor inhibitor" is synonymous with the term "growth factor inhibitor".

Examples of the "cell growth factor receptor inhibitor" include, but not limited to, epidermal growth factor receptor inhibitors (EGFR inhibitors), insulin-like growth factor receptor inhibitors (IGFR inhibitors), nerve growth factor receptor inhibitors (NGFR inhibitors), brain-derived neurotrophic factor receptor inhibitors (BDNFR inhibitors), vascular endothelial cell growth factor receptor inhibitors (VEGFR inhibitors), colony stimulating factor inhibitors (CSF inhibitors), platelet-derived growth factor receptor inhibitors (PDGFR inhibitors), erythropoietin receptor inhibitors (EPOR inhibitors), fibroblast growth factor receptor inhibitors (FGFR inhibitors), hepatocyte growth factor receptor inhibitors (HGFR inhibitors), heregulin receptor inhibitors, and angiopoietin receptor inhibitors. The term "cell growth factor receptor inhibitor" is synonymous with the term "growth factor receptor inhibitor".

Examples of the "radiotherapeutic agent" include, but not limited to, radioactive materials and radiosensitizers.

The "auxiliary agent" is an agent used together with an anticancer agent for suppressing a side effect or vomiting caused by the anticancer agent. Examples of the "auxiliary agent" include, but not limited to, aprepitant, ondansetron, lorazepam, dexamethasone, diphenhydramine, ranitidine, cimetidine, ranitidine, famotidine, cimetidine, Procrit, epoetin alfa, filgrastim, oprelvekin, leucovorin, and granulocyte-macrophage-colony stimulating factor (GM-CSF).

Examples of the "chemotherapeutic agent" include, but not limited to, alkylating agents, platinum agents, antimetabolites, topoisomerase inhibitors, DNA intercalators, antimitotic agents, antitumor antibiotics, plant-derived anticancer agents, epigenetic drugs, immunomodulators, molecular targeted drugs, angiogenesis inhibitors, and other chemotherapeutic agents. Some typical examples of chemotherapeutic agent are listed below.

Examples of the "alkylating agent" include, but not limited to, nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, procarbazine, ranimustine, estramustine sodium phosphate, triethylenemelamine, carmustine, lomustine, streptozocin, pipobroman, etoglucid, altretamine, ambamustine, dibrospidium hydrochloride, fotemustine, prednimustine, bendamustine, uramustine, semustine, pumitepa, ribomustin, temozolomide, treosulfan, trofosfamide, zinostatin stimalamer, adozelesin, cystemustine, bizelesin, mechlorethamine, uracil mustard, streptozocin, trabectedin, becaterin, chlormethine, mannosulfan, triaziquone, procarbazine, canfosfamide, nitrosoureas, and DDS formulations thereof.

Examples of the "platinum agents" include, but not limited to, cisplatin, carboplatin, miboplatin, nedaplatin, satraplatin, oxaliplatin, triplatin tetranitrate, and DDS formulations thereof.

Examples of the "antimetabolite" include, but not limited to, antifolates, pyrimidine metabolism inhibitors, purine metabolism inhibitors, ribonucleotide reductase inhibitors, and nucleotide analogs.

Examples of the "antimetabolite" include, but not limited to, mercaptopurine, 6-mercaptopurine riboside, thioinosine, methotrexate, pemetrexed, eoshitabin, enocitabine, cytarabine, cytarabine ocfosfate, ancitabine hydrochloride, 5-FU agents (e.g., fluorouracil, Carzonal, Bennan, Lunachol, Lunapon, tegafur, tegafur-uracil, tegafur-gimeracil-oteracil potassium (TS-1), UFT, doxifluridine, carmofur, gallocitabine, emitefur, and capecitabine), aminopterin, nelarabine, leucovorin calcium, Tabloid, butocine, folinate calcium, levofolinate calcium, cladribine, emitefur, fludarabine, gemcitabine, hydroxycarbamide, pentostatin, piritrexim, idoxuridine, mitoguazone, tiazofurine, ambamustine, bendamustine, floxuridine, nelarabine, leucovorin, hydroxyurea, thioguanine, asparaginase, bortezomib, raltitrexed, clofarabine, enocitabine, sapacitabine, azacytidine, sulfadiazine, sulfamethoxazole, trimethoprim, Liproxstatin-1, D4476, Xanthohumol, Epacadostat (INCB024360), Vidofludimus, P7C3, GMX1778 (CHS828), NCT-501, SW033291, Ro61-8048, and DDS formulations thereof.

Examples of the "topoisomerase inhibitor" include, but not limited to, doxorubicin, daunorubicin, epirubicin, idarubicin, anthracenedione, mitoxantrone, mitomycin C, bleomycin, dactinomycin, plicatomycin, irinotecan, camptothecin, rubitecan, belotecan, etoposide, teniposide, topotecan, amsacrine, and DDS formulations thereof.

Examples of the "DNA intercalator" include, but not limited to, proflavine, doxorubicin (adriamycin), daunorubicin, dactinomycin, thalidomide, and DDS formulations thereof.

Examples of the "antimitotic agent" include, but not limited to, paclitaxel, paclitaxel derivatives (e.g., DHA paclitaxel, paclitaxel polyglutamate, nab-paclitaxel, micellar paclitaxel, 7α-glucosyloxyacetylpaclitaxel, and BMS-275183), docetaxel, vinorelbine, vincristine, vinblastine, vindesine, vinzolidine, etoposide, teniposide, ixabepilone, larotaxel, ortataxel, tesetaxel, ispinesib, colchicine, vinflunine, and DDS formulations thereof.

Examples of the "antitumor antibiotic" include, but not limited to, actinomycin D, actinomycin C, mitomycin C, chromomycin A3, mithramycin A, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, amrubicin hydrochloride, neocarzinostatin, zinostatin stimalamer, mithramycin, sarkomycin, carzinophilin, mitotane, zorubicin hydrochloride, mitoxantrone hydrochloride, idarubicin hydrochloride, liposomal doxorubicin, and DDS formulations thereof.

Examples of the "plant-derived anticancer agent" include, but not limited to, irinotecan, nogitecan, etoposide, etoposide phosphate, eribulin, sobuzoxane, vinblastine sulfate, vincristine sulfate, vindesine sulfate, teniposide, paclitaxel, paclitaxel injection, docetaxel, DJ-927, vinorelbine, topotecan, and DDS formulations thereof.

Examples of the "epigenetic drug" include, but not limited to, DNA methylation inhibitors, histone deacetylase (HDAC) inhibitors, DNA methyl transferase (DNMT) inhibitors, histone deacetylase activators, histone demethylase inhibitors, and methylated nucleotides.

Specific examples of the "epigenetic drug" include, but not limited to, vorinostat, belinostat, mocetinostat (MGCD0103), entinostat (SNDX-275), romidepsin, azacytidine, decitabine, GSK2879552 2H1, SGC707, ORY-1001 (RG-6016), PFI-4, SirReal2, GSK2801, CPI-360, GSK503, AMI-1, CPI-169, and DDS formulations thereof.

Examples of the "immunomodulator" include, but not limited to, thalidomide, lenalidomide, pomalidomide, and DDS formulations thereof.

The "molecular targeted drug" can be a small molecule or an antibody. Examples of the "molecular targeted drug" include, but not limited to, kinase inhibitors, proteasome inhibitors, monoclonal antibodies, mTOR inhibitors, TNF inhibitors, and T-cell inhibitors.

Examples of the "kinase inhibitor" include, but not limited to, tyrosine kinase inhibitors, serine/threonine kinase inhibitors, Raf kinase inhibitors, cyclin-dependent kinase (CDK) inhibitors, and mitogen-activated protein kinase (MEK) inhibitors.

Specific examples of the "kinase inhibitor" include, but not limited to, imatinib, gefitinib, erlotinib, afatinib, dasatinib, bosutinib, vandetanib, sunitinib, axitinib, pazopanib, lenvatinib, lapatinib, nintedanib, nilotinib, crizotinib, ceritinib, alectinib, ruxolitinib, tofacitinib, ibrutinib, sorafenib, vemurafenib, dabrafenib, palbociclib, trametinib, regorafenib, cedivanib, lestaurtinib, bandetinib, vatalanib, seliciclib, tivantinib, canertinib, pelitinib, tesevatinib, cediranib, motesanib, midostaurin, foretinib, cabozantinib, selumetinib, neratinib, volasertib, saracatinib, enzastaurin, tandutinib, semaxanib, alvocidib, ICR-62, AEE788, PD0325901, PD153035, TK787, amcasertib (BBI503), E6201, E7050, and DDS formulations thereof.

Examples of the "proteasome inhibitor" include, but not limited to, bortezomib, carfilzomib, and DDS formulations thereof.

Examples of the "monoclonal antibody" include, but not limited to, anti-CD22 antibodies, anti-CD20 antibodies, anti-CD25 antibodies, anti-CD30 antibodies, anti-CD33 antibodies, anti-CD5 antibodies, anti-CD52 antibodies, anti-epidermal growth factor receptor antibodies (EGFR antibodies), anti-vascular endothelial cell growth factor antibodies (VEGF antibodies), anti-TNF-α antibodies, anti-IL-1 receptor antibodies, anti-IL-2 receptor antibodies, anti-IL-5 receptor antibodies, anti-IL-6 receptor antibodies, anti-HER2 antibodies, anti-IgE antibodies, anti-IgG antibodies, anti-RS virus antibodies, anti-CCR4 antibodies, anti-cytotoxic T lymphocyte-associated antigen 4 (CTLA-4, CD152) antibodies, anti-PD-1 antibodies, anti-receptor activator of nuclear factor κB ligand (RANKL) antibodies, anti-c-Met antibodies, and anti-CXCR4 antibodies.

Specific examples of the "monoclonal antibody" include, but not limited to, ibritumomab tiuxetan, rituximab, cetuximab, infliximab, basiliximab, brentuximab vedotin, tocilizumab, trastuzumab, bevacizumab, omalizumab, mepolizumab, gemtuzumab, ozogamicin, palivizumab, ranibizumab, certolizumab, ocrelizumab, mogamulizumab, eculizumab, pertuzumab, alemtuzumab, inotuzumab, panitumumab, ofatumumab, golimumab, adalimumab, ramucirumab, nivolumab, anakinra, denosumab, ipilimumab, pembrolizumab, matuzumab, farletuzumab, MORAb-004, MORA-b009, and DDS formulations thereof.

Examples of the "mTOR inhibitor" include, but not limited to, everolimus (RAD001), rapamycin (sirolimus), AZD8055, temsirolimus (CCI-779, NSC683864), KU-0063794, voxtalisib (XL-765, SAR245409), MHY1485, dactolisib (BEZ235), PI-103, torkinib (PP242), ridaforolimus (deforolimus, MK-8669), INK-128 (MLN0128), Torin1, omipalisib (GSK2126458, GSK458), OSI-027, PF-04691502, apitolisib (GDC-0980, RG7422), GSK1059615, gedatolisib (PF-05212384, PKI-587), WYE-132, PP121, WYE-354, AZD2014, Torin2, WYE-687, CH5132799, WAY-600, ETP-46464, GDC-0349, XL388, zotarolimus (ABT-578), tacrolimus (FK506), BGT226 (NVP-BGT226), Palomid 529 (P529), chrysophanic acid, and DDS formulations thereof.

Examples of the "TNF inhibitor" include, but not limited to, etanercept, lenalidomide (CC-5013), pomalidomide, thalidomide, necrostatin-1, and QNZ (EVP4593).

Examples of the "T-cell inhibitor" include, but not limited to, abatacept.

Examples of the "angiogenesis inhibitor" include, but not limited to, CM101, IFN-α, IL-12, platelet factor-4, suramin, semaxanib, thrombospondin, VEGFR antagonists, combinations of an angiostatic steroid and heparin, cartilage-derived angiogenesis inhibitors, matrix metalloproteinase inhibitors, batimastat, marimastat, angiostatin, endostatin, 2-methoxyestradiol, tecogalan, thrombospondin, αVβ3 inhibitors, linomide, ADH-1, E7820, and DDS formulations thereof.

Examples of the "other chemotherapeutic agent" include, but not limited to, finasteride, sobuzoxane, obatoclax, efaproxiral, tipifarnib, and lonafarnib.

The pharmaceutical composition of the present invention may further contain other additives, and examples of such additives include surfactant, antioxidants, preservatives, and soothing agents.

The compound of formula (1) or a pharmaceutically acceptable salt thereof may be administered simultaneously with or at any interval before or after the antigenic substance (immunogen) in a unit dose ranging from generally 5 to 5000 mg/m$^2$ of body surface area, i.e., about 0.1 ng/kg to 100 mg/kg, which provides an effective dose for vaccine adjuvant. The unit dosage form for injections generally contains, for example, 1 ng to 250 mg of the active ingredient, and preferably, used at a dose ranging from 1 ng to 50 mg/kg of the active ingredient per day. However, the daily dose may vary depending on the host to be treated, the route of administration and the severity of the disease being treated. Thus, the optimal dose can be determined by a practitioner who treats individual patient or warm-blooded animal.

The term "treatment" as used herein means alleviating some or all of the symptoms of disease, in whole or in part, or preventing or delaying the progression of disease.

The term "prevention" as used herein means primary prevention of disease (prevention of onset of disease) or secondary prevention of disease (prevention of relapse in a patient whose symptom has been alleviated or disease has been cured after the onset of the disease, prevention of recurrence).

Since the compound of the present invention or a pharmaceutically acceptable salt thereof has an immune adjuvant activity in vitro or in vivo, it is useful as a vaccine adjuvant for maintaining or enhancing the immunogenicity of the antigen (tumor antigen or pathogen-derived antigen).

The compound of the present invention or a pharmaceutically acceptable salt thereof has an adjuvant activity for cellular immunity in vitro or in vivo, and thus it is useful as a vaccine adjuvant for maintaining or enhancing the immunogenicity of tumor antigen.

The compound of the present invention or a pharmaceutically acceptable salt thereof can be used for maintaining or enhancing the effect of an immunostimulant for treating or preventing a disease, that is a substance inducing an antigen (tumor antigen or pathogen-derived antigen)-specific immune reaction.

The pharmaceutical composition comprising the compound of the present invention or a pharmaceutically acceptable salt thereof, and a substance enhancing the specific immune response for tumor antigen or pathogen (also referred to as tumor antigen or pathogen-derived antigen) is also included in one embodiment of the present invention. The tumor antigen includes, but not limited to, an antigen protein or an antigen peptide (partial peptide) derived from said antigen protein, a tumor antigen protein or a tumor antigen peptide (partial peptide) derived from said tumor antigen protein, or a complex thereof with a carrier.

In a specific embodiment of the present invention, the present compound or a pharmaceutically acceptable salt thereof can treat or prevent cancer by the administration with a tumor antigen protein or a tumor antigen peptide for cancer immunotherapy. The cancer includes, for example, leukemia, myelodysplastic syndrome, multiple myeloma, malignant lymphoma, stomach cancer, colon cancer, lung cancer, breast cancer, germ cell cancer, liver cancer, skin cancer, bladder cancer, prostate cancer, uterine cancer, cervical cancer, ovarian cancer, brain tumor, bone cancer, pancreatic cancer, head and neck cancer, skin or intraorbital malignant melanoma, rectal cancer, anal cancer, testicular cancer, fallopian tube carcinoma, endometrial carcinoma, uterocervical carcinoma, vaginal carcinoma, vulval carcinoma, Hodgkin's disease, non-Hodgkin's lymphoma, esophageal cancer, small intestinal cancer, endocrine system cancer, thyroid cancer, parathyroid cancer, adrenal cancer, soft tissue sarcoma, urethral cancer, penile cancer, acute myeloid leukemia, chronic myeloid leukemia, acute lymphoblastic leukemia, chronic or acute leukemia including chronic lymphocytic leukemia, children solid cancer, lymphocytic lymphoma, renal/ureter cancer, renal pelvic carcinoma, central nervous system (CNS) tumor, primary CNS lymphoma, tumor angiogenesis, spinal tumor, pontine glioma, pituitary adenoma, Kaposi's sarcoma, squamous cell carcinoma, planocellular carcinoma, T-cell lymphoma, polytypic glioblastoma, malignant melanoma, non-small-cell lung cancer, renal cell cancer, and asbestos-induced cancer. The treatment or prevention of cancer includes preventing metastatic disease and tumor recurrence, and preventing and treating paraneoplastic syndrome.

In a specific embodiment, the compound of the present invention or a pharmaceutically acceptable salt thereof, by administering in combination with an active ingredient of a vaccine for preventing infectious diseases, can prevent various infectious diseases such as genital wart, common wart, plantar wart, hepatitis B, hepatitis C, herpes simplex virus, molluscum contagiosum, smallpox, human immunodeficiency virus (HIV), human papilloma virus (HPV), RS virus, norovirus, cytomegalovirus (CMV), varicella zoster virus (VZV), rhinovirus, adenovirus, coronavirus, influenza, and parainfluenza; bacterial diseases such as tuberculosis, *Mycobacterium avium*, and Hansen's disease; infections such as mycosis, chlamydia, Candida, Aspergillus, cryptococcal meningitis, *Pneumocystis carini*, cryptosporidiosis, histoplasmosis, toxoplasmosis, malaria, Trypanosoma infection, and leishmaniasis. Examples of the active ingredient of the vaccine for preventing infectious include, but not limited to, substances derived from microorganisms/pathogens including bacteria, fungi, protozoa, and viruses which cause infectious diseases, such as antigenic protein, antigen peptide (partial peptide) from said antigenic protein, polysaccharide, lipid, and a combination thereof or a combination of the substance derived from said microorganisms/pathogen and a carrier.

Examples of the viral antigenic peptide derived from the viral antigen include, but not limited to, influenza matrix protein peptide 58-66 (Jager E et al., Int. J. Cancer 67: 54 (1996)), HPV16 E7 peptide 86-93 (van Driel W J et al., Eur. J. Cancer 35:946 (1999)), HPV E7 peptide 12-20 (Scheibenbogen C et al., J. Immunother 23: 275 (2000)), HPV16 E7 peptide 11-20 (Smith J W I et al., J. Clin. Oncol. 21: 1562 (2003)), HSV2 gD (Berman P W et al., Science 227: 1490 (1985)), CMV gB (Frey S E et al., Infect Dis. 180: 1700 (1999), Gonczol E. et al., Exp. Opin. Biol. Ther. 1: 401 (2001)), and CMV pp 65 (Rosa C L et al., Blood 100: 3681 (2002), Gonczol E. et al., Exp. Opin. Biol. Ther. 1: 401 (2001)).

The carrier as used herein is a substance, such as protein and lipid, to which an antigenic protein or an antigenic peptide is bound chemically and/or physically, and examples include, but not limited to, CRM 197 (Vaccine. 2013 Oct. 1; 31(42):4827-33), KLH (Cancer Immunol Immunother. 2003 October; 52(10):608-16), virus-like particles (PLoS ONE 5(3): e9809) and liposomes (J Liposome Res. 2004; 14(3-4):175-89).

The antigenic protein may be prepared by cloning cDNA, which encodes the antigenic protein, and expression in a host cell, according to a textbook such as Molecular Cloning 2nd ed., Cold Spring Harbor Laboratory Press (1989).

The synthesis of the antigenic peptide can be carried out according to a method generally used in peptide chemistry, for example, as described in literatures (Peptide Synthesis, Interscience, New York, 1966; The Proteins, Vol. 2, Academic Press Inc., New York, 1976).

In an embodiment, the present invention further provides a kit comprising:

a) a compound of the formula (1) or a pharmaceutically acceptable salt thereof, or a pharmaceutical composition comprising a compound of the formula (1) or a pharmaceutically acceptable salt thereof; and b) an antigen (tumor antigen or pathogen-derived antigen) or a pharmaceutical composition comprising an antigen (tumor antigen or pathogen-derived antigen).

The antigen is not limited so long as it is an antigen that may be used as an active ingredient of vaccines, which includes antigenic proteins as mentioned above, antigenic peptides (partial peptides) derived from such antigenic proteins, and a complex thereof with a carrier.

In an embodiment, the present invention provides a kit comprising:

a) a compound of the formula (1) or a pharmaceutically acceptable salt thereof, or a pharmaceutical composition comprising a compound of the formula (1) or a pharmaceutically acceptable salt thereof; and b) a tumor antigen or a pharmaceutical composition comprising a tumor antigen.

The tumor antigen herein should not be limited as long as the tumor antigen can be used as an active ingredient for a cancer vaccine, which includes the above-mention tumor antigen protein or a tumor antigen peptide (partial peptide) derived from said antigen protein, and further a complex thereof with a carrier.

In an embodiment, the present invention provides a kit comprising:

a) a compound of the formula (1) or a pharmaceutically acceptable salt thereof, or a pharmaceutical composition comprising a compound of the formula (1) or a pharmaceutically acceptable salt thereof; and b) a pathogen-derived antigen or a pharmaceutical composition comprising a pathogen-derived antigen.

The pathogen-derived antigen herein should not be limited as long as the pathogen-derived antigen can be used as an active ingredient for an infective vaccine, which includes the above-mention pathogen-derived antigen protein or a pathogen-derived antigen peptide (partial peptide) derived from said pathogen-derived antigen protein, and further a complex thereof with a carrier.

In one embodiment of the present invention, the present invention provides use of a compound of the formula (1) or a pharmaceutically acceptable salt thereof in the preparation of a vaccine adjuvant.

Further in one embodiment of the present invention, the present invention provides use of a compound of the formula (1) or a pharmaceutically acceptable salt thereof as a vaccine adjuvant in the preparation of a vaccine for treating cancer or infection.

In one embodiment of the present invention, the present invention provides use of a compound of the formula (1) or a pharmaceutically acceptable salt thereof in the preparation of a vaccine adjuvant for a cancer vaccine.

Further in one embodiment of the present invention, the present invention provides use of a compound of the formula (1) or a pharmaceutically acceptable salt thereof as a vaccine adjuvant in the preparation of a cancer vaccine for treating cancer.

In one embodiment of the present invention, there is provided a use of a compound of the formula (1), or a pharmaceutically acceptable salt thereof, for the manufacture of a vaccine adjuvant for infection vaccine.

In one embodiment of the present invention, there is provided a use of a compound of the formula (I) as defined above, or a pharmaceutically acceptable salt thereof, as a vaccine adjuvant in the manufacture of an infection vaccine for the treatment of an infection.

Further, one embodiment of the present invention provides a method for the treatment or prevention of cancer or infection, or the prevention of the progress thereof, comprising a step of administering a compound of the formula (I) as defined above, or a pharmaceutically acceptable salt thereof, together with an antigen (tumor antigen or pathogen-derived antigen), to a patient.

One embodiment of the present invention provides a method for the treatment or prevention of cancer, or the prevention of the progress thereof, comprising a step of administering a compound of the formula (I) as defined above, or a pharmaceutically acceptable salt thereof, together with a tumor antigen, to a patient.

One embodiment of the present invention provides a method for the treatment or prevention of infection, or the prevention of the progress thereof, comprising a step of administering a compound of the formula (I) as defined above, or a pharmaceutically acceptable salt thereof, together with a pathogen-derived antigen, to a patient.

EXAMPLES

The present invention will be further described with reference to the following examples which should not be regarded as limiting in any respect.

Fmoc: 9-fluorenylmethyloxycarbonyl
Boc: tert-butoxycarbonyl
Alko: p-alkoxybenzyl alcohol
PEG: polyethylene glycol
tBu: tert-butyl
HBTU: 0-(benzotriazol-1-yl)-N,N,N',N'-tetramethyluronium hexafluorophosphate
DIPEA: N,N-diisopropylethylamine
DMF: N,N-dimethylformamide
TFA: trifluoroacetic acid
TIS: triisopropylsilane
THF: tetrahydrofuran
TBS: tert-butyldimethylsilyl group
TBDPS: tert-butyldiphenylsilyl group The analysis conditions of high performance liquid chromatograph-mass spectrometer (LCMS) are shown below.

LCMS Condition A
MS detector: LCMS-IT-TOF
HPLC: Shimadzu Nexera X2 LC 30AD
Column: Kinetex 1.7µ C18 100A New column 50×2.1 mm
Flow rate: 1.2 ml/min
Wave length: 254/220 nm
Mobile phase:
A: 0.1% formic acid/water
B: acetonitrile
Time program:

| Step | Time (min) |
|---|---|
| 1 | 0.01-1.40 A:B = 90:10-5:95 |
| 2 | 1.40-1.60 A:B = 5:95 |
| 3 | 1.61-2.00 A:B = 99:1 |

LCMS Condition B
MS detector: ACQUITY™ SQ detecter (Waters)
HPLC: ACQUITY™ system
Column: Waters ACQUITY™ UPLC BEH C18 (1.7 µm, 2.1 mm×30 mm)
Flow rate: 0.8 ml/min
Wave length: 254/220 nm
Mobile phase:
A: 0.06% formic acid/acetonitrile
B: 0.06% formic acid/water
Time program: 0.0-1.30 A:B=2:98-96:4
Column temperature: 25° C.

Reference Example 1

Synthesis of a Peptide Consisting of Amino Acid Sequence:

(SEQ ID NO: 1)
RMFPNAPYL (Arg-Met-Phe-Pro-Asn-Ala-Pro-Tyr-Leu)

From 1.00 g of (Fmoc-Lys(Boc)-Alko-PEG Resin) (WATANABE CHEMICAL INDUSTRIES, LTD.; 0.23 mmol/g, 0.23 mmol) as a starting material, the peptide chain was elongated by solid-phase synthesis of Fmoc/tBu method. The solid-phase synthesis was done with CS336X peptide synthesizer (CSBio), and Fmoc group was deprotected by the treatment with 20% piperidine in DMF for 5 minutes or 20 minutes. The coupling of the protected amino acid to the resin compound was done by reacting the resin compound with a solution of 1.05 mmol of the protected amino acid, 1 mmol of HBTU, and 2 mmol of DIPEA in DMF for one hour. The obtained resin was washed with DMF and ether and dried in vacuo to give a peptide resin. To the peptide resin was added 10 mL of a mixture of TFA/water/TIS (volume ratio: 94/2.5/2.5), and the mixture was shaken at room temperature for 2 hours. The resin was removed by filtration, and the reaction solution was concentrated under reduced pressure. The reaction solution was cooled at ice temperature, and diethyl ether (50 mL) was added thereto. The resulting precipitate was collected on a filter, washed with ether, and dried in vacuo to give a crude peptide. The obtained crude peptide was dissolved in a mixture of 20% acetic acid/water and acetonitrile (volume ratio: 1/1), and purified according to the condition shown below to give trifluoroacetate of RMFPNAPYL (Arg-Met-Phe-Pro-Asn-Ala-Pro-Tyr-Leu) (SEQ ID NO: 1) (0.16 g). The obtained trifluoroacetate was converted to its acetate in a common manner, which was evaluated.

Mass spectrometry: m/z=554.73 $[M+2H]^{+2}$, Retention time: 0.82 min (LCMS Condition A)

Purification Condition

HPLC system: High throughput HPLC preparative system (Gilson)

Column: YMC ODS-A 3 cmφ×25 cm, 10 μm

Eluate 1: 0.1% TFA/water

Eluate 2: 0.035% TFA/acetonitrile

Flow rate: 20 mL/min

Gradient method:

| Time (min) | Concentration of Eluate 2 (%) |
|---|---|
| 0 | 10 |
| 25 | 50 |

According to the method described in Reference example 1, the peptides shown in Table 1 were prepared as their trifluoroacetate from each corresponding starting material. These compounds were dealt as reference examples since they are not within the present compounds. Reference example 3 was converted to its acetate in a common manner, which was evaluated as follows.

TABLE 1

| Reference example No. | SEQ ID No. | Amino acid sequence and structure | LCMS condition A (m/z, Retention time (min)) |
|---|---|---|---|
| 2 | 2 | CYTWNQMNL | 586.7 $[M + 2H]^{+2}$, 0.87 |
| 3 | 3 | WAPVLDFAP PGASAYGSL | 910.3 $[M + 2H]^{+2}$, 0.95 |
| 4 | 4 | VLDFAPPGA | 884.4 $[M - H]^{-}$, 0.75 |
| 5 | 5 | VLQELNVTV | 507.8 $[M + 2H]^{+2}$, 1.14 |
| 6 | 6 | GLYDGMEHL | 517.7 $[M + 2H]^{+2}$, 1.12 |
| 7 | 7 | KIFGSLAFL | 498.2 $[M + 2H]^{+2}$, 1.34 |

According to the method described in WO 2014/157692, the compound shown in Table 2 (wherein the bond between C—C is disulfide bond) was prepared as its trifluoroacetate. The compound was dealt as a reference example since it are is within the present compounds.

TABLE 2

| Reference example No. | Formula No. | Structure | LCMS condition A (m/z, Retention time (min)) |
|---|---|---|---|
| 8 | 4 | CRMFPNAPYL<br>\|<br>CYTWNQMNL | 794.60 $[M + 3H]^{+3}$, 0.88 |

Reference Example 9

Preparation of N-2,2,3,3-pentamethyl-4,7,10,13,16-pentaoxa-3-silaoctadecane-18-amine

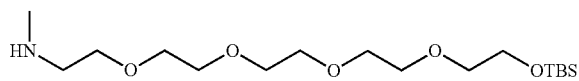 [SMILES: CNCCOCCOCCOCCOCCO[Si](C)(C)C(C)(C)C]

Step 1

To a solution of 14-amino-3,6,9,12-tetraoxatetradecan-1-ol (1.60 g) which is a known compound in THF (25 mL) were added triethylamine (4.7 mL) and ethyl trifluoroacetate (2.4 mL), and the solution was stirred at room temperature for 2 hours. The reaction solution was concentrated under reduced pressure, and the obtained crude product was purified by silica gel chromatography (mobile phase: chloroform/methanol) to give 2,2,2-trifluoro-N-(14-hydroxy-3,6,9,12-tetraoxatetradecan-1-yl)acetamide (1.00 g). m/z=334 $[M+H]^+$, Rt=0.507 (LCMS Condition B)

Step 2

To a solution of the compound (3.91 g) prepared in Reference example 9 (Step 1) in DMF (20 mL) were added triethylamine (4.90 mL) and tert-butyldimethylchlorosilane (3.54 g), and the solution was stirred at room temperature for 2 hours. The reaction solution was diluted with ethyl acetate, washed with water and brine, dried over sodium sulfate, filtered, and concentrated under reduced pressure. The obtained crude product was purified by silica gel chromatography (mobile phase: hexane/ethyl acetate) to give 2,2,2-trifluoro-N-(2,2,3,3-tetramethyl-4,7,10,13,16-pentaoxa-3-silaoctadecan-18-yl)acetamide (3.70 g). m/z=448 $[M+H]^+$, Rt=1.153 (LCMS Condition B)

Step 3

To a solution of the compound (4.44 g) prepared in Reference example 9 (Step 2) in DMF (20 mL) were added cesium carbonate (6.46 g) and methyl iodide (1.6 g), and the solution was stirred at room temperature for 2 hours. The reaction solution was diluted with ethyl acetate, washed with water and brine, dried over sodium sulfate, filtered, and concentrated under reduced pressure. The obtained crude product was purified by silica gel chromatography (mobile phase: hexane/ethyl acetate) to give 2,2,2-trifluoro-N-methyl-N-(2,2,3,3-tetramethyl-4,7,10,13,16-pentaoxa-3-silaoctadecan-18-yl)acetamide (3.31 g).

m/z=463 [M+H]$^+$, Rt=1.210 (LCMS Condition B)

Step 4

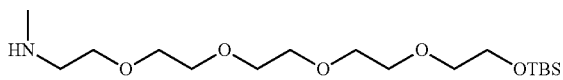 [SMILES: CNCCOCCOCCOCCOCCO[Si](C)(C)C(C)(C)C]

To a solution of the compound (117 mg) prepared in Reference example 9 (Step 3) in methanol (5 mL) was added potassium carbonate (70 mg), and the solution was stirred at room temperature for 5 hours. The reaction solution was concentrated, and the obtained crude product was purified by silica gel chromatography (mobile phase: chloroform/methanol) to give N-2,2,3,3-pentamethyl-4,7,10,13,16-pentaoxa-3-silaoctadecane-18-amine (67 mg). m/z=366 [M+H$^+$], Rt=0.718 (LCMS Condition B)

Reference Example 10

Preparation of N,2,2-trimethyl-3,3-diphenyl-4,7,10,13,16-pentaoxa-3-silaoctadecane-18-amine

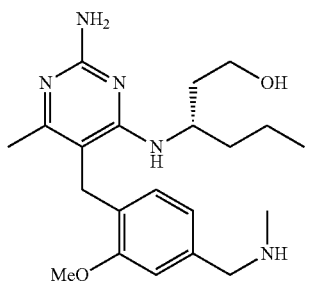 [SMILES: CCC[C@@H](CCO)Nc1nc(N)nc(C)c1Cc1ccc(CNC)cc1OC]

The title compound was prepared according to the process of Reference example 9.

m/z=490 [M+H]$^+$, Rt=0.953 (LCMS Condition B)

Reference Example 11

Preparation of (3S)-3-{[2-amino-5-({2-methoxy-4-[(methylamino)methyl]phenyl}methyl)-6-methylpyrimidin-4-yl]amino}hexan-1-ol

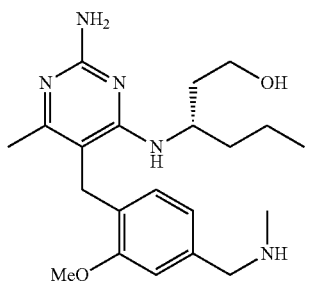 [SMILES: CCC[C@@H](CCO)Nc1nc(N)nc(C)c1Cc1ccc(CNC)cc1OC]

The title compound was prepared according to the process disclosed in WO 2012/066336.

m/z=194 [M+2H]$^{+2}$, Rt=0.552 (LCMS Condition B)

Reference Example 12

Preparation of 5-({2-methoxy-4-[(methylamino)methyl]phenyl}methyl)-6-methyl-N$^4$-pentylpyrimidine-2,4-diamine

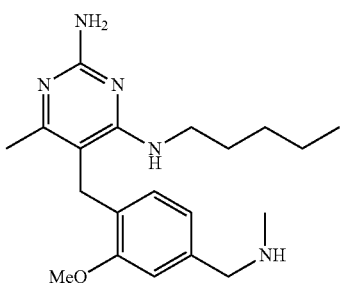 [SMILES: CCCCCNc1nc(N)nc(C)c1Cc1ccc(CNC)cc1OC]

The title compound was prepared from 5-{[4-(chloromethyl)-2-methoxyphenyl]methyl}-6-methyl-N$^4$-pentylpyrimidine-2,4-diamine which is a known compound according to similar reaction and treatment to the procedure of Example 1.

m/z=179 [M+2H]$^{+2}$, Rt=0.475 (LCMS Condition B)

Reference Example 13

Preparation of 3-{[2-amino-4-methyl-6-(pentylamino)pyrimidin-5-yl]methyl}-4-methoxybenzaldehyde

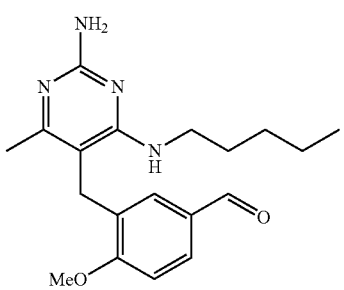

The title compound was prepared from methyl 3-{[2-amino-4-methyl-6-(pentylamino)pyrimidin-5-yl]methyl}-4-methoxybenzoate which is a known compound according to similar reaction and treatment to the procedure disclosed in WO 2017/061532.

m/z=179 [M+2H]$^{+2}$, Rt=0.475 (LCMS Condition B)

Reference Example 14

Preparation of 3-{[2-amino-4-methyl-6-(pentylamino)pyrimidin-5-yl]methyl}-4-hydroxybenzaldehyde

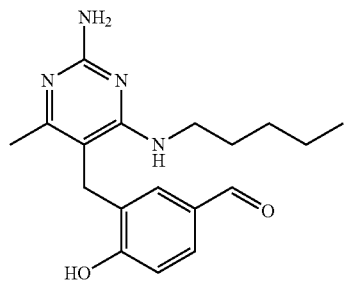 [SMILES: CCCCCNc1nc(N)nc(C)c1Cc1cc(C=O)ccc1O]

To a solution of Reference example 13 (104 mg) in dichloromethane (5 mL) was added a solution of boron tribromide in dichloromethane (1.0 M, 0.8 mL) under ice cooling, and the solution was stirred at room temperature for 6 hours. Aqueous saturated sodium bicarbonate was added to the reaction solution. The mixture was extracted with chloroform, and the organic layer was dried over sodium sulfate, filtered, and concentrated. The obtained crude product was purified by silica gel chromatography (mobile phase: chloroform/methanol) to give the title compound (54 mg).

m/z=329 [M+H]$^+$, Rt=0.748 (LCMS Condition B)

Reference Example 15

Preparation of 5-({2-methoxy-5-[(methylamino)methyl]phenyl}methyl)-6-methyl-N$^4$-pentylpyrimidine-2,4-diamine

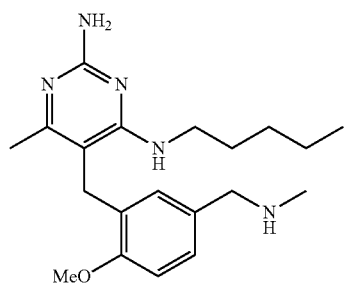

The title compound was prepared from Reference example 13 according to similar reaction and treatment to the procedure of Example 3.

m/z=179 [M+2H]$^{+2}$, Rt=0.599 (LCMS Condition B)

Reference Example 16

Preparation of 2-{[2-amino-4-methyl-6-(pentylamino)pyrimidin-5-yl]methyl}-4-[(methylamino)methyl]phenol

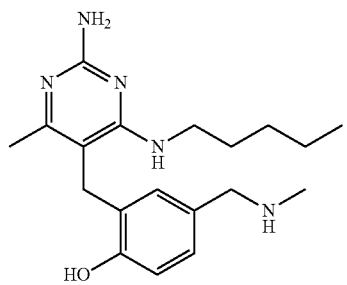 [SMILES: CCCCCNc1nc(N)nc(C)c1Cc1cc(CNC)ccc1O]

The title compound was prepared from Reference example 14 according to similar reaction and treatment to the procedure of Example 3.

m/z=173 [M+2H]$^{+2}$, Rt=0.562 (LCMS Condition B)

Reference Example 17

N, 2,2,3,3-Pentamethyl-4,7,10,13,16,19,22,25,28,31-decaoxa-3-silatritriacontane-33-amine

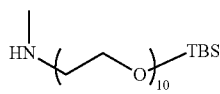

The title compound was prepared according to the process of Reference example 9.

m/z=587 [M+H]$^+$, Rt=0.865 (LCMS Condition B)

Reference Example 18

N,2,2,3,3-Pentamethyl-4,7,10, 13,16,19,22,25,28,31, 34,37,40,43,46, 49, 52, 55, 58, 61, 64,67,70,73-tetracosaoxa-3-silapentaheptacontane-75-amine

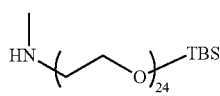

The title compound was prepared according to the process of Reference example 9.

m/z=402 [M+3H]$^{+3}$, Rt=0.946 (LCMS Condition B)

Reference Example 19

N,2,2,3,3-Pentamethyl-4,7,10,13,16,19,22,25,28,31, 34, 37,40,43,46,49,52,55,58,61,64,67,70,73,76,79, 82,85,88,91,94,97,100,103,106,109-hexatriacontaoxa-3-silahendecahectane-111-amine

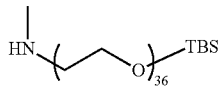

The title compound was prepared according to the process of Reference example 9.
m/z=866 [M+2H]$^{+2}$, Rt=0.948 (LCMS Condition B)

Example 1

Preparation of 1-(4-{[2-amino-4-methyl-6-(pentylamino)pyrimidin-5-yl]methyl}-3-methoxyphenyl)-2-methyl-5,8,11,14-tetraoxa-2-azahexadecan-16-ol·trifluoroacetate

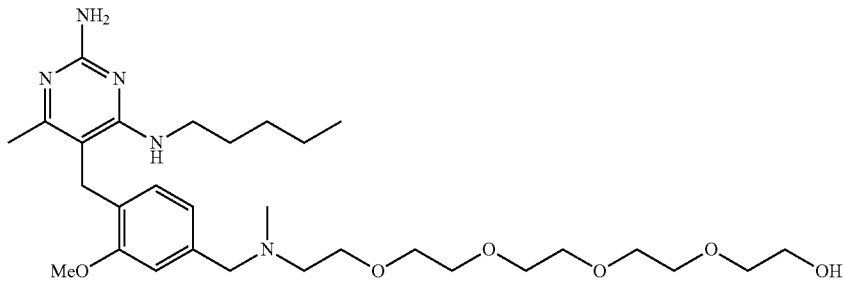 [SMILES: CCCCCNc1nc(N)nc(C)c1Cc1ccc(CN(C)CCOCCOCCOCCOCCO)cc1OC]

To a solution of 5-{[4-(chloromethyl)-2-methoxyphenyl]methyl}-6-methyl-N$^4$-pentylpyrimidine-2,4-diamine (75 mg) which is a known compound in acetonitrile (3 mL) were added Reference example 9 (76 mg), potassium carbonate (65 mg), and potassium iodide (67 mg), and the solution was stirred at 60° C. for 8 hours. The reaction solution was concentrated, and purified by reversed-phase HPLC like the case of Reference example 1 to give the title compound (96 mg).
m/z=290 [M+2H]$^{+2}$, Rt=0.623 (LCMS Condition B)
$^1$H-NMR (CDCl$_3$): δ 7.34 (s, 1H), 6.92 (d, J=8.0 Hz, 1H), 6.96 (d, J=8.0 Hz, 1H), 6.08 (t, J=5.6 Hz, 1H), 3.96 (s, 3H), 3.88 (m, 2H), 3.70 (m, 2H), 3.64-3.55 (m, 18H), 3.47 (s, 1H), 3.34 (dd, J=6.8, 12 Hz, 2H), 2.81 (s, 3H), 2.47 (s, 3H), 1.49-1.42 (m, 2H), 1.30-1.23 (m, 2H), 1.21-1.13 (m, 2H), 0.85 (t, J=7.2 Hz, 3H)

Example 2

Preparation of 1-{4-[(2-amino-4-{[(3S)-1-hydroxyhexan-3-yl]amino}-6-methylpyrimidin-5-yl)methyl]-3-methoxyphenyl}-2-methyl-5,8,11,14-tetraoxa-2-azahexadecan-16-ol·trifluoroacetate

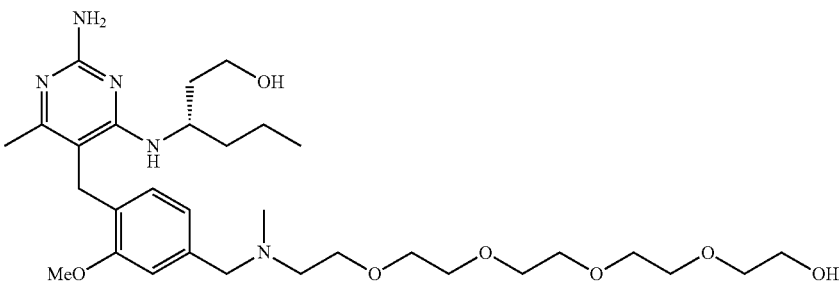 [SMILES: CCC[C@@H](CCO)Nc1nc(N)nc(C)c1Cc1ccc(CN(C)CCOCCOCCOCCOCCO)cc1OC]

The title compound was prepared from (3S)-3-[(2-amino-5-{[4-(chloromethyl)-2-methoxyphenyl]methyl}-6-methylpyrimidin-4-yl)amino]hexan-1-ol which is a known compound according to similar reaction and treatment to the procedure of Example 1.

m/z=305 [M+2H]$^{+2}$, Rt=0.527 (LCMS Condition B)

Example 3

Preparation of 1-(3-{[2-amino-4-methyl-6-(pentylamino)pyrimidin-5-yl]methyl}-4-methoxyphenyl)-2-methyl-5,8,11,14-tetraoxa-2-azahexadecan-16-ol-trifluoroacetate

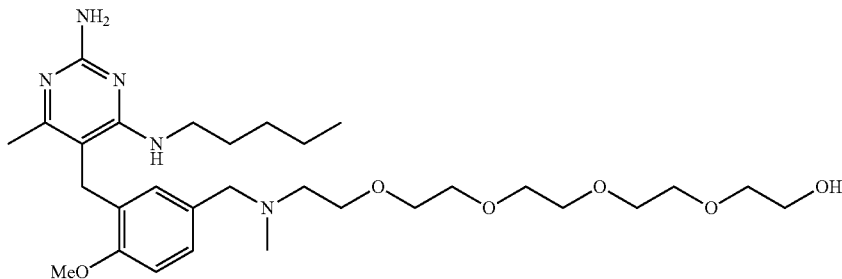 [SMILES: CCCCCNc1nc(N)nc(C)c1Cc1cc(CN(C)CCOCCOCCOCCOCCO)ccc1OC]

To a solution of Reference example 13 (64.3 mg) in THF (5 mL) were added Reference example 9 (101 mg), acetic acid (5.4 μL), and sodium triacetoxyborohydride (199 mg), and the solution was stirred at room temperature for 24 hours. Water was added to the reaction solution, and aqueous saturated sodium bicarbonate was added thereto to neutralize the solution. The mixture was extracted with ethyl acetate. The organic layer was washed with brine, dried over sodium sulfate, filtered, and concentrated. The obtained crude product was purified by HPLC to give the TBDPS-protected desired compound. The obtained protected compound was dissolved in methanol, and the solution was stirred at room temperature for 12 hours. The reaction solution was concentrated, and purified by reversed-phase HPLC to give the title compound (26 mg).

m/z=290 [M+2H]$^{+2}$, Rt=0.661 (LCMS Condition B)

$^{1}$H-NMR (CDCl$_3$): δ 7.32 (dd, J=1.6, 8.4 Hz, 1H), 7.13 (d, J=1.6 Hz, 1H), 6.87 (d, J=8.4 Hz, 1H), 6.24 (t, J=4.8 Hz, 1H), 4.26 (m, 2H), 3.86 (s, 3H), 3.81 (m, 2H), 3.64-3.49 (m, 18H), 3.29 (dd, J=6.8, 12.8 Hz, 2H), 2.70 (s, 3H), 2.43 (s, 3H), 1.44-1.36 (m, 2H), 1.24-1.17 (m, 2H), 1.13-1.07 (m, 2H), 0.80 (t, J=7.2 Hz, 3H)

Example 4

Preparation of 1-(3-{[2-amino-4-methyl-6-(pentylamino)pyrimidin-5-yl]methyl}-4-hydroxyphenyl)-2-methyl-5,8,11,14-tetraoxa-2-azahexadecan-16-ol-trifluoroacetate

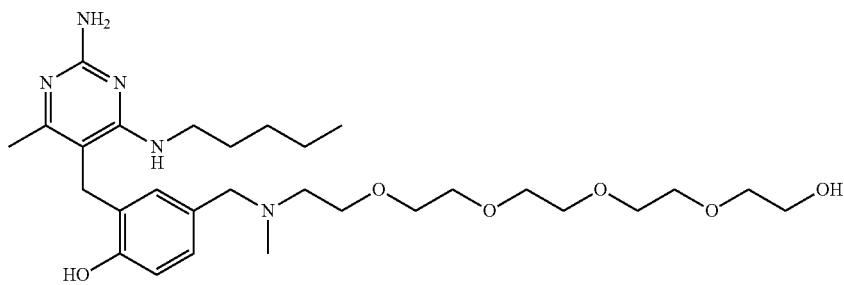 [SMILES: CCCCCNc1nc(N)nc(C)c1Cc1cc(CN(C)CCOCCOCCOCCOCCO)ccc1O]

To a solution of Reference example 14 (30 mg) in THF (5 mL) were added Reference example 9 (49 mg), acetic acid (2.6 μL), and sodium triacetoxyborohydride (97 mg), and the solution was stirred at room temperature for 24 hours. Water was added to the reaction solution, and aqueous saturated sodium bicarbonate was added thereto to neutralize the solution. The mixture was extracted with ethyl acetate. The organic layer was washed with brine, dried over sodium sulfate, filtered, and concentrated. The obtained crude product was purified by HPLC to give the TBDPS-protected desired compound. The obtained protected compound was dissolved in methanol, and the solution was stirred at room temperature for 12 hours. The reaction solution was concentrated, and purified by reversed-phase HPLC to give the title compound (13 mg).

m/z=290 [M+2H]$^{+2}$, Rt=0.661 (LCMS Condition B)

$^1$H-NMR (CDCl$_3$): δ 7.30 (t, J=5.2 Hz, 1H), 7.07 (d, J=2.0 Hz, 1H), 6.97 (dd, J=1.6, 8.0 Hz, 1H), 6.89 (d, J=8.4 Hz, 1H), 4.10 (m, 2H), 3.70 (t, J=5.6 Hz, 2H), 3.63 (d, J=5.6 Hz, 2H), 3.55-3.49 (m, 18H), 3.26 (dd, J=7.2, 13.2 Hz, 2H), 2.68 (s, 3H), 2.43 (s, 3H), 1.47-1.40 (m, 2H), 1.24-1.15 (m, 2H), 1.13-1.05 (m, 2H), 0.76 (t, J=6.8 Hz, 3H)

Example 5

Preparation of 4-[(2-amino-4-{[(2S)-1-hydroxypentan-2-yl]amino}-6-methylpyrimidin-5-1)methyl]-N-(20-hydroxy-3,6,9,12,15,18-hexaoxaicosan-1-yl)-3-methoxybenzamide $^1$H-NMR (CDCl$_3$): δ 7.49 (1H, s), 7.21 (1H, d, J=7.9 Hz), 7.05 (1H, s), 6.95 (1H, d, J=7.9 Hz), 4.77 (1H, d, J=6.7 Hz), 4.68 (2H, s), 4.01-3.92 (1H, m), 3.94 (3H, s), 3.75-3.68 (4H, m), 3.67-3.51 (26H, m), 3.42-3.35 (1H, m), 2.28 (3H, s), 1.45-1.36 (1H, m), 1.29-1.20 (1H, m), 1.16-1.06 (2H, m), 0.80 (3H, t, J=7.3 Hz).

Example 6

Preparation of 2,5,8,11-tetraoxatridecan-13-yl 4-[(2-amino-4-{[(2S)-1-hydroxypentan-2-yl]amino}-6-methylpyrimidin-5-yl)methyl]-3-methoxybenzoate

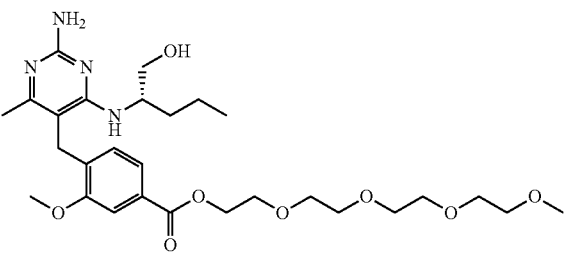

To a solution of 4-[(2-amino-4-{[(2S)-hydroxypentan-2-yl]amino}-6-methylpyrimidin-5-yl)methyl]-3-methoxybenzoic acid (30 mg) which is a known compound in THE (1.5 mL) were added 2,5,8,11-tetraoxatridecan-13-ol (501 mg),

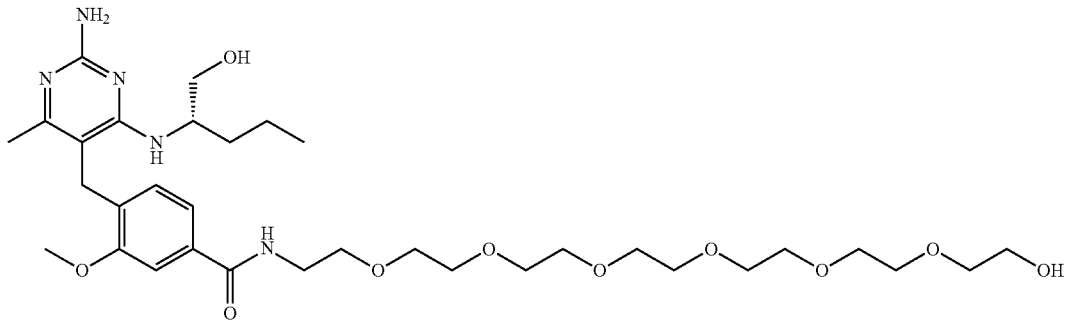 [SMILES: CCC[C@@H](CO)Nc1nc(N)nc(C)c1Cc1ccc(C(=O)NCCOCCOCCOCCOCCOCCOCCO)cc1OC]

To a solution of 4-[(2-amino-4-{[(2S)-hydroxypentan-2-yl]amino}-6-methylpyrimidin-5-yl)methyl]-3-methoxybenzoic acid (30 mg) which is a known compound in DMF (1 mL) were added diisopropylethylamine (25.9 mg), 20-amino-3,6,9,12,15,18-hexaoxaicosan-1-ol (31.3 mg), and HATU (33.5 mg), and the solution was stirred at room temperature for 24 hours. Aqueous saturated sodium bicarbonate was added to the reaction solution, and the mixture was extracted with a mixture of chloroform/methanol (10:1), dried over magnesium sulfate, filtered, and concentrated. The obtained crude product was purified by amino silica gel column chromatography (mobile phase: chloroform/methanol) to give the title compound (28.1 mg).

m/z=683 [M+H]$^+$, Rt=0.558 (LCMS Condition B)

diisopropylethylamine (36.2 mg), and 1-ethyl-3-(3-dimethylaminopropyl)carbodiimide hydrochloride (46.1 mg), and the solution was stirred at 60° C. for 10 hours. The reaction solution was purified by silica gel column chromatography (mobile phase: chloroform/methanol) to give the title compound (16.2 mg).

m/z=565 [M+H]$^+$, Rt=0.665 (LCMS Condition B)

$^1$H-NMR (CDCl$_3$): δ 7.56 (1H, d, J=7.9 Hz), 7.51 (1H, s), 6.99 (1H, d, J=7.9 Hz), 6.12 (1H, d, J=7.9 Hz), 4.41 (2H, t, J=4.6 Hz), 4.20-4.10 (1H, m), 3.93 (3H, s), 3.86-3.41 (18H, m), 3.29 (3H, s), 3.02 (1H, q, J=7.5 Hz), 2.44 (3H, s), 1.50-1.22 (2H, m), 1.12-0.91 (2H, m), 0.74 (3H, t, J=7.0 Hz).

Example 7

Preparation of 5-{[2-methoxy-4-(2,5,8,11,14-pentaoxapentadecan-1-yl)phenyl]methyl}-6-methyl-N⁴-pentylpyrimidine-2,4-diamine

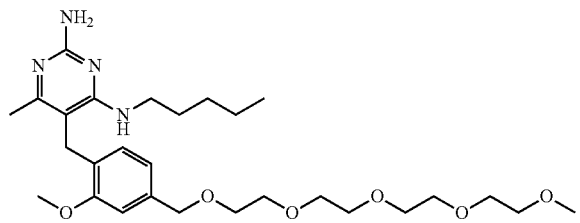

To 2,5,8,11-tetraoxatridecan-13-ol was added sodium hydride (7.2 mg, content>55%), and the mixture was stirred at room temperature for one hour. 5-{[4-(Chloromethyl)-2-methoxyphenyl]methyl}-6-methyl-N⁴-pentylpyrimidine-2,4-diamine (20 mg) which is a known compound was added thereto, and the mixture was stirred at 60° C. for 3 hours. Water was added to the reaction solution, and the mixture was extracted with chloroform, dried over magnesium sulfate, filtered, and concentrated. The obtained crude product was purified by silica gel column chromatography (mobile phase: chloroform/methanol) to give the title compound (6.7 mg). m/z=536 [M+H]⁺, Rt=0.850 (LCMS Condition B)

¹H-NMR (CDCl₃): δ 6.88 (1H, s), 6.84 (1H, d, J=7.3 Hz), 6.78 (1H, d, J=7.3 Hz), 5.80-5.40 (2H, br), 4.46 (2H, s), 3.86 (3H, s), 3.67-3.46 (19H, m), 3.30 (3H, s), 3.24 (2H, td, J=7.0, 5.5 Hz), 2.35 (3H, s), 1.36 (2H, m), 1.23-1.05 (4H, m), 0.78 (3H, t, J=7.0 Hz).

Example 8

Preparation of 1-(4-{[2-amino-4-methyl-6-(pentylamino)pyrimidin-5-yl]methyl}-3-methoxyphenyl)-2-methyl-5,8,11,14,17,20,23,26,29-nonaoxa-2-azahentriacontan-31-ol

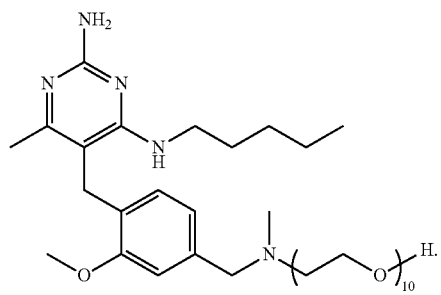

To a mixture of 5-{[4-(chloromethyl)-2-methoxyphenyl]methyl}-6-methyl-N⁴-pentylpyrimidine-2,4-diamine (40 mg) which is a known compound, Reference example 17 (64.6 mg), potassium iodide (36.6 mg), and potassium carbonate (30.5 mg) was added acetonitrile (1 mL), and the mixture was stirred at 80° C. for 2 hours. The reaction solution was diluted with chloroform, filtered to remove the insoluble matter, and concentrated. To the residue were added chloroform (1 mL) and TFA (0.1 mL), and the mixture was stirred at room temperature for one hour. The reaction solution was neutralized with aqueous sodium carbonate, extracted with chloroform, dried over magnesium sulfate, filtered, and concentrated. The obtained crude product was purified by amino silica gel column chromatography (mobile phase: chloroform/methanol) to give the title compound (28.4 mg).

m/z=400 [M+2H]⁺², Rt=0.583 (LCMS Condition B)

¹H-NMR (CDCl₃): δ 6.86 (1H, s), 6.81 (1H, d, J=7.9 Hz), 6.73 (1H, d, J=7.9 Hz), 6.00-5.00 (2H, br), 3.85 (3H, s), 3.68 (2H, t, J=4.6 Hz), 3.63-3.50 (40H, m), 3.44 (2H, s), 3.24 (2H, q, J=6.5 Hz), 2.54 (2H, t, J=6.1 Hz), 2.32 (3H, s), 2.19 (3H, s), 1.41-1.34 (2H, m), 1.23-1.16 (2H, m), 1.13-1.05 (2H, m), 0.78 (3H, t, J=7.3 Hz).

Example 9

Preparation of 1-(4-{[2-amino-4-methyl-6-(pentylamino)pyrimidin-5-yl]methyl}-3-methoxyphenyl)-2-methyl-5,8,11,14,17,20,23,26,29,32,35,38,41,44,47,50,53,56,59,62,65,68,71-tricosaoxa-2-azatriheptacontan-73-ol

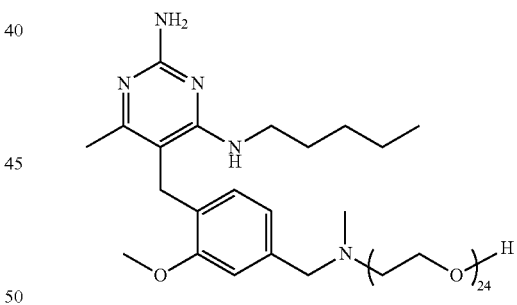

The title compound (31.6 mg) was prepared from Reference example 18 (83 mg) according to similar reaction to the procedure of Example 8.

m/z=708 [M+2H]⁺², Rt=0.672 (LCMS Condition B)

¹H-NMR (CDCl₃): δ 6.83 (1H, s), 6.79 (1H, d, J=7.9 Hz), 6.69 (1H, d, J=7.3 Hz), 4.79 (1H, s), 4.56 (2H, s), 3.83 (3H, s), 3.76-3.40 (99H, m), 3.21 (2H, dd, J=12.5, 7.0 Hz), 2.53 (2H, t, J=6.1 Hz), 2.24 (3H, s), 2.18 (3H, s), 1.39-1.32 (2H, m), 1.22-1.14 (2H, m), 1.12-1.04 (2H, m), 0.77 (3H, t, J=7.0 Hz).

Example 10

Preparation of 1-(4-{[2-amino-4-methyl-6-(pentylamino)pyrimidin-5-yl]methyl}-3-methoxyphenyl)-2-methyl-5,8,11,14,17,20,23,26,29,32,35,38,41,44,47,50,53,56,59,62,65,68,71,74,77,80,83,86,89,92,95,98,101,104,107-pentatriacontaoxa-2-azanonahectan-109-ol

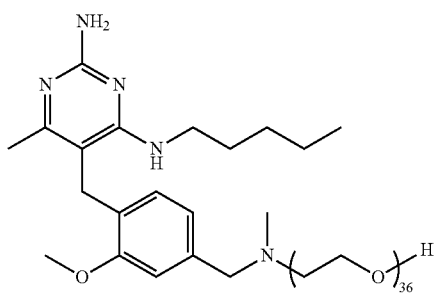

The title compound (26.3 mg) was prepared from Reference example 19 (95 mg) according to similar reaction to the procedure of Example 8.

m/z=487 [M+4H]$^{+4}$, Rt=0.693 (LCMS Condition B)

$^1$H-NMR (CDCl$_3$): δ 6.83 (1H, s), 6.79 (1H, d, J=7.9 Hz), 6.69 (1H, d, J=9.2 Hz), 4.81 (1H, s), 4.60 (2H, s), 3.83 (3H, s), 3.76-3.38 (147H, m), 3.21 (2H, dd, J=12.5, 7.0 Hz), 2.53 (2H, t, J=5.8 Hz), 2.24 (3H, s), 2.18 (3H, s), 1.39-1.32 (2H, m), 1.21-1.14 (2H, m), 1.12-1.06 (2H, m), 0.77 (3H, t, J=7.3 Hz)

Example 11

Preparation of 12-[(4-{[2-amino-4-methyl-6-(pentylamino)pyrimidin-5-yl]methyl}-3-methoxyphenyl)methyl]-3,6,9,15,18,21-hexaoxa-12-azatricosan-1,23-diol

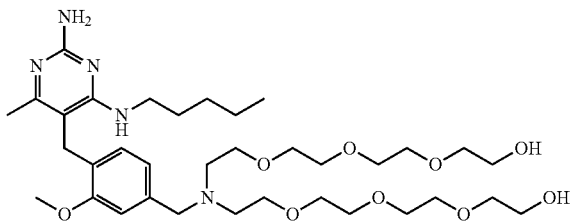 [SMILES: CCCCCNc1nc(N)nc(C)c1Cc1ccc(CN(CCOCCOCCOCCO)CCOCCOCCOCCO)cc1OC]

The title compound (13.1 mg) was prepared from 3,6,9,15,18,21-hexaoxa-12-azatricosan-1,23-diol (40.7 mg) according to similar reaction to the procedure of Example 1.

m/z=349 [M+2H]$^{+2}$, Rt=0.554 (LCMS Condition B)

$^1$H-NMR (CDCl$_3$) δ 6.85 (1H, s), 6.79 (1H, d, J=7.9 Hz), 6.73 (1H, d, J=7.9 Hz), 4.85 (1H, t, J=5.5 Hz), 4.57 (2H, s), 3.83 (3H, s), 3.68-3.42 (34H, m), 3.21 (2H, td, J=7.2, 5.3 Hz), 2.67 (4H, t, J=6.1 Hz), 2.24 (3H, s), 1.41-1.33 (2H, m), 1.23-1.09 (4H, m), 0.78 (3H, t, J=7.0 Hz).

Test 1
Human TLR7 Reporter Gene Assay

TLR7/NF-κB/SEAPorter™ HEK293 cell line (Imgenex Corporation) is a stably co-transfected cell line which expresses full-length human TLR7 and secretory alkaline phosphatase (SEAP) reporter gene under the transcriptional regulation of an NF-κB response element. The TLR7 expression of the cell line has been already tested by flow cytometry. Transfectants with stable expression were selected using the antibiotic blasticidin and Geneticin. TLR signaling leads to the translocation of NF-κB and the activation of the promoter results in expression of the SEAP gene. TLR7-specific activation was assessed by determining the level of SEAP produced following 24-hour incubation of the cells at 37° C. with each compound prepared in Examples and Reference examples in the presence of 0.1% (v/v) dimethylsulfoxide (DMSO). The human TLR7 activity for the present compound was assessed by human TLR7 reporter gene assay, and the results are shown in Tables 3 and 4 as the compound concentration which produced half of the maximal level of SEAP induction (EC$_{50}$)

TABLE 3

| Example No. | EC$_{50}$ (nM) |
| --- | --- |
| 1 | 68 |
| 2 | 94 |

TABLE 4

| Reference example No. | EC$_{50}$ (nM) |
| --- | --- |
| 11 | 8 |
| 12 | 50 |

Test 2
Mouse TLR7 Reporter Gene Assay

HEK-Blue™ mTLR7 cell line (Invivogen) is a stably co-transfected cell line which expresses full-length mouse TLR7 and secretory SEAP reporter gene under the transcriptional regulation of an NF-κB response element. The TLR7 expression of the cell line has been already tested by RT-PCR. Transfectants with stable expression were selected using the antibiotic blasticidin and Zeocin. TLR signaling leads to the translocation of NF-κB and the activation of the promoter results in expression of the SEAP gene. TLR7-specific activation was assessed by determining the level of SEAP produced following 20-24-hour incubation of the cells at 37° C. with each compound prepared in Examples and Reference examples in the presence of 0.1% (v/v) DMSO. The mouse TLR7 activity for the present compound was assessed by mouse TLR7 reporter gene assay, and the results are shown in Tables 5 and 6 as the compound concentration which produced half of the maximal level of SEAP induction (EC$_{50}$).

TABLE 5

| Example No. | EC$_{50}$ (nM) |
| --- | --- |
| 1 | 28 |
| 2 | 21 |

TABLE 6

| Reference example No. | EC$_{50}$ (nM) |
| --- | --- |
| 11 | 2 |
| 12 | 15 |

The results in Tests 1 and 2 suggest that the Example compounds and the Reference example compounds of the present invention can both act as human and mouse TLR7 agonists.

Test 3

Evaluation of In Vivo CTL Induction in HLA-A*24:02 Transgenic Mouse

The in vivo adjuvant activity of the compound of Example 1 and the compound of Reference example 12 was evaluated in the following procedure. To a cocktail vaccine comprising Compound of formula 4 prepared in Reference example 8 and Peptide SEQ ID No. 3 prepared in Reference example 3 with Montanide ISA 51 V (hereinafter, referred to as "cocktail vaccine b") was added the compound prepared in Example 1 or the compound prepared in Reference example 12 respectively to prepare each vaccine. The vaccine was administered to a HLA-A*24:02 transgenic mouse, and the adjuvant activity of each vaccine was evaluated by the method of testing antigen-specific cytotoxic T-lymphocyte (CTL) induction.

The CYTWNQMNL (SEQ ID No. 2) in Compound of formula 4 corresponds to an antigen peptide derived from an HLA-A*24:02-restricted WT1 protein.

HLA-A*24:02 transgenic mouse (C57BL/6CrHLA-A2402/$K^b$) expresses a chimeric HLA of a human MHC (HLA-A*24:02) and a mouse MHC (H-2$K^b$). The mouse can induce CTLs with a peptide which can induce CTLs in HLA-A*24:02-positive human (Int J Cancer. 2002; 100: 565-70).

The character for inducing CTLs specific to the peptide (SEQ ID No. 2) by cocktail vaccine b was evaluated by measuring whether IFNγ can be produced upon stimulation of splenocytes from the mouse with the peptide (SEQ ID No. 2). In addition, the character for exerting in vivo adjuvant activity by the compound in Example 1 or the compound in Reference example 12 was evaluated by comparing the number of CTLs induced by cocktail vaccine b and the number of CTLs induced by the vaccine prepared by adding the compound prepared in Example 1 or the compound in Reference example 12 to cocktail vaccine b, and checking presence or absence of the increase on the number.

Specifically, Compound of formula 4 and Peptide SEQ ID No. 3 were dissolved in DMSO, and then diluted with water for injection to concentrations of Compound of formula 4 of 6 mg/ml and Peptide of SEQ ID No. 3 of 4.5 mg/ml. The diluted peptide solution was mixed and emulsified with an equal volume of Montanide ISA 51 VG to prepare cocktail vaccine b. Cocktail vaccine b was injected to mice intradermally at the tail base area in an amount for administering 300 μg of Compound of formula 4 per body and 225 μg of Peptide SEQ ID No. 3 per body. Or, in the step of preparing cocktail vaccine b, the compound prepared in Example 1 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 100 ng of the compound prepared in Example 1 per body. Or, in the step of preparing cocktail vaccine b, the compound prepared in Reference example 12 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 69 ng of the compound prepared in Reference example 12 per body. The administrations were done twice, which had one week interval. One week after the final administration, the mice were sacrificed with $CO_2$ gas. Splenocytes were harvested from spleens removed from the mice. For detecting IFNγ-producing splenocytes, an IFNγ ELISPOT assay kit was used. In particular, an ELISPOT plate was treated with an anti-mouse-IFNγ antibody on the day before preparation of the splenocyte samples. On the next day, the plate was blocked by treatment with an RPMI 1640 medium with 10% fetal bovine serum (FBS). To the blocked ELISPOT plate, the splenocyte samples from the HLA-A*24:02 transgenic mice were added at $2.5 \times 10^5$ cells/well. Peptide (SEQ ID No. 2) was added in the presence of 0.1% (v/v) DMSO to the splenocyte-containing wells at a final concentration of 10 μg/ml. The peptide-added splenocyte was incubated overnight at 37° C. under an atmosphere of 5% $CO_2$ to re-stimulate the peptide in vitro. Then, after removal of the supernatant from the wells, stained spots on the ELISPOT plate were counted on ImmunoSpot Analyzer (C.T.L.).

FIG. 1 shows results from the IFNγ ELISPOT assay using the HLA-A*24:02 transgenic mouse. The scale on the vertical axis of the graph of FIG. 1 indicates the number of cells which produced IFNγ in response to the stimulation with the added cells. The vaccine administered to the mice is indicated on the horizontal axis. The black bars and the white bars in FIG. 1 show the results that the splenocyte from the HLA-A*24:02 transgenic mouse was incubated in the presence or absence of Peptide SEQ ID No. 2, respectively. Thus, the difference in the cell count between the black bar and the white bar shows the count of IFNγ-producing cells specific for Peptide SEQ ID No. 2 which was induced in the mouse's body by the administration of the vaccine, i.e., CTL count. The counts of the white bars in FIG. 1 were almost-imperceptible. It suggests that the splenocyte of the mouse reacted very little in the absence of the desired peptide. The results of the present test showed that cocktail vaccine b induced CTLs responsive to Peptide SEQ ID No. 2 in the HLA-A*24:02 transgenic mouse. And, the CTL counts responsive to Peptide SEQ ID No. 2 increased by adding the compound prepared in Example 1 or the compound prepared in Reference example 12 to cocktail vaccine b. In addition, the increase of the CTL counts was more in the case of adding the compound prepared in Example 1 to cocktail vaccine b, compared with the case of the compound prepared in Reference example 12.

The above results show that the induced CTL count increases by adding the compound prepared in Example 1 to the vaccine, and strongly suggest that the compound prepared in Example 1 has in vivo adjuvant activity. In addition, the results also show that the effect of increasing CTLs with the compound prepared in Example 1 is higher, compared with the case of the compound prepared in Reference example 12 which has no PEG structure.

Test 4

Evaluation of in vivo adjuvant activity in HLA-A*02:01 transgenic mouse

The in vivo adjuvant activity of the compound of Example 1 and the compound of Reference example 12 was evaluated in the following procedure. To a cocktail vaccine comprising Compound of formula 4 prepared in Reference example 8 and Peptide SEQ ID No. 3 prepared in Reference example 3 with a preliminarily-emulsified composition (hereinafter, referred to as "cocktail vaccine a") was added the compound prepared in Example 1 or the compound prepared in Reference example 12 respectively to prepare each vaccine. The vaccine was administered to a HLA-A*02:01 transgenic mouse, and the adjuvant activity of each vaccine was evaluated by the method of testing antigen-specific CTL induction.

Compound of formula 4:

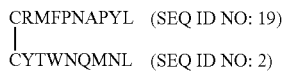

CRMFPNAPYL (SEQ ID NO: 19)
|
CYTWNQMNL (SEQ ID NO: 2)

wherein the bond between C-C is disulfide bond.

The RMFPNAPYL (SEQ ID No. 1) in Compound of formula 4 and the VLDFAPPGA (SEQ ID No. 4) in Peptide SEQ ID No. 3 correspond to antigen peptides derived from an HLA-A*02:01-restricted WT1 protein.

HLA-A*02:01 transgenic mouse (C57BL/6CrHLA-A2.1DR1) lacks mouse MHC, and instead expresses a chimeric HLA of a human MHC (HLA-A*02:01) and a mouse MHC (H-2D$^b$), and HLA-DRB1*01:01. The mouse can induce CTLs with a peptide which can induce CTLs in HLA-A*02:01-positive human (Eur J Immunol. 2, 004; 34: 3, 060-9).

The character for inducing CTLs specific to the antigen peptide (SEQ ID No. 1 or SEQ ID No. 4) by cocktail vaccine a was evaluated by measuring whether IFNγ can be produced upon stimulation of splenocytes from the mouse with the corresponding peptide. In addition, the character for exerting in vivo adjuvant activity by the compound in Example 1 or the compound in Reference example 12 was evaluated by comparing the number of CTLs induced by cocktail vaccine a and the number of CTLs induced by the vaccine prepared by adding the compound prepared in Example 1 or the compound in Reference example 12 to cocktail vaccine a, and checking presence or absence of the increase on the number.

Specifically, the in vivo adjuvant activity was evaluated as follows.

0.312 g of sodium dihydrogen phosphate dihydrate was dissolved in 80 g of water for injection. 14.0 g of ethyl oleate, 14.0 g of octyldodecyl myristate, 2.0 g of sorbitan monooleate, 2.8 g of glyceryl monooleate, 0.4 g of polyoxyethylene hydrogenated castor oil 20, and 0.4 g of glycerin were mixed. 2.354 mL of the mixture (corresponding to 2.077 g) was put into a test tube, and 0.396 mL of the aqueous sodium dihydrogen phosphate (corresponding to 0.396 g) was gradually added into the test tube which was being stirred with a mixer (ULTRA-TURRAX T10, IKA, or Touch Mixer MT-51, Yamato Scientific) to emulsify the mixture in the test tube. The obtained emulsion was referred to as preliminary emulsified composition. The amount of the preparation was adjusted as appropriate.

Compound of formula 4 and Peptide SEQ ID No. 3 were dissolved in DMSO, and then diluted with water for injection to concentrations of Compound of formula 4 of 3 mg/ml and Peptide of SEQ ID No. 3 of 2.25 mg/ml. The diluted peptide solution was mixed and emulsified with an equal volume of the above preliminary emulsified composition to prepare cocktail vaccine a. Cocktail vaccine a was injected to mice intradermally at the tail base area in an amount for administering 300 μg of Compound of formula 4 per body and 225 μg of Peptide SEQ ID No. 3 per body. Or, in the step of preparing cocktail vaccine a, the compound prepared in Example 1 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 32.5 ng of the compound prepared in Example 1 per body. Or, in the step of preparing cocktail vaccine a, the compound prepared in Reference example 12 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 22.5 ng of the compound prepared in Reference example 12 per body. One week later, the mice were sacrificed with $CO_2$ gas. Splenocytes were harvested from spleens removed from the mice. For detecting IFNγ-producing splenocytes, an IFNγ ELISPOT assay kit was used. In particular, an ELISPOT plate was treated with an anti-mouse-IFNγ antibody on the day before preparation of the splenocyte samples. On the next day, the plate was blocked by treatment with an RPMI 1640 medium with 10% FBS. To the blocked ELISPOT plate, the prepared splenocyte samples were added at 1.25×$10^5$ cells/well. Peptide (SEQ ID No. 1 or SEQ ID No. 4) was added in the presence of 0.1% (v/v) DMSO to the splenocyte-containing wells at a final concentration of 10 μg/ml. The peptide-added splenocyte was incubated overnight at 37° C. under an atmosphere of 5% $CO_2$ to re-stimulate the peptide in vitro. Then, after removal of the supernatant from the wells, the ELISPOT plate was subjected to treatment for cell staining in accordance with the manufacturer's protocol. Stained spots were counted on ImmunoSpot Analyzer.

The results show that cocktail vaccine a comprising Compound of formula 4 and Peptide SEQ ID No. 3 induced CTLs responsive to the peptide of SEQ ID No. 1 or SEQ ID No. 4 in the HLA-A*02:01 transgenic mouse. And, like the result of Test 3, the CTL counts responsive to Peptide of SEQ ID No. 1 or SEQ ID No. 4 were more in the case of adding the compound prepared in Example 1 to cocktail vaccine a, compared with the case of the compound prepared in Reference example 12.

The above results show that the induced CTL count increases by adding the compound prepared in Example 1 to the vaccine, and strongly suggest that the compound prepared in Example 1 has in vivo adjuvant activity. In addition, the results also show that the effect of increasing CTLs with the compound prepared in Example 1 is higher, compared with the case of the compound prepared in Reference example 12 which has no PEG structure.

Test 5

Effect for Enhancing the In Vivo Suppressive Effect of Vaccine for Growth of Tumor Vaccine A suspension of 3-methylcholanthrene in corn oil was administered to a HLA-A*24:02 transgenic mouse intradermally at the ventral region. From the tumor generated at the administration site, HLA-A*2402/Kb-expressing tumor cells were obtained. Cell lines established by stably expressing WT1 antigen peptide (SEQ ID No. 2) in the cells (herein, also referred to as MCA-A24/Kb-WT1 tumor cells) were suspended in Hanks' Balanced Salt Solution and intradermally transplanted to the ventral region of HLA-A*24:02 transgenic mouse (5×$10^5$ cells per mouse). The mice made to receive a vehicle (Group a), a vaccine (Group b), or a vaccine containing the compound prepared in Example 1 (Group c) were classified. Six mice per group were used. Seven days before the tumor transplantation and seven days after the tumor transplantation, for the mice of Group a, a composition comprising water for injection was emulsified with an equal volume of Montanide ISA 51 VG and the emulsion was administered intradermally at the tail base area (0.1 mL per administration per mouse). For the mice of Group b, a composition comprising Compound of formula 4 and Peptide SEQ ID No. 3 was emulsified with an equal volume of Montanide ISA 51 VG and the emulsion was administered intradermally at the tail base area (per administration, 300 μg of Compound of formula 4 per body and 225 μg of Peptide SEQ ID No. 3 per body). For the mice of Group c, a composition comprising Compound of formula 4, Peptide SEQ ID No. 3, and the compound prepared in Example 1 was emulsified with an equal volume of Montanide ISA 51 VG and the emulsion was administered intradermally at the tail base area (per administration, 300 μg of Compound of formula 4 per body, 225 μg of Peptide SEQ ID No. 3 per body, and 100 ng of the compound prepared in Example 1 per body). The tumor diameter was measured 27 days after the tumor transplantation and the tumor volume was calculated.

Figure 2:
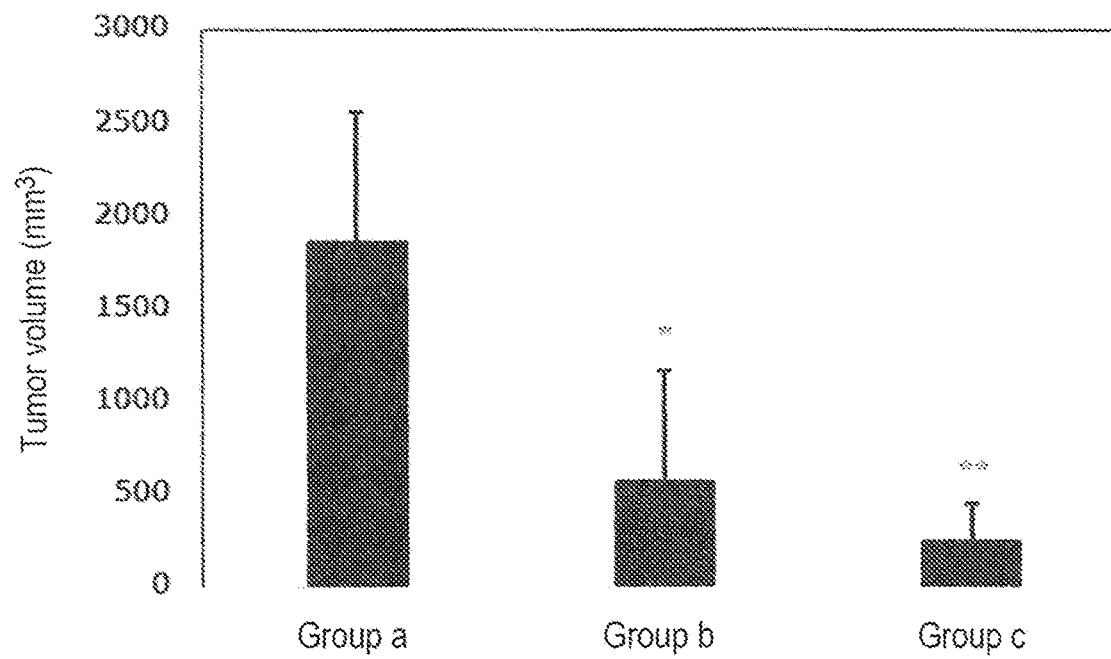
FIG. 2 shows the results of Test 5, i.e., a vaccine was prepared by adding the compound prepared in Example 1 to a cocktail vaccine comprising Compound of formula 4 and Peptide SEQ ID No. 3 with Montanide ISA 51 VG, and the vaccine was administered to the mouse; seven days before the tumor transplantation of MCA-A24/Kb-WT1 tumor cells to a HLA-A*24:02 transgenic mouse and seven days after the transplantation, the vaccine was administered to the mouse; and 27 days after the transplantation, the tumor volume was measured. The results are shown in FIG. 2.

FIG. 2 shows average tumor volumes of six mice in each group on the 27th day after the tumor transplantation. The vaccine (group b) significantly suppressed the growth of tumor cells, compared with the case of the vehicle (group a) (non-parametric Dunnett's multiple test, *: p<0.05). Further, the vaccine to which the compound prepared in Example 1 was added more potently suppressed the growth of tumor cells (group c, **: p<0.01)

The results show that the preventive effect for suppressing the growth of tumor with a vaccine can be enhanced by adding the present compound to the vaccine.

According to the method described in Reference example 1, the peptides shown in Table 7 were prepared as their trifluoroacetate from each corresponding starting material. These compounds were dealt as reference examples since they are not within the present compounds.

TABLE 7

| Reference example No. | SEQ ID No. | Amino acid sequence and Structure | LCMS Condition A (m/z, Retention time (min)) |
| --- | --- | --- | --- |
| 20 | 17 | KRYFKLSHLQMHSRKH | 420.2 $[M + 5H]^{+5}$, 0.64 |
| 21 | 18 | TYAGCLSQIF | 1102.5 $[M + H]^{+}$, 1.142 min |

According to the method described in WO 2007/0639032, the compound shown in Table 8 (wherein the bond between C—C is disulfide bond) was prepared as its trifluoroacetate. The compound was dealt as a reference example since it is not within the present compounds.

TABLE 8

| Reference example No. | Formula No. | Structure | LCMS Condition A (m/z, Retention time (min)) |
| --- | --- | --- | --- |
| 22 | 5 | C<br>\|<br>CYTWNQMNL<br>(SEQ ID NO: 2) | 1291.4 $[M + H]^{+}$, 1.051 min |

Test 6
Evaluation of In Vivo Adjuvant Activity in HLA-A*02:01 Transgenic Mouse

The in vivo adjuvant activity of the compound of Example 1 was evaluated in the following procedure. To a vaccine prepared by mixing Peptide SEQ ID No. 6 prepared in Reference example 6 with Montanide ISA 51 VG (hereinafter, referred to as "vaccine c") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction. The GLYDGMEHL in Peptide SEQ ID No. 6 corresponds to an antigen peptide derived from an HLA-A*02:01-restricted MAGE-A10 protein.

The character for inducing CTLs specific to the antigen peptide (SEQ ID No. 6) by vaccine c was evaluated by measuring whether IFNγ can be produced upon stimulation of splenocytes from the mouse with the peptide. In addition, the character for exerting in vivo adjuvant activity by the compound in Example 1 was evaluated by comparing the number of CTLs induced by vaccine c and the number of CTLs induced by the vaccine prepared by adding the compound prepared in Example 1 to vaccine c, and checking presence or absence of the increase on the number.

Specifically, Peptide of SEQ ID No. 6 was dissolved in DMSO, and then diluted with water for injection to concentrations of 0.1 mg/mL. The diluted peptide solution was mixed and emulsified with an equal volume of Montanide ISA 51 VG to prepare vaccine c. Vaccine c was injected to mice intradermally at the tail base area in an amount for administering 10 μg of Peptide of SEQ ID No. 6 per body. Or, in the step of preparing vaccine c, the compound prepared in Example 1 was added to the diluted peptide solution to prepare a vaccine, and the prepared vaccine was injected to mice intradermally at the tail base area in an amount for administering 10 μg of Peptide of SEQ ID No. 6 per body and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 6) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 3:
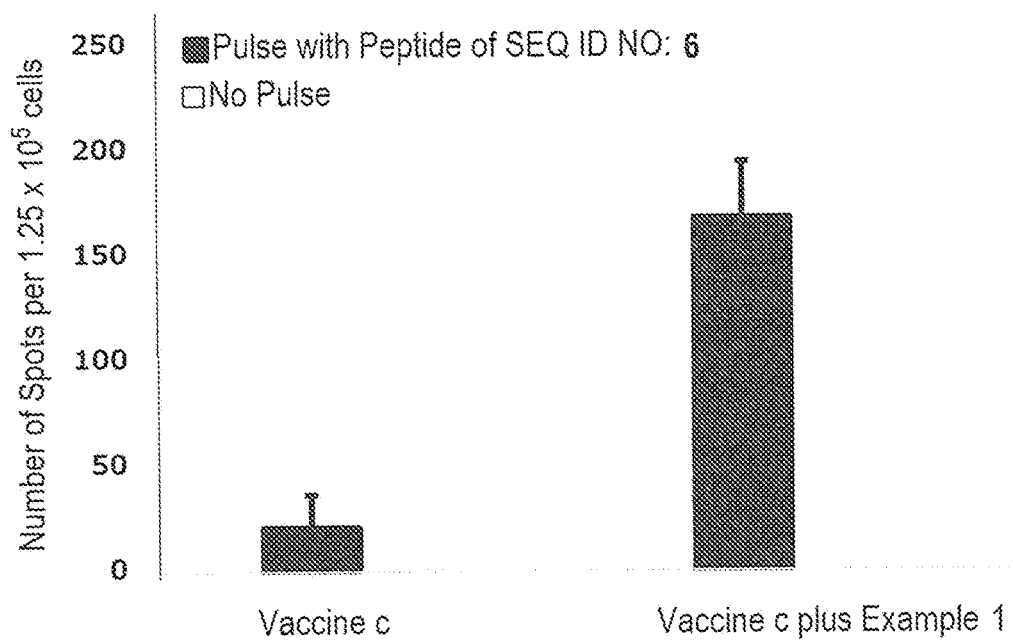
FIG. 3 shows the results of Test 6, i.e., a vaccine was prepared by adding the compound prepared in Example 1 to a vaccine comprising Peptide of SEQ ID No. 6 and Montanide ISA 51 VG; and the vaccine was tested about in vivo CTL induction for SEQ ID No. 6 with a HLA-A*02:01 transgenic mouse by IFNγ ELISPOT assay. The results are shown in FIG. 3.

The result was shown in FIG. 3. In FIG. 3, the vertical axis indicates the mean number of cells which produced IFNγ in response to the stimulation with the added cells, from each three mice per group. The vaccine administered to the mice is indicated on the horizontal axis. The black bars and the white bars in FIG. 3 show the results that the splenocyte from the HLA-A*02:01 transgenic mouse was incubated in the presence or absence of Peptide SEQ ID No. 6, respectively. The results of the present test showed that the CTL counts responsive to Peptide SEQ ID No. 6 were more in the case of adding the compound prepared in Example 1 to vaccine c, compared with the case of adding no compound.

The above results show that the induced CTL count increases by adding the compound prepared in Example 1 to the vaccine, and strongly suggest that the compound prepared in Example 1 has in vivo adjuvant activity.

Test 7
Evaluation of In Vivo Adjuvant Activity in HLA-A*02:01 Transgenic Mouse

The in vivo adjuvant activity of the compound of Example 1 was evaluated in the following procedure. To a vaccine prepared by mixing Peptide SEQ ID No. 5 prepared in Reference example 5 with Montanide ISA 51 VG (hereinafter, referred to as "vaccine d") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction. The VLQELNVTV in Peptide SEQ ID No. 5 corresponds to an antigen peptide derived from an HLA-A*02:01-restricted Proteinase-3 protein.

The character for inducing CTLs specific to the antigen peptide (SEQ ID No. 5) by vaccine d was evaluated by measuring whether IFNγ can be produced upon stimulation of splenocytes from the mouse with the peptide. In addition, the character for exerting in vivo adjuvant activity by the compound in Example 1 was evaluated by comparing the number of CTLs induced by vaccine d and the number of CTLs induced by the vaccine prepared by adding the compound prepared in Example 1 to vaccine d, and checking presence or absence of the increase on the number.

Specifically, Peptide of SEQ ID No. 5 was dissolved in DMSO, and then diluted with water for injection to concentrations of 2 mg/mL. The diluted peptide solution was mixed and emulsified with an equal volume of Montanide ISA 51 VG to vaccine d. Vaccine d was injected to mice intradermally at the tail base area in an amount for administering 100 μg of Peptide of SEQ ID No. 5 per body. Or, in the step of preparing vaccine d, the compound prepared in Example 1 was added to the diluted peptide solution to prepare a vaccine, and the prepared vaccine was injected to mice intradermally at the tail base area in an amount for administering 100 μg of Peptide of SEQ ID No. 5 per body and 330 ng of the compound prepared in Example 1 per body. One week later, the mice were sacrificed with $CO_2$ gas. Splenocytes were harvested from spleens removed from the mice. Like Test 4, Peptide (SEQ ID No. 5) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 4:
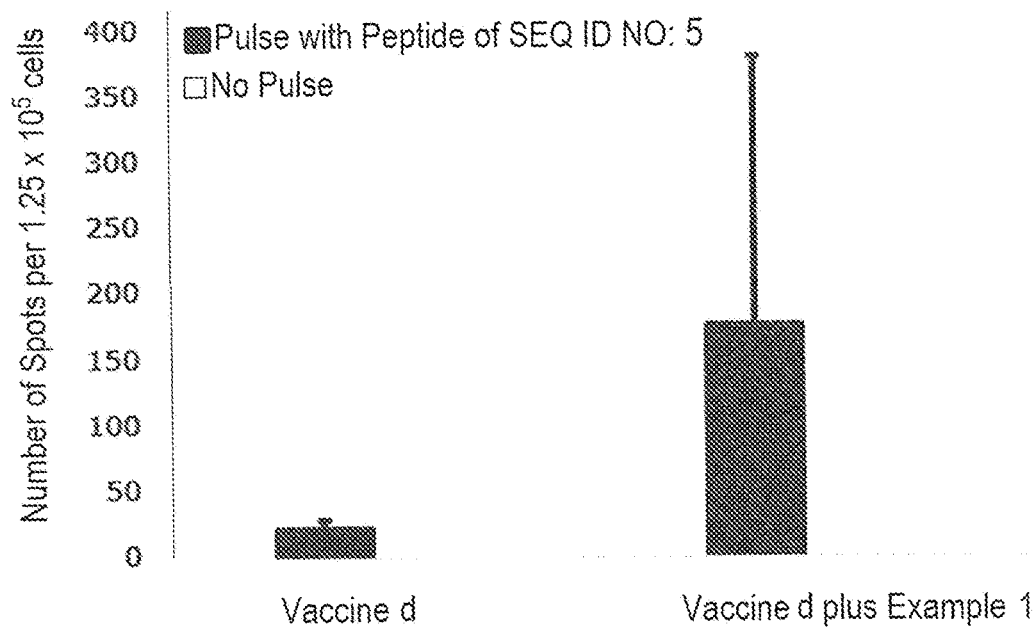
FIG. 4 shows the results of Test 7, i.e., a vaccine was prepared by adding the compound prepared in Example 1 to a vaccine comprising Peptide of SEQ ID No. 5 and Montanide ISA 51 VG; and the vaccine was tested about in vivo CTL induction for SEQ ID No. 5 with a HLA-A*02:01 transgenic mouse by IFNγ ELISPOT assay. The results are shown in FIG. 4.

The result was shown in FIG. 4. In FIG. 4, the vertical axis indicates the mean number of cells which produced IFNγ in response to the stimulation with the added cells, from each three mice per group. The vaccine administered to the mice is indicated on the horizontal axis. The black bars and the white bars in FIG. 4 show the result that the splenocyte from the HLA-A*02:01 transgenic mouse was incubated in the presence or absence of Peptide SEQ ID No. 5, respectively. The results of the present test showed that the CTL counts responsive to Peptide of SEQ ID No. 5 were more in the case of adding the compound prepared in Example 1 to vaccine d, compared with the case of adding no compound.

The above results show that the induced CTL count increases by adding the compound prepared in Example 1 to the vaccine, and strongly suggest that the compound prepared in Example 1 has in vivo adjuvant activity.

Test 8
Evaluation of In Vivo Adjuvant Activity in HLA-A*24:02 Transgenic Mouse

The in vivo adjuvant activity of the compound of Example 1 was evaluated in the following procedure. To a vaccine prepared by mixing Peptide SEQ ID No. 18 prepared in Reference example 20 with Montanide ISA 51 VG (hereinafter, referred to as "vaccine e") was added the compound prepared in Example 1 to prepare a vaccine. The vaccine was administered to a HLA-A*24:02 transgenic mouse, and the adjuvant activity of the vaccine was evaluated by the method of testing antigen-specific CTL induction. The TYAGCLSQIF in Peptide SEQ ID No. 18 corresponds to an antigen peptide derived from an HLA-A*24:02-restricted Or7c1 protein.

The character for inducing CTLs specific to the antigen peptide (SEQ ID No. 18) by vaccine e was evaluated by measuring whether IFNγ can be produced upon stimulation of splenocytes from the mouse with the peptide. In addition, the character for exerting in vivo adjuvant activity by the compound in Example 1 was evaluated by comparing the number of CTLs induced by vaccine e and the number of CTLs induced by the vaccine prepared by adding the compound prepared in Example 1 to vaccine e, and checking presence or absence of the increase on the number.

Specifically, Peptide of SEQ ID No. 18 was dissolved in DMSO, and then diluted with water for injection to concentrations of 3 mg/mL. The diluted peptide solution was mixed and emulsified with an equal volume of Montanide ISA 51 VG to prepare vaccine e. Vaccine e was injected to mice intradermally at the tail base area in an amount for administering 300 μg of Peptide of SEQ ID No. 18 per body. Or, in the step of preparing vaccine e, the compound prepared in Example 1 was added to the diluted peptide solution to prepare a vaccine, and the prepared vaccine was injected to mice intradermally at the tail base area in an amount for administering 300 μg of Peptide of SEQ ID No. 18 per body and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 3, Peptide (SEQ ID No. 18) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 5:
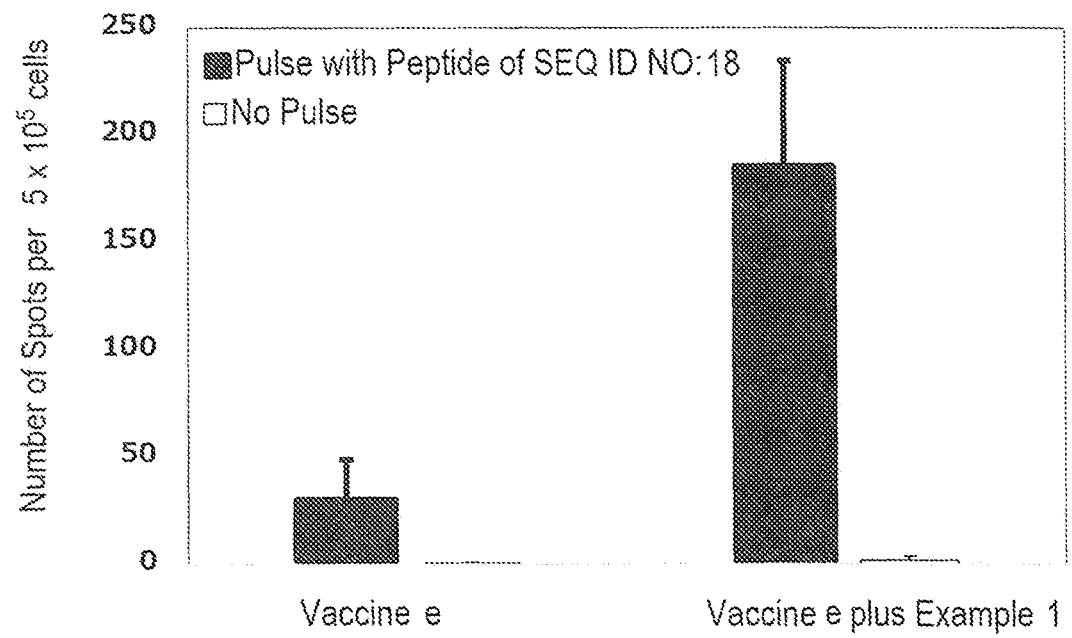
FIG. 5 shows the results of Test 8, i.e., a vaccine was prepared by adding the compound prepared in Example 1 to a vaccine comprising Peptide of SEQ ID No. 18 and Montanide ISA 51 VG; and the vaccine was tested about in vivo CTL induction for SEQ ID No. 18 with a HLA-A*24:02 transgenic mouse by IFNγ ELISPOT assay. The results are shown in FIG. 5.

The result was shown in FIG. 5. In FIG. 5, the vertical axis indicates the mean number of cells which produced IFNγ in response to the stimulation with the added cells, from each three mice per group. The vaccine administered to the mice is indicated on the horizontal axis. The black bars and the white bars in FIG. 5 show the result that the splenocyte from the HLA-A*24:02 transgenic mouse was incubated in the presence or absence of Peptide SEQ ID No. 18, respectively. The results of the present test showed that the CTL counts responsive to Peptide of SEQ ID No. 18 were more in the case of adding the compound prepared in Example 1 to vaccine e, compared with the case of adding no compound.

The above results show that the induced CTL count increases by adding the compound prepared in Example 1 to the vaccine, and strongly suggest that the compound prepared in Example 1 has in vivo adjuvant activity.

Test 9
Evaluation of In Vivo Adjuvant Activity in HLA-A*02:01 Transgenic Mouse

The in vivo adjuvant activity of the compounds prepared in Examples 8, 9, and 10 and the compound prepared in Reference example 12 was evaluated in the following procedure. To cocktail vaccine b comprising Compound of formula 4 prepared in Reference example 8 and Peptide SEQ ID No. 3 prepared in Reference example 3 with Montanide ISA51 VG was added the compound prepared in Example 8, 9, or 10, or the compound prepared in Reference example 12 to prepare each vaccine. The vaccine was administered to a HLA-A*02:01 transgenic mouse, and the adjuvant activity of each vaccine was evaluated by the method of testing antigen-specific CTL induction.

Specifically, Compound of formula 4 and Peptide SEQ ID No. 3 were dissolved in DMSO, and then diluted with water for injection to concentrations of Compound of formula 4 of 3 mg/mL and Peptide SEQ ID No. 3 of 2.25 mg/mL. The diluted peptide solution was mixed and emulsified with an equal volume of Montanide ISA 51 VG to prepare cocktail vaccine b. Cocktail vaccine b was injected to mice intradermally at the tail base area in an amount for administering 300 μg of Compound of formula 4 per body and 225 μg of Peptide SEQ ID No. 3 per body. Or, in the step of preparing cocktail vaccine b, the compound prepared in Example 8, 9, or 10, or the compound prepared in Reference example 12 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 0.4 nmol of the compound prepared in Example 8, 9, or 10, or the compound prepared in Reference example 12 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 6:
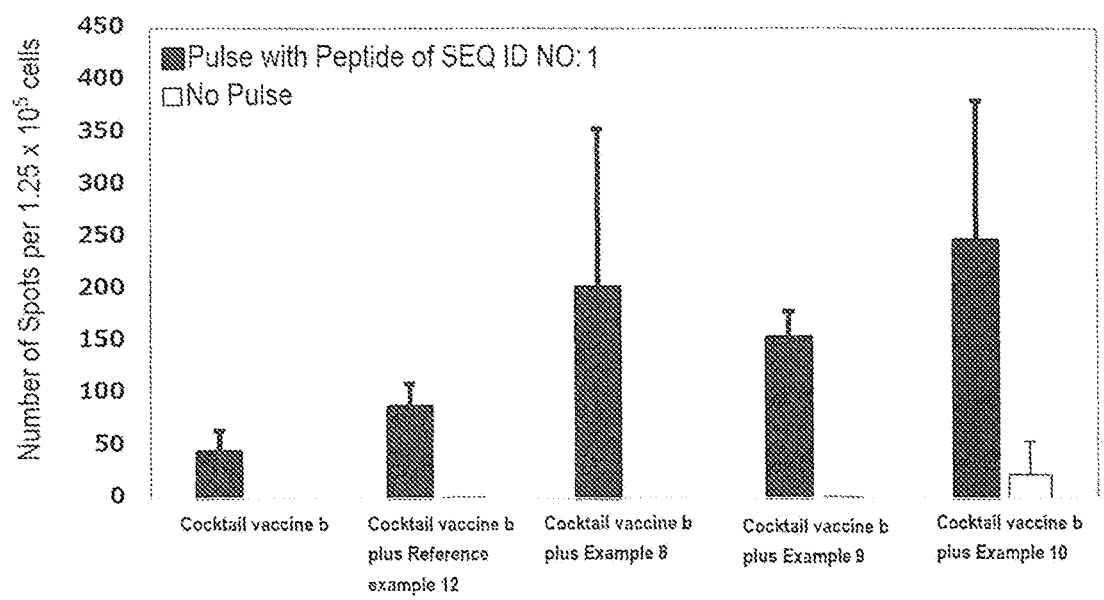
FIG. 6 shows the results of Test 9, i.e., a vaccine was prepared by adding the compound prepared in Example 8, 9, or 10 or the compound prepared in Reference example 12 to a cocktail vaccine comprising Compound of formula 4 and Peptide SEQ ID No. 3 with Montanide ISA 51 VG; and each vaccine was tested about in vivo CTL induction for SEQ ID No. 1 with a HLA-A*02:01 transgenic mouse by IFNγ ELISPOT assay. The results are shown in FIG. 6.
Figure 7:
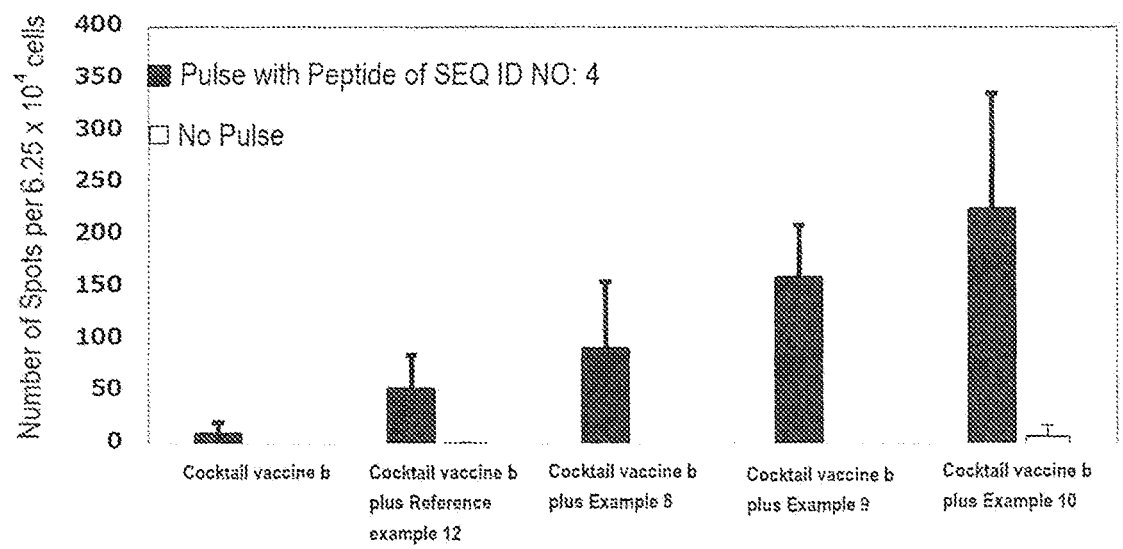
FIG. 7 shows the results of Test 9, i.e., a vaccine was prepared by adding the compound prepared in Example 8, 9, or 10 or the compound prepared in Reference example 12 to a cocktail vaccine comprising Compound of formula 4 and Peptide SEQ ID No. 3 with Montanide ISA 51 VG; and each vaccine was tested about in vivo CTL induction for SEQ ID No. 4 with a HLA-A*02:01 transgenic mouse by IFNγ ELISPOT assay. The results are shown in FIG. 7.

The results were shown in FIG. 6 and FIG. 7. The results of the present test showed that the CTL counts responsive to the peptide were more in the case of adding the compound prepared in Example 8, 9, or 10 or the compound prepared in Reference example 12 to cocktail vaccine b, compared with the case of adding no compound. In addition, the results showed that the CTL counts responsive to the peptide in the case of adding the compound prepared in Example 8, 9, or 10 is more, compared with the case of the compound prepared in Reference example 12.

The above results show that the induced CTL count increases by adding the compound prepared in Example 8, 9, or 10 to the vaccine, and strongly suggest that the compound prepared in Example 8, 9, or 10 has in vivo adjuvant activity. In addition, the results also show that the effect of increasing CTLs with the compound prepared in Example 8, 9, or 10 is higher, compared with the case of the compound prepared in Reference example 12 which has no PEG structure.

Test 10
Evaluation of In Vivo Adjuvant Activity in HLA-A*02:01 Transgenic Mouse

The in vivo adjuvant activity of the compound of Example 11 was evaluated in the following procedure. To cocktail vaccine b like Test 9 was added the compound prepared in Example 11 to prepare a vaccine. The vaccine was administered to a HLA-A*02:01 transgenic mouse, and the adjuvant activity of the vaccine was evaluated by the method of testing antigen-specific CTL induction.

Specifically, Compound of formula 4 and Peptide SEQ ID No. 3 were dissolved in DMSO, and then diluted with water for injection to concentrations of Compound of formula 4 of 3 mg/mL and Peptide SEQ ID No. 3 of 2.25 mg/mL. The diluted peptide solution was mixed and emulsified with an equal volume of Montanide ISA 51 VG to prepare cocktail vaccine b. Cocktail vaccine b was injected to mice intradermally at the tail base area in an amount for administering 300 μg of Compound of formula 4 per body and 225 μg of Peptide SEQ ID No. 3 per body. Or, in the step of preparing cocktail vaccine b, the compound prepared in Example 11 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 0.4 nmol of the compound prepared in Example 11 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 8:
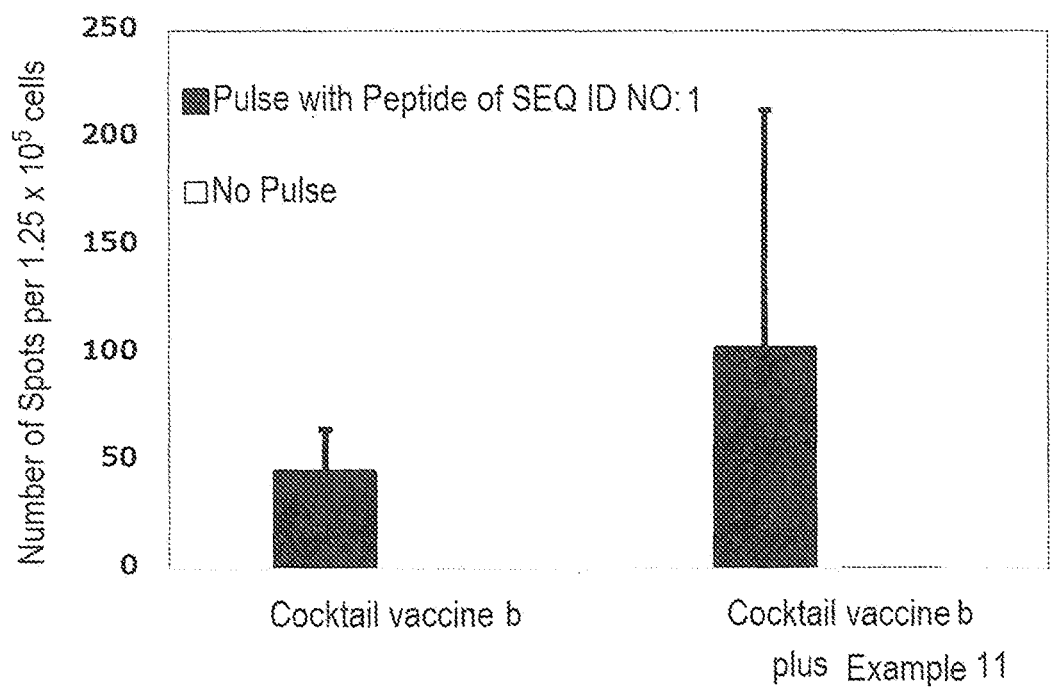
FIG. 8 shows the results of Test 10, i.e., a vaccine was prepared by adding the compound prepared in Example 11 to a cocktail vaccine comprising Compound of formula 4 and Peptide SEQ ID No. 3 with Montanide ISA 51 VG; and the vaccine was tested about in vivo CTL induction for SEQ ID No. 1 with a HLA-A*02:01 transgenic mouse by IFNγ ELISPOT assay. The results are shown in FIG. 8.
Figure 9:
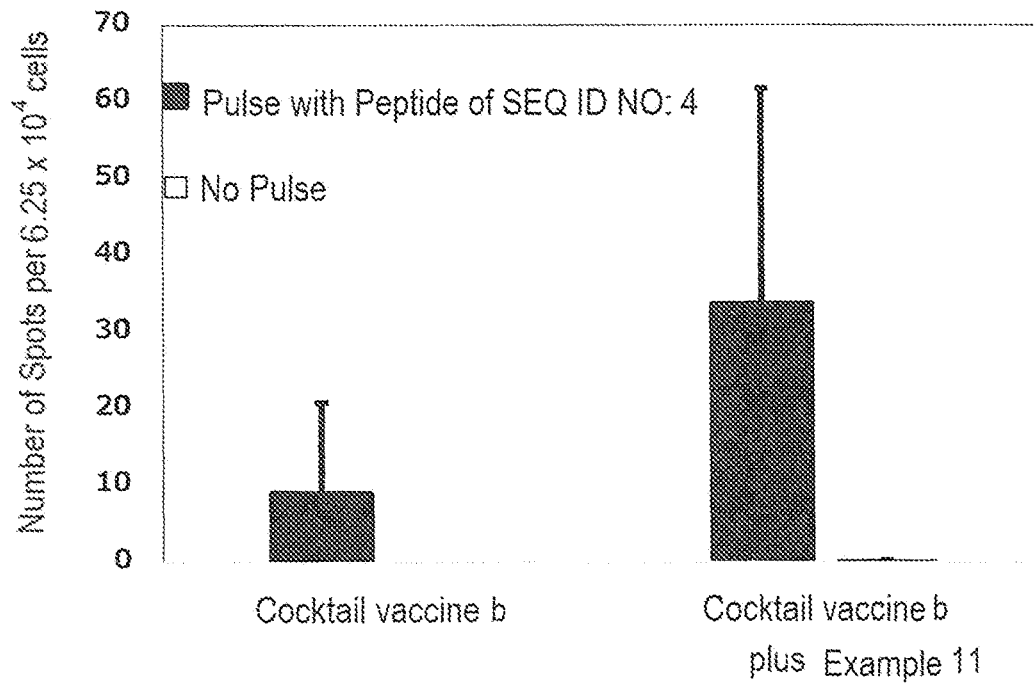
FIG. 9 shows the results of Test 10, i.e., a vaccine was prepared by adding the compound prepared in Example 11 to a cocktail vaccine comprising Compound of formula 4 and Peptide SEQ ID No. 3 with Montanide ISA 51 VG; and the vaccine was tested about in vivo CTL induction for SEQ ID No. 4 with a HLA-A*02:01 transgenic mouse by IFNγ ELISPOT assay. The results are shown in FIG. 9.

The result was shown in FIG. 8 and FIG. 9. The results of the present test showed that the CTL counts responsive to Peptide SEQ ID No. 1 or SEQ ID No. 4 were more in the case of adding the compound prepared in Example 11 to cocktail vaccine b, compared with the case of adding no compound.

The above results show that the induced CTL count increases by adding the compound prepared in Example 11 to the vaccine, and strongly suggest that the compound prepared in Example 11 has in vivo adjuvant activity.

Test 11
Evaluation of In Vivo Adjuvant Activity in HLA-A*02:01 Transgenic Mouse

The in vivo adjuvant activity of the compound of Example 1 was evaluated in the following procedure. To a cocktail vaccine (emulsified composition 1) comprising Compound of formula 4 prepared in Reference example 8 and Peptide SEQ ID No. 3 prepared in Reference example 3 (hereinafter, referred to as "cocktail vaccine f") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above emulsified composition 1 was prepared as follows. 95.8% (w/w) of soybean oil, 3% (w/w) of PEG-30 dipolyhydroxy stearate, and 1.2% (w/w) of polysorbate 80 were mixed to prepare an oil-phase mixture. The amount of the preparation was adjusted as appropriate. Compound of formula 4 and Peptide SEQ ID No. 3 were mixed with pH 2.5 buffer (10 mM tartaric acid, 10% trehalose) to adjust each concentration to 3 mg/mL and 2.25 mg/mL, respectively. The prepared peptide dilution was mixed with an equal volume of the oil-phase mixture to give an emulsified product, cocktail vaccine f. Cocktail vaccine f was injected to mice intradermally at the tail base area in an amount for administering 300 μg of Compound of formula 4 per body and 225 μg of Peptide SEQ ID No. 3 per body. Or, in the step of preparing cocktail vaccine f, the compound prepared in Example 1 was added to the diluted peptide solution to prepare a vaccine, and the prepared vaccine was injected to mice intradermally at the tail base area in an amount for administering 300 μg of Compound of formula 4 per body, 225 μg of Peptide SEQ ID No. 3 per body, and 0.04 nmol or 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 10:
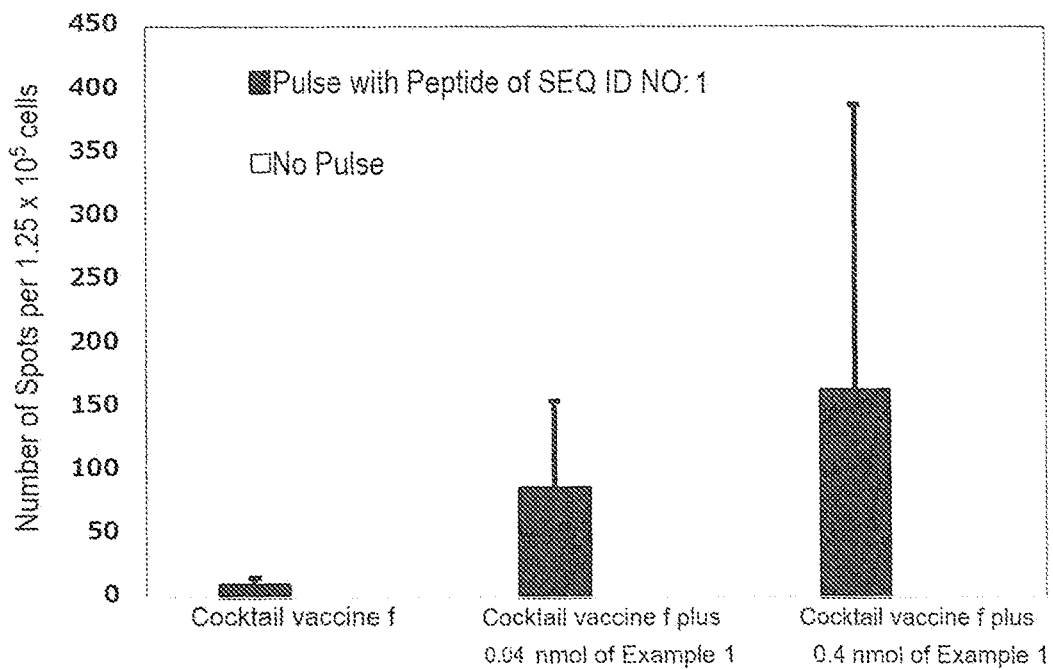
FIG. 10 shows the results of Test 11, i.e., a vaccine was prepared by adding the compound prepared in Example 1 to a cocktail vaccine (emulsified composition 1) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 10.
Figure 11:
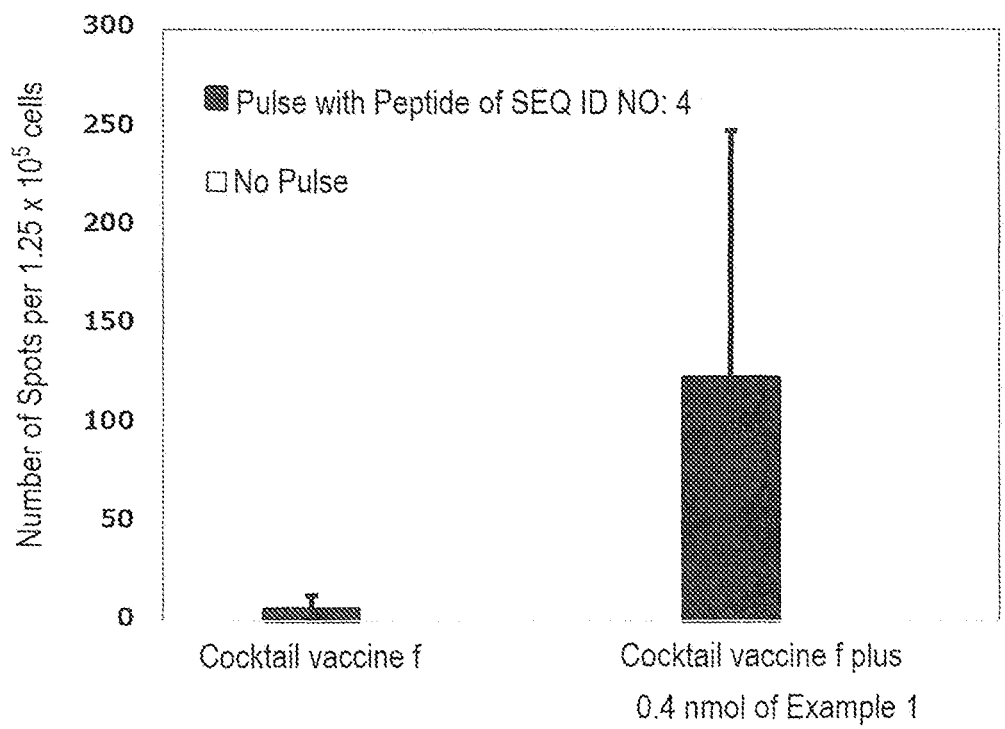
FIG. 11 shows the results of Test 11, i.e., a vaccine was prepared by adding the compound prepared in Example 1 to a cocktail vaccine (emulsified composition 1) comprising Compound of formula 4 and Peptide SEQ ID No. 3; and the vaccine was tested about in vivo CTL induction for SEQ ID No. 4 with a HLA-A*02:01 transgenic mouse by IFNγ ELISPOT assay. The results are shown in FIG. 11.

The result was shown in FIG. 10 and FIG. 11. The results of the present test showed that the CTL counts responsive to Peptide SEQ ID No. 1 or SEQ ID No. 4 were more in the case of adding the compound prepared in Example 1 to cocktail vaccine f, compared with the case of adding no compound.

The above results show that the induced CTL count increases by adding the compound prepared in Example 1 to the vaccine, and strongly suggest that the compound prepared in Example 1 has in vivo adjuvant activity.

Test 12
Evaluation of In Vivo Adjuvant Activity in HLA-A*02:01 Transgenic Mouse

The in vivo adjuvant activity of the compound of Example 1 was evaluated in the following procedure. To a cocktail vaccine (emulsified composition 2) comprising Compound of formula 4 prepared in Reference example 8 and Peptide SEQ ID No. 3 prepared in Reference example 3 (hereinafter, referred to as "cocktail vaccine g") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above emulsified composition 2 was prepared as follows. 95.8% (w/w) of medium-chain triglyceride (MYGLYOL 812), 3% (w/w) of PEG-30 dipolyhydroxy stearate, and 1.2% (w/w) of polysorbate 80 were mixed to prepare an oil-phase mixture. The amount of the preparation was adjusted as appropriate. Compound of formula 4 and Peptide SEQ ID No. 3 were mixed with pH 2.5 buffer (10 mM tartaric acid, 10% trehalose) to adjust each concentration to 3 mg/mL and 2.25 mg/mL, respectively. The prepared peptide dilution was mixed with an equal volume of the oil-phase mixture to give an emulsified product, cocktail vaccine g. Cocktail vaccine g was injected to mice intradermally at the tail base area in an amount for administering 300 µg of Compound of formula 4 per body and 225 µg of Peptide SEQ ID No. 3 per body. Or, in the step of preparing cocktail vaccine g, the compound prepared in Example 1 was added to the diluted peptide solution to prepare a vaccine, and the prepared vaccine was injected to mice intradermally at the tail base area in an amount for administering 300 µg of Compound of formula 4 per body, 225 µg of Peptide SEQ ID No. 3 per body, and 0.04 nmol or 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 µg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 12:
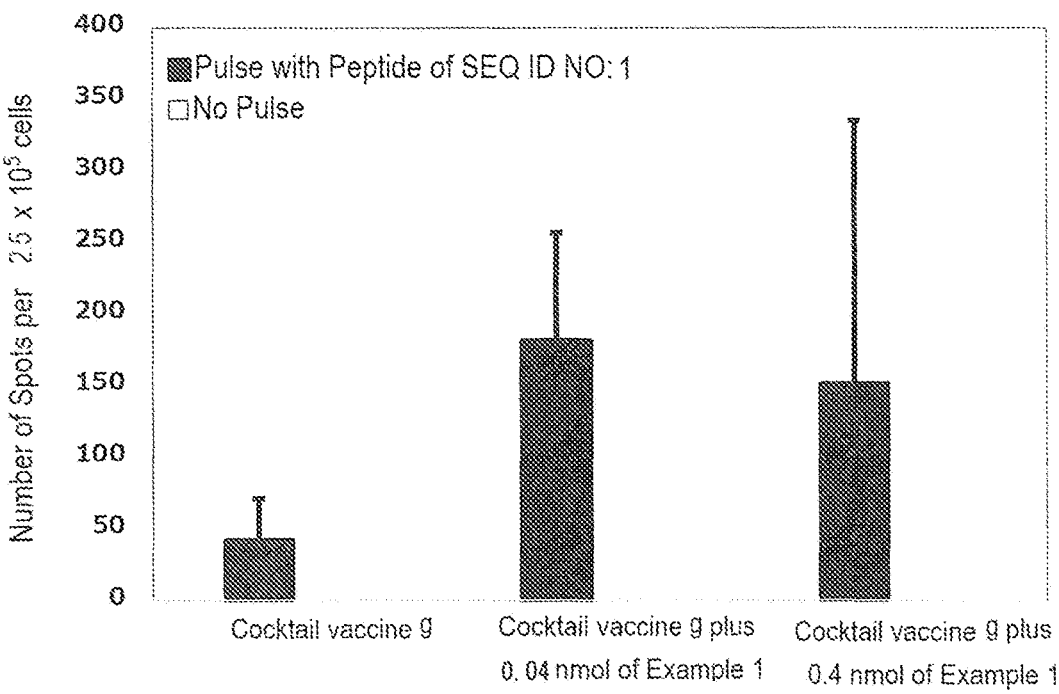
FIG. 12 shows the results of Test 12, i.e., a vaccine was prepared by adding the compound prepared in Example 1 to a cocktail vaccine (emulsified composition 2) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 12.
Figure 13:
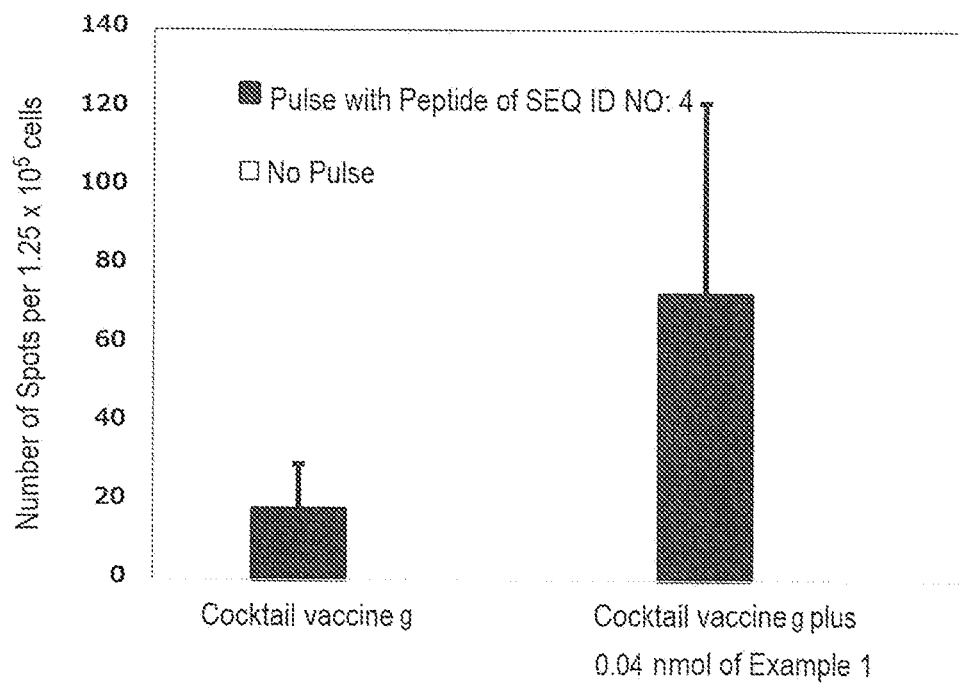
FIG. 13 shows the results of Test 12, i.e., a vaccine was prepared by adding the compound prepared in Example 1 to a cocktail vaccine (emulsified composition 2) comprising Compound of formula 4 and Peptide SEQ ID No. 3; and the vaccine was tested about in vivo CTL induction for SEQ ID No. 4 with a HLA-A*02:01 transgenic mouse by IFNγ ELISPOT assay. The results are shown in FIG. 13.

The results were shown in FIG. 12 and FIG. 13. The results of the present test showed that the CTL counts responsive to Peptide SEQ ID No. 1 or SEQ ID No. 4 were more in the case of adding the compound prepared in Example 1 to cocktail vaccine g, compared with the case of adding no compound.

The above results show that the induced CTL count increases by adding the compound prepared in Example 1 to the vaccine, and strongly suggest that the compound prepared in Example 1 has in vivo adjuvant activity.

Test 13
Evaluation of In Vivo Adjuvant Activity in HLA-A*02:01 Transgenic Mouse

The in vivo adjuvant activity of the compound of Example 1 was evaluated in the following procedure. To a cocktail vaccine (emulsified composition 3) comprising Compound of formula 4 prepared in Reference example 8 and Peptide SEQ ID No. 3 prepared in Reference example 3 (hereinafter, referred to as "cocktail vaccine h") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above emulsified composition 3 was prepared as follows. 95.8% (w/w) of isopropyl myristate, 3% (w/w) of PEG-30 dipolyhydroxy stearate, and 1.2% (w/w) of polysorbate 80 were mixed to prepare an oil-phase mixture. The amount of the preparation was adjusted as appropriate. Compound of formula 4 and Peptide SEQ ID No. 3 were mixed with pH 2.5 buffer (10 mM tartaric acid, 10% trehalose) to adjust each concentration to 3 mg/mL and 2.25 mg/mL, respectively. The prepared peptide dilution was mixed with an equal volume of the oil-phase mixture to give an emulsified product, cocktail vaccine h. Cocktail vaccine h was injected to mice intradermally at the tail base area in an amount for administering 300 µg of Compound of formula 4 per body and 225 µg of Peptide SEQ ID No. 3. Or, in the step of preparing cocktail vaccine h, the compound prepared in Example 1 was added to the diluted peptide solution to prepare a vaccine, and the prepared vaccine was injected to mice intradermally at the tail base area in an amount for administering 300 µg of Compound of formula 4 per body, 225 µg of Peptide SEQ ID No. 3, and 0.04 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1) was added to the splenocyte-containing ELISPOT plate at a final concentration of 10 µg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 14:
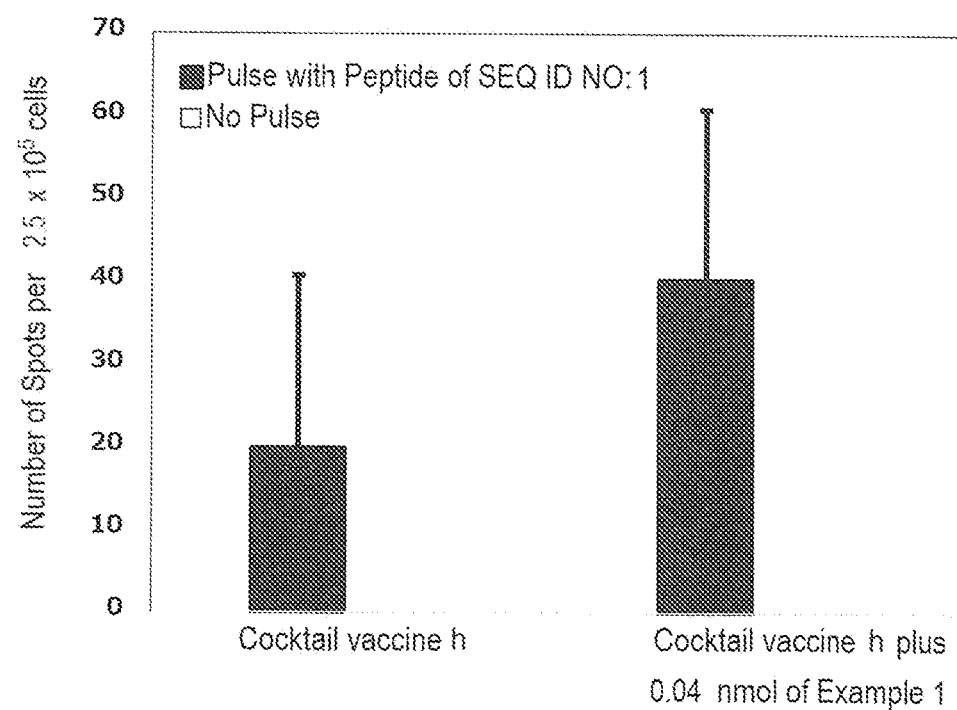
FIG. 14 shows the results of Test 13, i.e., a vaccine was prepared by adding the compound prepared in Example 1 to a cocktail vaccine (emulsified composition 3) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 14.

The result was shown in FIG. 14. The results of the present test showed that the CTL counts responsive to Peptide SEQ ID No. 1 were more in the case of adding the compound prepared in Example 1 to cocktail vaccine h, compared with the case of adding no compound.

The above results show that the induced CTL count increases by adding the compound prepared in Example 1 to the vaccine, and strongly suggest that the compound prepared in Example 1 has in vivo adjuvant activity.

Figure 26:
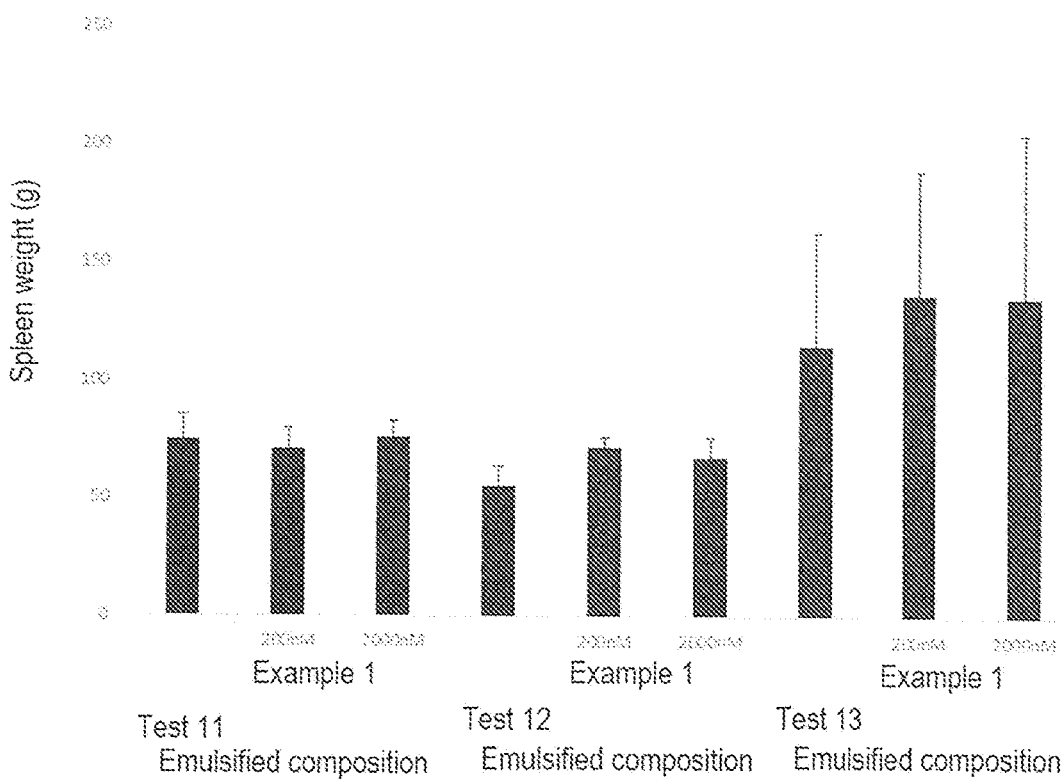
FIG. 26 shows the results of Tests 11-13, i.e., a composition comprising Compound of formula 4 and Peptide SEQ ID No. 3 was emulsified to prepare a cocktail vaccine; the compound prepared in Example 1 was added to the cocktail vaccine to prepare a vaccine; the vaccine was administered to the mouse; and the mouse's spleen was weighed. The results are shown in FIG. 26.

FIG. 26 shows the results of each spleen weight in the mice tested in Tests 11-13. The present results show that the administration of Example 1 does not induce a pronounced increase of spleen weight, and suggest that the compound prepared in Example 1 has in vivo adjuvant activity without causing splenomegaly.

Test 14
Evaluation of In Vivo Adjuvant Activity in HLA-A*02:01 Transgenic Mouse

The in vivo adjuvant activity of the compound of Example 1 was evaluated in the following procedure. To a cocktail vaccine (oily suspension formulation) comprising Compound of formula 4 prepared in Reference example 8 and Peptide SEQ ID No. 3 prepared in Reference example 3 (hereinafter, referred to as "cocktail vaccine i") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above oily suspension formulation was prepared as follows. Sucrose fatty acid ester (RYOTO SUGAR ESTER L-195) was dissolved in cyclohexane to adjust the concentration to 12.5 mg/mL, and then Compound of formula 4 and Peptide SEQ ID No. 3 were added to the solution to adjust each concentration to 0.75 mg/mL and 0.5625 mg/mL to give an oil-phase mixture. pH 2.5 Buffer (10 mM tartaric acid, 10% trehalose) was added to the oil-phase mixture by 1 mL for 2 mL of the oil-phase mixture, and the mixture was dispersed with a homogenizer and lyophilized. To the lyophilized product was added 1 mL of isopropyl myristate to give an oily suspension formulation, cocktail vaccine i. The amount of the preparation was adjusted as appropriate.

Cocktail vaccine i was injected to mice intradermally at the tail base area in an amount for administering 300 μg of Compound of formula 4 per body and 225 μg of Peptide SEQ ID No. 3 per body. Or, in the step of preparing cocktail vaccine i, the compound prepared in Example 1 was added to the pH 2.5 buffer to prepare a vaccine, and the prepared vaccine was injected to mice intradermally at the tail base area in an amount for administering 300 μg of Compound of formula 4 per body, 225 μg of Peptide SEQ ID No. 3 per body, and 0.04 nmol or 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 15:
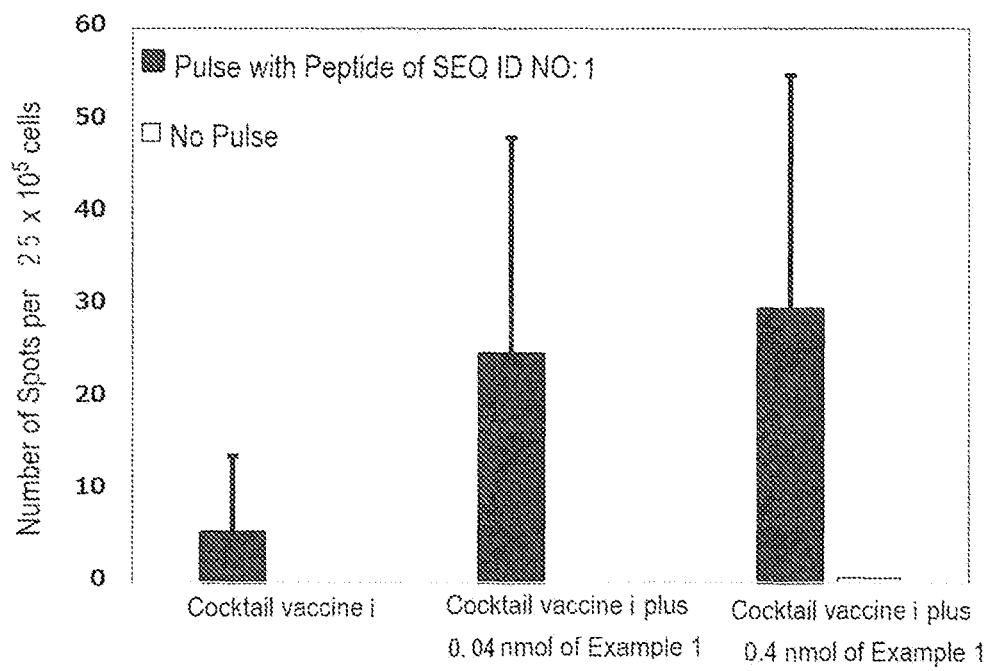
FIG. 15 shows the results of Test 14, i.e., a vaccine was prepared by adding the compound prepared in Example 1 to a cocktail vaccine (oily suspension formulation) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 15.
Figure 16:
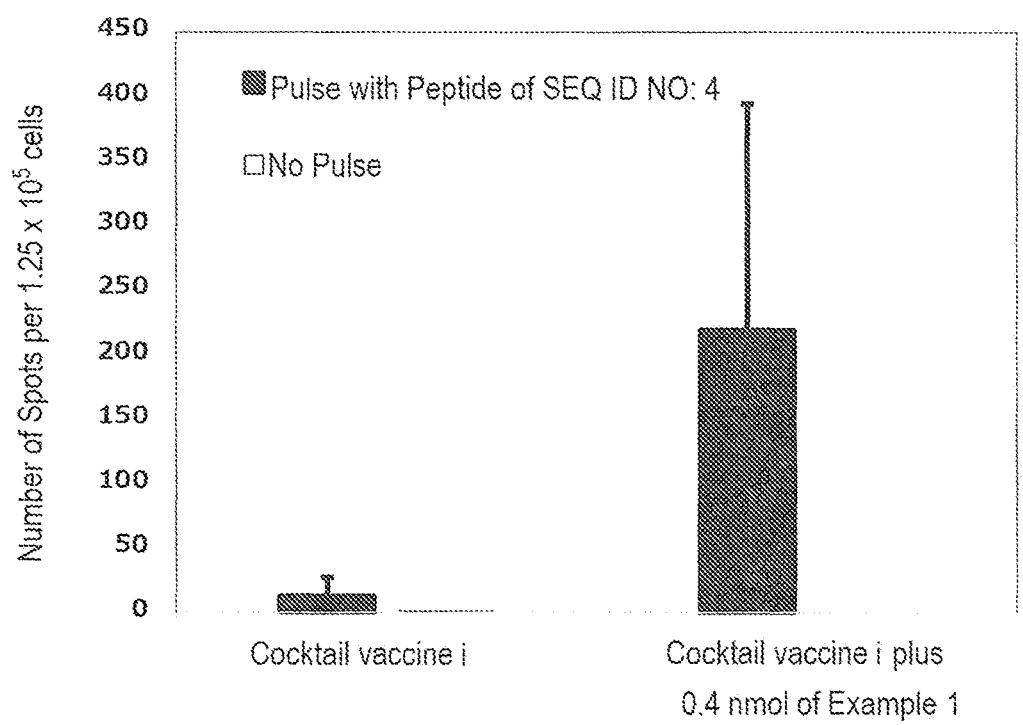
FIG. 16 shows the results of Test 14, i.e., a vaccine was prepared by adding the compound prepared in Example 1 to a cocktail vaccine (oily suspension formulation) comprising Compound of formula 4 and Peptide SEQ ID No. 3; and the vaccine was tested about in vivo CTL induction for SEQ ID No. 4 with a HLA-A*02:01 transgenic mouse by IFNγ ELISPOT assay. The results are shown in FIG. 16.

The result was shown in FIG. 15 and FIG. 16. The results of the present test showed that the CTL counts responsive to Peptide SEQ ID No. 1 or SEQ ID No. 4 were more in the case of adding the compound prepared in Example 1 to cocktail vaccine i, compared with the case of adding no compound.

The above results show that the induced CTL count increases by adding the compound prepared in Example 1 to the vaccine, and strongly suggest that the compound prepared in Example 1 has in vivo adjuvant activity.

Test 15
Evaluation of In Vivo Adjuvant Activity in HLA-A*02:01 Transgenic Mouse

The in vivo adjuvant activity of the compound of Example 1 was evaluated in the following procedure. To a vaccine (hydrogel formulation) comprising Compound of formula 4 prepared in Reference example 8 and Peptide SEQ ID No. 3 prepared in Reference example 3 (hereinafter, referred to as "cocktail vaccine j") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above hydrogel formulation was prepared as follows. Compound of formula 4, Peptide SEQ ID No. 3, and polyoxyethylene(196)polyoxypropylene(67) glycol were mixed with pH 2.5 buffer (10 mM tartaric acid) to adjust each concentration to 1.5 mg/mL, 1.125 mg/mL, and 200 mg/mL, respectively. The mixture was cooled to ice temperature to give a hydrogel formulation, cocktail vaccine j. The amount of the preparation was adjusted as appropriate.

Cocktail vaccine j was injected to mice intradermally at the tail base area in an amount for administering 300 μg of Compound of formula 4 per body and 225 μg of Peptide SEQ ID No. 3 per body. Or, in the step of preparing cocktail vaccine j, the compound prepared in Example 1 was added to the pH 2.5 buffer to prepare a vaccine, and the prepared vaccine was injected to mice intradermally at the tail base area in an amount for administering 300 μg of Compound of formula 4 per body, 225 μg of Peptide SEQ ID No. 3 per body, and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 17:
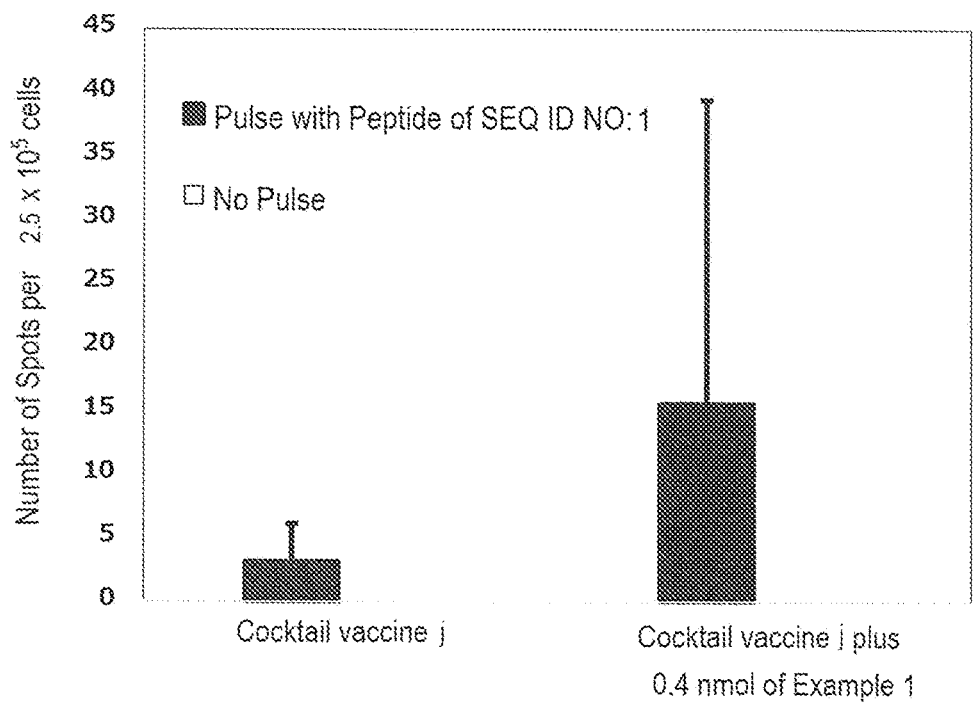
FIG. 17 shows the results of Test 15, i.e., a vaccine was prepared by adding the compound prepared in Example 1 to a cocktail vaccine (hydrogel formulation) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 17.
Figure 18:
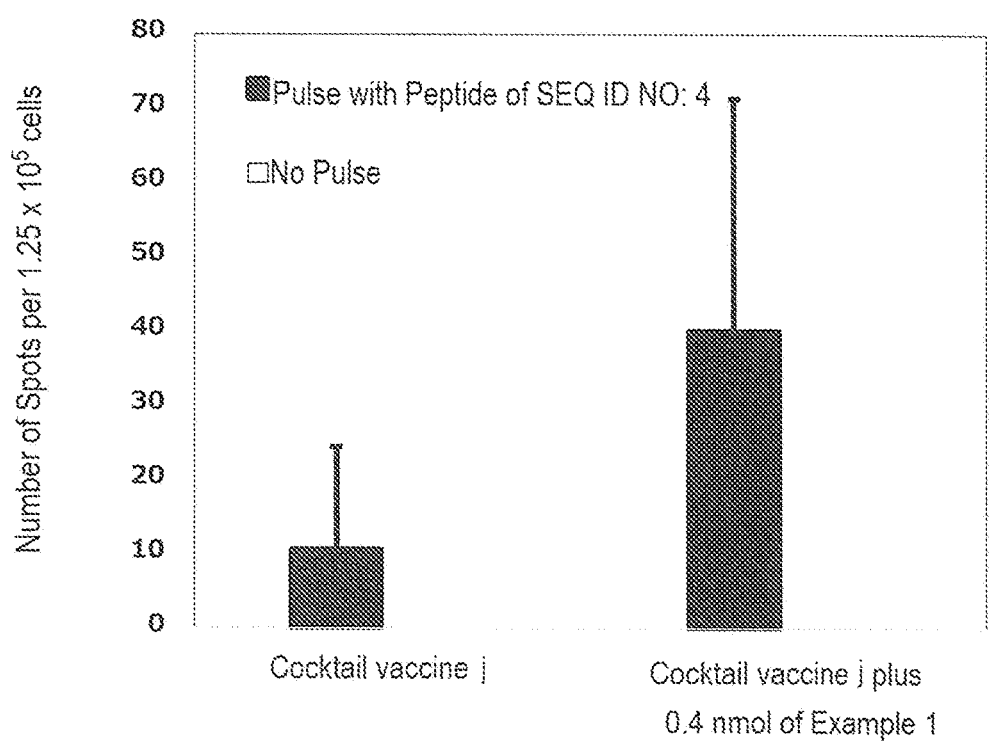
FIG. 18 shows the results of Test 15, i.e., a vaccine was prepared by adding the compound prepared in Example 1 to a cocktail vaccine (hydrogel formulation) comprising Compound of formula 4 and Peptide SEQ ID No. 3; and the vaccine was tested about in vivo CTL induction for SEQ ID No. 4 with a HLA-A*02:01 transgenic mouse by IFNγ ELISPOT assay. The results are shown in FIG. 18.

The results were shown in FIG. 17 and FIG. 18. The results of the present test showed that the CTL counts responsive to Peptide SEQ ID No. 1 or SEQ ID No. 4 were more in the case of adding the compound prepared in Example 1 to cocktail vaccine j, compared with the case of adding no compound.

The above results show that the induced CTL count increases by adding the compound prepared in Example 1 to the vaccine, and strongly suggest that the compound prepared in Example 1 has in vivo adjuvant activity.

Figure 27:
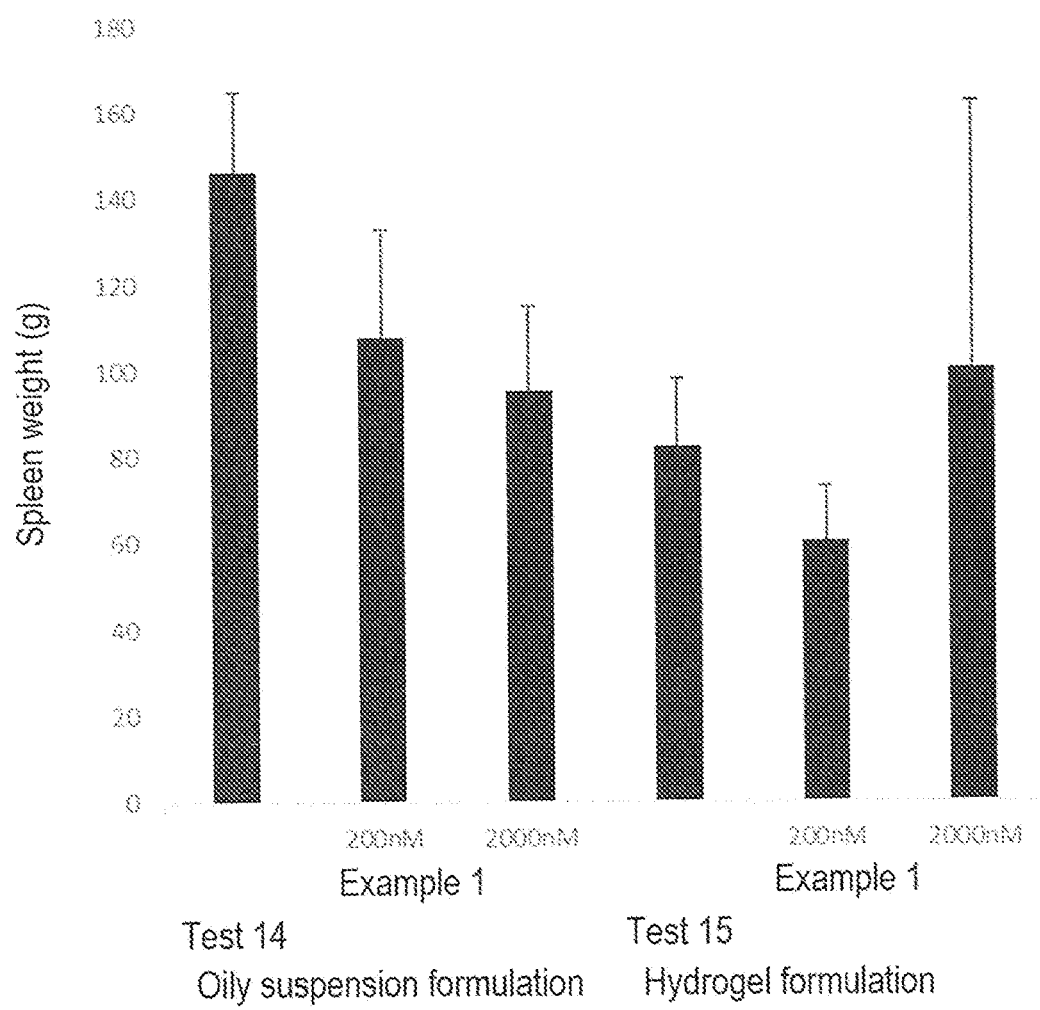
FIG. 27 shows the results of Tests 14 and 15, i.e., a composition comprising Compound of formula 4 and Peptide SEQ ID No. 3 was oil-based-suspended or hydrogel-formulated to prepare each cocktail vaccine; the compound prepared in Example 1 was added to the cocktail vaccine to prepare each vaccine; the vaccine was administered to the mouse; and the mouse's spleen was weighed. The results are shown in FIG. 27.

FIG. 27 shows the results of each spleen weight in the mice tested in Tests 14 and 15. The present results show that the administration of Example 1 does not induce a pronounced increase of spleen weight, and suggest that the compound prepared in Example 1 has in vivo adjuvant activity without causing splenomegaly.

Test 16
Evaluation of In Vivo Adjuvant Activity in HLA-A*02:01 Transgenic Mouse

The in vivo adjuvant activity of the compound of Example 1 was evaluated in the following procedure. To a vaccine (liposome formulation 1) comprising Compound of formula 4 prepared in Reference example 8 and Peptide SEQ ID No. 3 prepared in Reference example 3 (hereinafter, referred to as "cocktail vaccine k") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above liposome formulation 1 was prepared as follows. 47.1 mg of hydrogenated soybean phosphatidylcholine and 15.47 mg of cholesterol were dissolved in t-butyl alcohol, and the mixture was lyophilized. To the lyophilized product was added 2 mL of pH 2.5 buffer (10 mM tartaric acid, 10% trehalose) containing 2.5 mg/mL of Compound of formula 4 and 1.875 mg/mL of Peptide SEQ ID No. 3, and the solution was filtered through 0.1 μm polycarbonate membrane filter with an extruder (Mini-Extruder, Avanti Polar Lipids) which was warmed at about 65° C. to give liposome formulation 1, cocktail vaccine k. The amount of the preparation was adjusted as appropriate.

Cocktail vaccine k was injected to mice intradermally at the tail base area in an amount for administering 500 μg of Compound of formula 4 per body and 375 μg of Peptide SEQ ID No. 3 per body. Or, in the step of preparing cocktail vaccine k, the compound prepared in Example 1 was added to the pH 2.5 buffer to prepare a vaccine, and the prepared vaccine was injected to mice intradermally at the tail base area in an amount for administering 500 μg of Compound of formula 4 per body, 375 μg of Peptide SEQ ID No. 3 per body, and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 19:
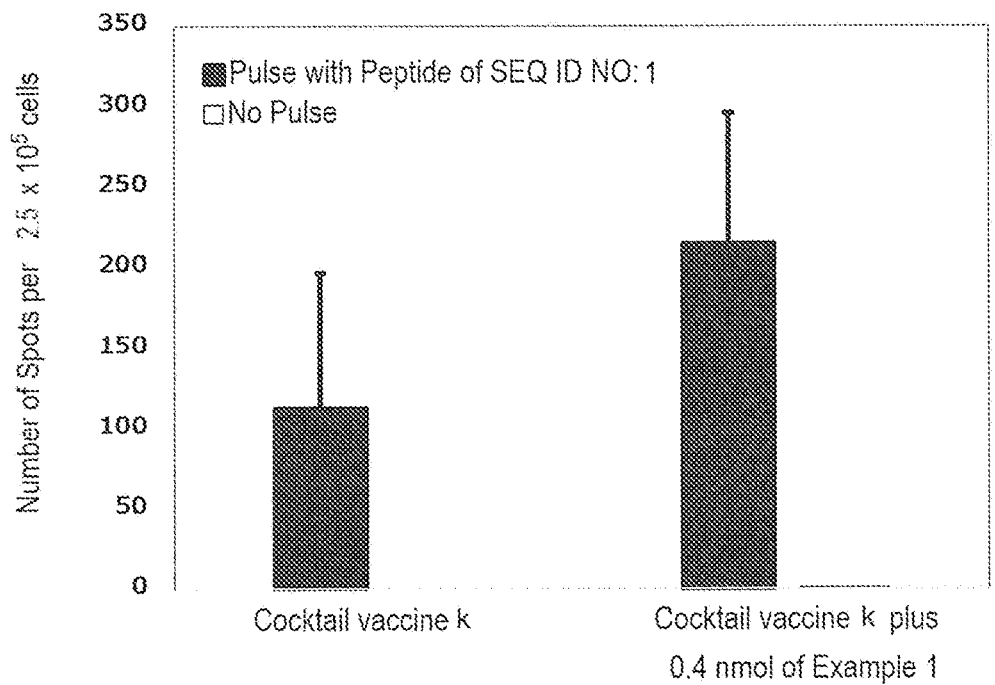
FIG. 19 shows the results of Test 16, i.e., a vaccine was prepared by adding the compound prepared in Example 1 to a cocktail vaccine (liposome formulation 1) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 19.

The result was shown in FIG. 19. The results of the present test showed that the CTL counts responsive to Peptide SEQ ID No. 1 were more in the case of adding the compound prepared in Example 1 to cocktail vaccine k, compared with the case of adding no compound.

The above results show that the induced CTL count increases by adding the compound prepared in Example 1 to the vaccine, and strongly suggest that the compound prepared in Example 1 has in vivo adjuvant activity.

Test 17
Evaluation of In Vivo Adjuvant Activity in HLA-A*02:01 Transgenic Mouse

The in vivo adjuvant activity of the compound of Example 1 was evaluated in the following procedure.

To a vaccine (liposome formulation 2) comprising Compound of formula 4 prepared in Reference example 8 and Peptide SEQ ID No. 3 prepared in Reference example 3 (hereinafter, referred to as "cocktail vaccine 1") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above liposome formulation 2 was prepared as follows. 42.66 mg of sphingomyelin and 15.47 mg of cholesterol were dissolved in t-butyl alcohol, and the mixture was lyophilized. To the lyophilized product was added 2 mL of pH 2.5 buffer (10 mM tartaric acid, 10% trehalose) containing 2.5 mg/mL of Compound of formula 4 and 1.875 mg/mL of Peptide SEQ ID No. 3, and the solution was filtered through 0.1 μm polycarbonate membrane filter with an extruder (Mini-Extruder, Avanti Polar Lipids) which was warmed at about 65° C. to give liposome formulation 2, cocktail vaccine 1. The amount of the preparation was adjusted as appropriate.

Cocktail vaccine 1 was injected to mice intradermally at the tail base area in an amount for administering 500 μg of Compound of formula 4 per body and 375 μg of Peptide SEQ ID No. 3 per body. Or, in the step of preparing cocktail vaccine 1, the compound prepared in Example 1 was added to the pH 2.5 buffer to prepare a vaccine, and the prepared vaccine was injected to mice intradermally at the tail base area in an amount for administering 500 μg of Compound of formula 4 per body, 375 μg of Peptide SEQ ID No. 3 per body, and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 4) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 20:
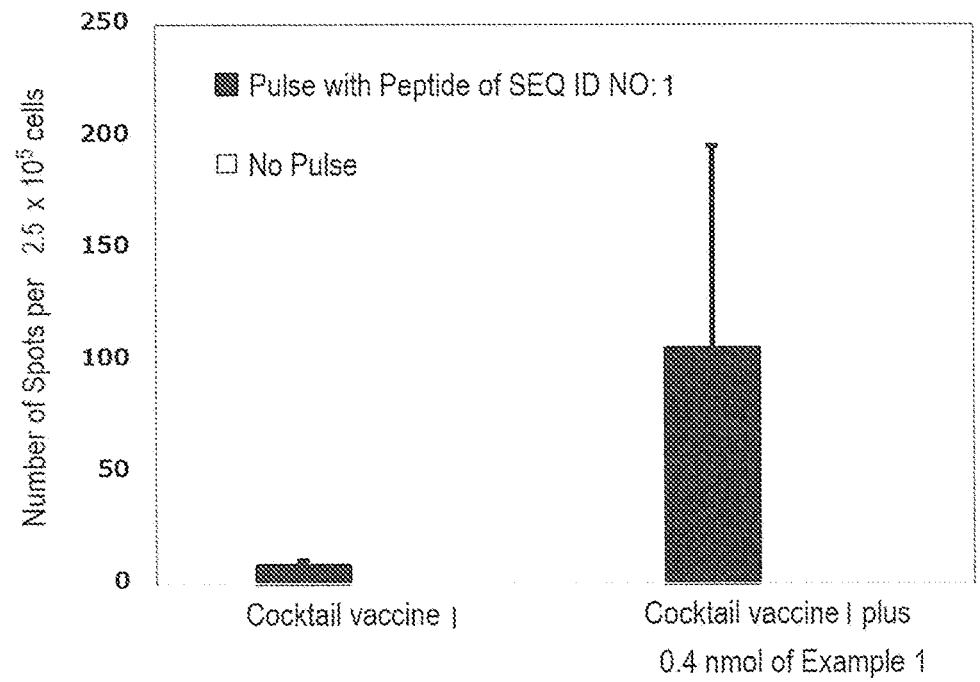
FIG. 20 shows the results of Test 17, i.e., a vaccine was prepared by adding the compound prepared in Example 1 to a cocktail vaccine (liposome formulation 2) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 20.
Figure 21:
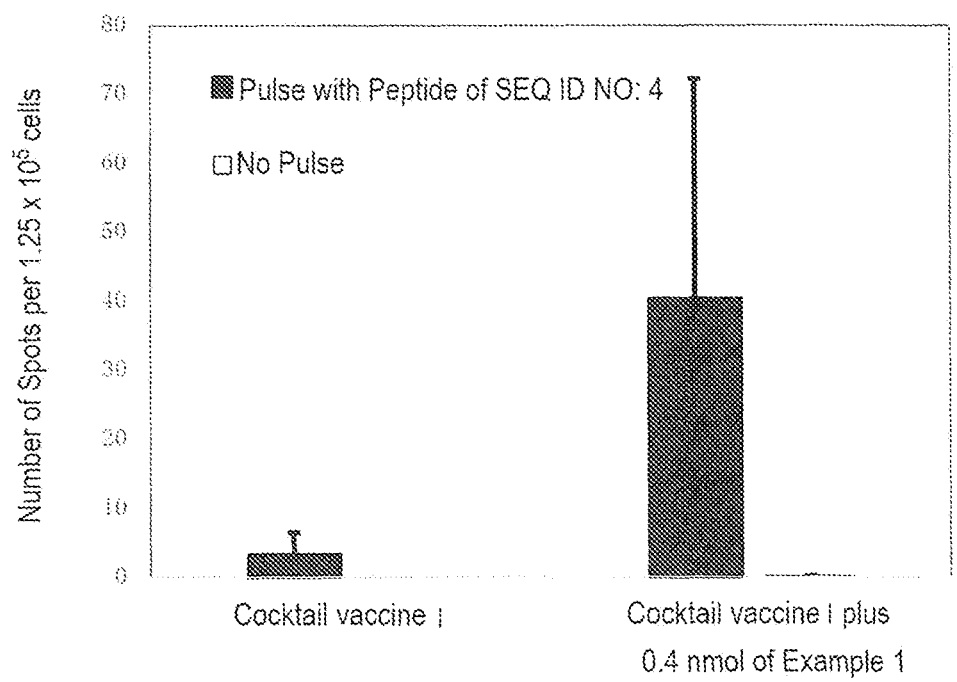
FIG. 21 shows the results of Test 17, i.e., a vaccine was prepared by adding the compound prepared in Example 1 to a cocktail vaccine (liposome formulation 2) comprising Compound of formula 4 and Peptide SEQ ID No. 3; and the vaccine was tested about in vivo CTL induction for SEQ ID No. 4 with a HLA-A*02:01 transgenic mouse by IFNγ ELISPOT assay. The results are shown in FIG. 21.

The results were shown in FIG. 20 and FIG. 21. The results of the present test showed that the CTL counts responsive to Peptide SEQ ID No. 1 or SEQ ID No. 4 were more in the case of adding the compound prepared in Example 1 to cocktail vaccine 1, compared with the case of adding no compound.

The above results show that the induced CTL count increases by adding the compound prepared in Example 1 to the vaccine, and strongly suggest that the compound prepared in Example 1 has in vivo adjuvant activity.

Test 18
Evaluation of In Vivo Adjuvant Activity in HLA-A*02:01 Transgenic Mouse

The in vivo adjuvant activity of the compound of Example 1 was evaluated in the following procedure. To a vaccine (liposome formulation 3) comprising Compound of formula 4 prepared in Reference example 8 and Peptide SEQ ID No. 3 prepared in Reference example 3 (hereinafter, referred to as "cocktail vaccine m") was added the compound prepared in Example 1 to prepare a vaccine. The vaccine was administered to a HLA-A*02:01 transgenic mouse, and the adjuvant activity of the vaccine was evaluated by the method of testing antigen-specific CTL induction.

For example, the above liposome formulation 3 was prepared as follows. 36.7 mg of 1,2-dipalmitoyl-sn-glycero-3-phosphocholine, 7.58 mg of 1,2-dipalmitoyl-sn-glycero-3-phospho-L-serine sodium salt, and 15.47 mg of cholesterol were dissolved in t-butyl alcohol/water mixture, and the mixture was lyophilized. To the lyophilized product was added 2 mL of pH 2.5 buffer (10 mM tartaric acid, 10% trehalose) containing 2.5 mg/mL of Compound of formula 4 and 1.875 mg/mL of Peptide SEQ ID No. 3, and the solution was filtered through 0.1 μm polycarbonate membrane filter with an extruder (Mini-Extruder, Avanti Polar Lipids) which was warmed at about 65° C. to give liposome formulation 3, cocktail vaccine m. The amount of the preparation was adjusted as appropriate.

Cocktail vaccine m was injected to mice intradermally at the tail base area in an amount for administering 500 μg of Compound of formula 4 per body and 375 μg of Peptide SEQ ID No. 3 per body. Or, in the step of preparing cocktail vaccine m, the compound prepared in Example 1 was added to the pH 2.5 buffer to prepare a vaccine, and the prepared vaccine was injected to mice intradermally at the tail base area in an amount for administering 500 μg of Compound of formula 4 per body, 375 μg of Peptide SEQ ID No. 3 per body, and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1) was added to the splenocyte-containing ELISPOT plate at a final concentration of 10 μg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 22:
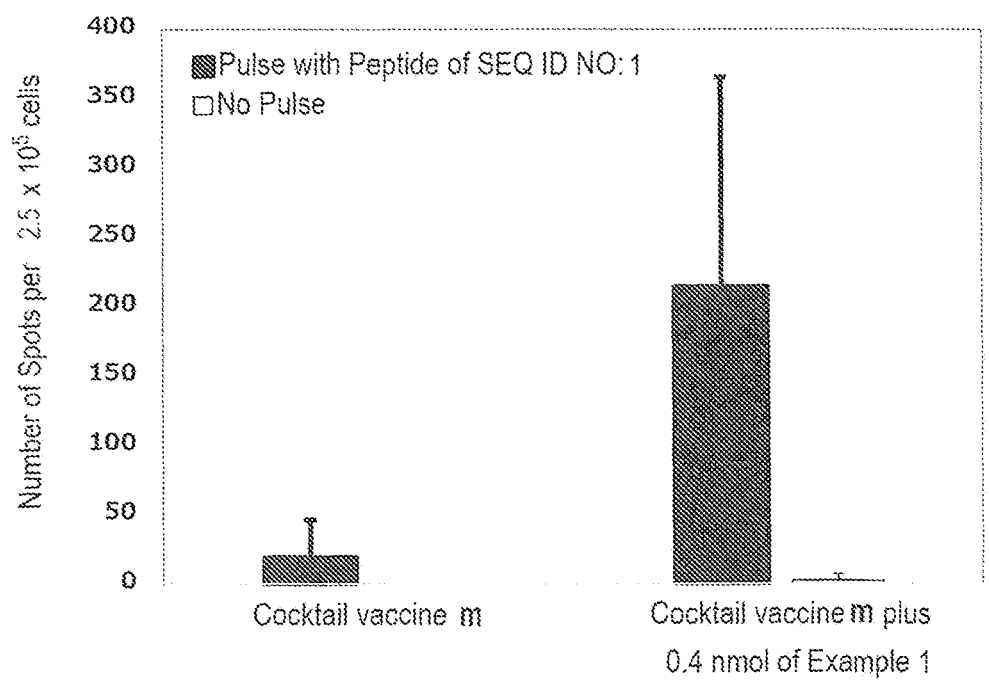
FIG. 22 shows the results of Test 18, i.e., a vaccine was prepared by adding the compound prepared in Example 1 to a cocktail vaccine (liposome formulation 3) comprising Compound of formula 4 and Peptide SEQ ID No. 3; and the vaccine was tested about in vivo CTL induction for SEQ ID No. 1 with a HLA-A*02:01 transgenic mouse by IFNγ ELISPOT assay. The results are shown in FIG. 22.

The result was shown in FIG. 22. The results of the present test showed that the CTL counts responsive to Peptide SEQ ID No. 1 were more in the case of adding the compound prepared in Example 1 to cocktail vaccine m, compared with the case of adding no compound.

The above results show that the induced CTL count increases by adding the compound prepared in Example 1 to the vaccine, and strongly suggest that the compound prepared in Example 1 has in vivo adjuvant activity.

Figure 28:
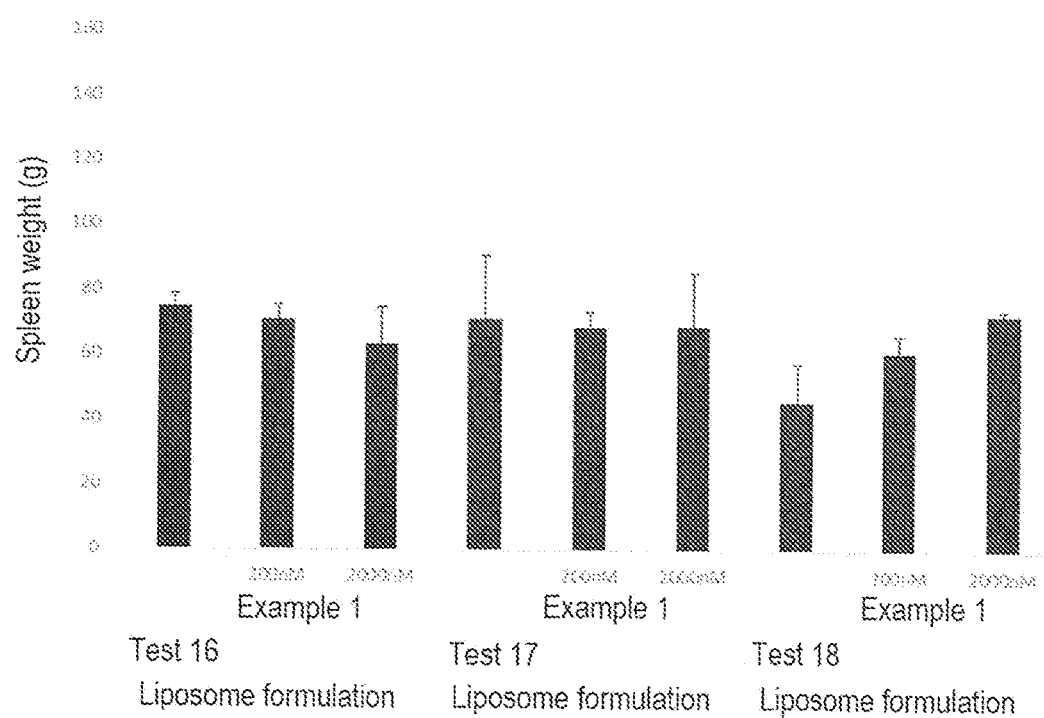
FIG. 28 shows the results of Tests 16-18, i.e., a composition comprising Compound of formula 4 and Peptide SEQ ID No. 3 was liposome-formulated to prepare a cocktail vaccine; the compound prepared in Example 1 was added to the cocktail vaccine to prepare a vaccine; the vaccine was administered to the mouse; and the mouse's spleen was weighed. The results are shown in FIG. 28.

FIG. 28 shows the results of each spleen weight in the mice tested in Tests 16-18. The present results show that the administration of Example 1 does not induce a pronounced increase of spleen weight, and suggest that the compound prepared in Example 1 has in vivo adjuvant activity without causing splenomegaly.

Test 19
Evaluation of In Vivo Adjuvant Activity in HLA-A*02:01/HLA-DRB1*01:01 Transgenic Mouse The in vivo adjuvant activity of the compound of Example 1 was evaluated in the following procedure. To a cocktail vaccine comprising Peptide SEQ ID No. 1 prepared in Reference example 1 and Peptide SEQ ID No. 17 prepared in Reference example 20 with a preliminarily-emulsified composition (hereinafter, referred to as "cocktail vaccine n") was added the compound prepared in Example 1 to prepare each vaccine. The vaccine was administered to a HLA-A*02:01/HLA-DRB1*01:01 transgenic mouse (C57BL/6CrHLA-A2.1DR1), and the adjuvant activity of each vaccine was evaluated by the method of testing antigen-specific CTL and antigen-specific helper T-cell induction. Peptide SEQ ID No. 17 is a helper peptide derived from WT1 protein.

Specifically, Peptide SEQ ID No. 1 and Peptide SEQ ID No. 17 were dissolved in DMSO, and then diluted with water for injection to concentrations of Peptide SEQ ID No. 1 of 2 mg/mL and Peptide SEQ ID No. 17 of 4 mg/mL. The prepared peptide dilution was mixed with an equal volume of the preliminary emulsified composition prepared like Test 4 to give an emulsified product, cocktail vaccine n. Cocktail vaccine n was injected to mice intradermally at the tail base area in an amount for administering 200 µg of Peptide SEQ ID No. 1 per body and 400 µg of Peptide SEQ ID No. 17 per body. Or, in the step of preparing cocktail vaccine n, the compound prepared in Example 1 was added to the diluted peptide solution to prepare a vaccine, and the prepared vaccine was injected to mice intradermally at the tail base area in an amount for administering 200 µg of Peptide SEQ ID No. 1 per body, 400 µg of Peptide SEQ ID No. 17 per body, and 0.04 nmol or 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 4, Peptide (SEQ ID No. 1 or SEQ ID No. 17) was added to the splenocyte-containing ELISPOT plate at a final concentration of 10 µg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 23:
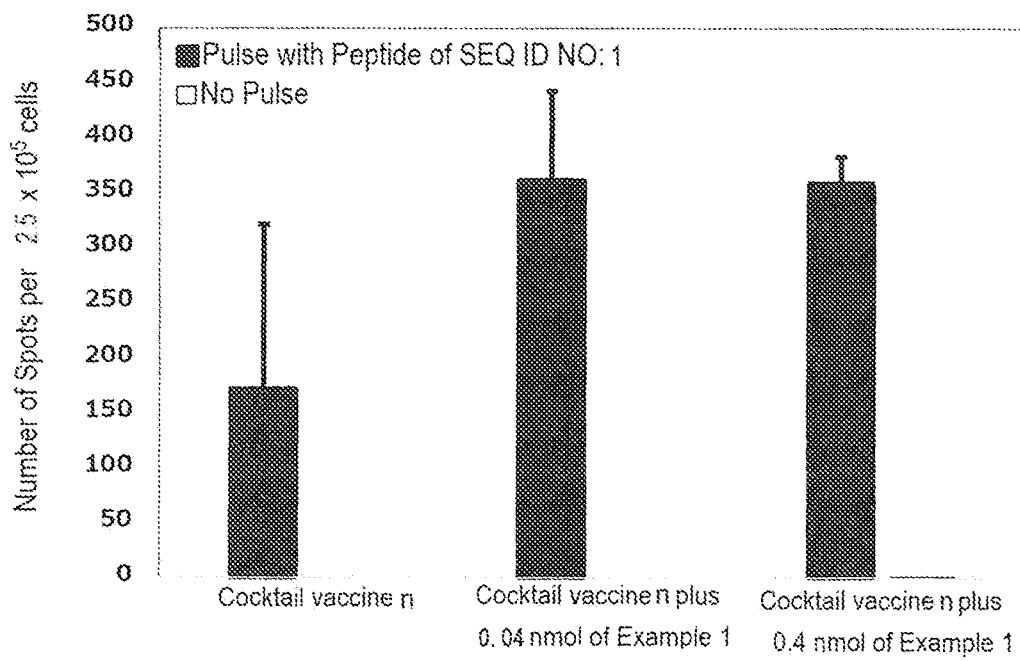
FIG. 23 shows the results of Test 19, i.e., a vaccine was prepared by adding the compound prepared in Example 1 to a cocktail vaccine comprising Peptide SEQ ID No. 1 and Peptide SEQ ID No. 17 with a preliminary emulsified composition; and the vaccine was tested about in vivo CTL induction for SEQ ID No. 1 with a HLA-A*02:01/HLA-DRB1*01:01 transgenic mouse by IFNγ ELISPOT assay. The results are shown in FIG. 23.
Figure 24:
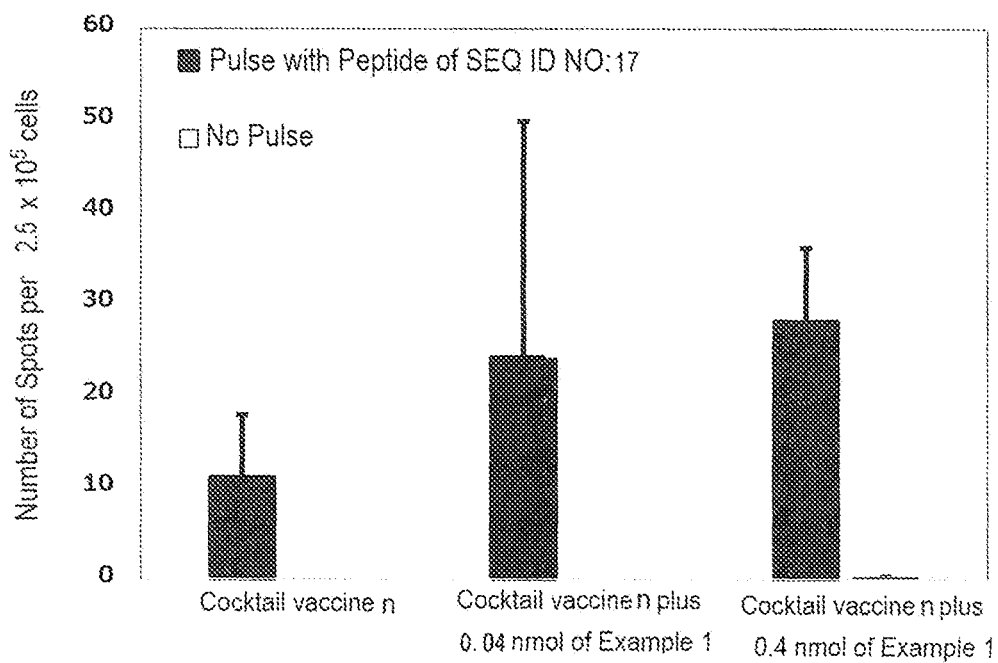
FIG. 24 shows the results of Test 19, i.e., a vaccine was prepared by adding the compound prepared in Example 1 to a cocktail vaccine comprising Peptide SEQ ID No. 1 and Peptide SEQ ID No. 17 with a preliminary emulsified composition; and the vaccine was tested about in vivo helper T-cell induction for SEQ ID No. 17 with a HLA-A*02:01/HLA-DRB1*01:01 transgenic mouse by IFNγ ELISPOT assay. The results are shown in FIG. 24.

The results were shown in FIG. 23 and FIG. 24. The results of the present test showed that the CTL counts responsive to Peptide SEQ ID No. 1 were more in the case of adding the compound prepared in Example 1 to cocktail vaccine n, compared with the case of adding no compound.

In addition, the results showed that the helper T-cell counts responsive to Peptide SEQ ID No. 17 were more in the case of adding the compound prepared in Example 1 to cocktail vaccine n, compared with the case of adding no compound.

The above results show that the induced CTL count and helper T-cell count increase by adding the compound prepared in Example 1 to the vaccine, and strongly suggest that the compound prepared in Example 1 has in vivo adjuvant activity.

Test 20
Evaluation of In Vivo Adjuvant Activity in HLA-A*24:02 Transgenic Mouse

The in vivo adjuvant activity of the compound of Example 1 was evaluated in the following procedure. To a vaccine prepared by mixing Compound of formula 5 prepared in Reference example 22 with a preliminarily-emulsified composition (hereinafter, referred to as "vaccine o") was added the compound prepared in Example 1 to prepare a vaccine. The vaccine was administered to a HLA-A*24:02 transgenic mouse, and the adjuvant activity of the vaccine was evaluated by the method of testing antigen-specific CTL induction.

Specifically, Compound of formula 5 was dissolved in DMSO, and then diluted with water for injection to concentrations of Compound of formula 5 of 3 mg/mL. The prepared compound dilution was mixed with an equal volume of the preliminary emulsified composition prepared like Test 4 to give an emulsified product, vaccine o. Vaccine o was injected to mice intradermally at the tail base area in an amount for administering 300 µg of Compound of formula 5 per body. Or, in the step of preparing vaccine o, the compound prepared in Example 1 was added to the diluted compound solution to prepare a vaccine, and the prepared vaccine was injected to mice intradermally at the tail base area in an amount for administering 300 µg of Compound of formula 5 per body and 0.4 nmol of the compound prepared in Example 1 per body. The administrations were done twice, which had one week interval. One week after the final administration, the mice were sacrificed with $CO_2$ gas. Splenocytes were harvested from spleens removed from the mice. Like Test 3, Peptide (SEQ ID No. 2) was added to the splenocyte-containing ELISPOT plate at a final concentration of 10 µg/ml, and the plate was incubated overnight at 37° C. under an atmosphere of 5% $CO_2$ to re-stimulate the peptide in vitro. Then, after removal of the supernatant from the wells, stained spots on the ELISPOT plate were counted.

Figure 25:
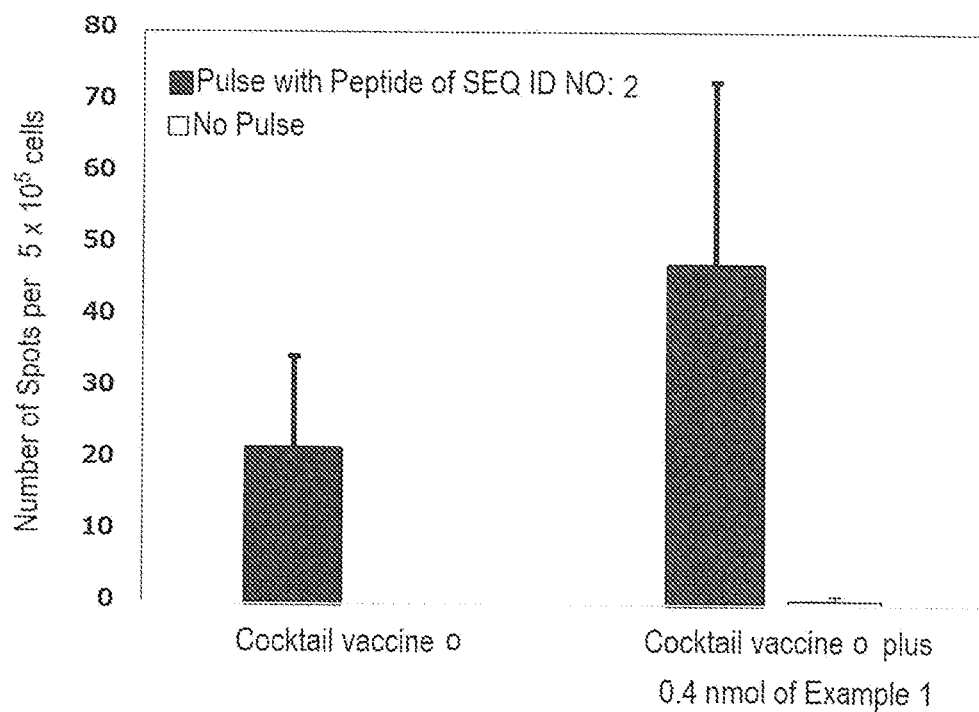
FIG. 25 shows the results of Test 20, i.e., a vaccine was prepared by adding the compound prepared in Example 1 to a vaccine comprising Compound of formula 5 and a preliminary emulsified composition; and the vaccine was tested about in vivo CTL induction for SEQ ID No. 2 with a HLA-A*24:02 transgenic mouse by IFNγ ELISPOT assay. The results are shown in FIG. 25.

The result was shown in FIG. 25. The results of the present test showed that the CTL counts responsive to Peptide SEQ ID No. 2 were more in the case of adding the compound prepared in Example 1 to vaccine o, compared with the case of adding no compound.

The above results show that the induced CTL count increases by adding the compound prepared in Example 1 to the vaccine, and strongly suggest that the compound prepared in Example 1 has in vivo adjuvant activity.

Test 21
According to the method of Test 1, human TLR7 reporter gene assay was done with the following samples, and the result was shown in the table below.

TABLE 9

| Example No. | human $EC_{50}$ (nM) |
|---|---|
| 3 | 637 |
| 11 | 774 |
| 8 | 388 |

TABLE 9-continued

| Example No. | human EC$_{50}$ (nM) |
|---|---|
| 9 | 3987 |
| 10 | 3807 |

The result of Test 21 suggests that the example compounds of the present invention can act as human TLR7 agonist.

Test 22

According to the method of Test 1, human TLR7 reporter gene assay was done with the following samples, and the result was shown in the table below. The cell used herein was HEK-Blue™ hTLR7 cell line (Invivogen). HEK-Blue™ hTLR7 cell line is a stably co-transfected cell line which expresses full-length human TLR7 and secretory SEAP reporter gene under the transcriptional regulation of an NF-κB response element. The TLR7 expression of the cell line has been already tested by RT-PCR. Transfectants with stable expression were selected using the antibiotic blasticidin and Zeocin.

TABLE 10

| Example No. | EC$_{50}$ (nM) |
|---|---|
| 5 | 7270 |
| 6 | 119 |
| 7 | 71 |

The invention claimed is:

1. A compound of formula (1):

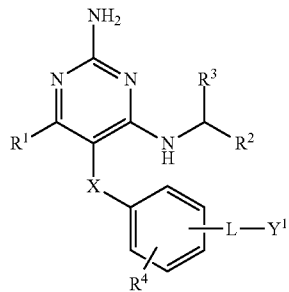

or a pharmaceutically acceptable salt thereof, wherein

X is methylene, oxygen atom, sulfur atom, SO, $SO_2$, or $NR^5$, wherein $R^5$ is hydrogen or $C_{1-6}$ alkyl, $R^1$ is $C_{1-6}$ alkyl which is optionally substituted with 1-5 substituents selected independently from the group consisting of halogen, hydroxy, and $C_{1-6}$ alkoxy, $R^2$ and $R^3$ are independently hydrogen or $C_{1-6}$ alkyl which is optionally substituted with 1-5 substituents selected independently from the group consisting of halogen, hydroxy, and $C_{1-6}$ alkoxy, $R^4$ is hydrogen, halogen, hydroxy, $C_{1-6}$ alkyl, which is optionally substituted with 1-3 the same or different halogens, $C_{1-6}$ alkoxy, which is optionally substituted with 1-3 the same or different halogens, or cyano, L is a linker, and $Y^1$ is $-(CH_2CH_2O)_m-R^6$, wherein $R^6$ is hydrogen or $C_{1-6}$ alkyl, and m is an integer from 3-100.

2. The compound of claim 1 or a pharmaceutically acceptable salt thereof, wherein X is methylene.

3. The compound of claim 1 or a pharmaceutically acceptable salt thereof, wherein $R^1$ is $C_{1-3}$ alkyl which is optionally substituted with 1-3 independently selected halogens.

4. The compound of claim 3 or a pharmaceutically acceptable salt thereof, wherein $R^1$ is methyl.

5. The compound of claim 1 or a pharmaceutically acceptable salt thereof, wherein $R^4$ is hydrogen, hydroxy, $C_{1-3}$ alkyl, or $C_{1-3}$ alkoxy.

6. The compound of claim 5 or a pharmaceutically acceptable salt thereof, wherein $R^4$ is hydrogen, hydroxy, or methoxy.

7. The compound of claim 1 or a pharmaceutically acceptable salt thereof, wherein $R^2$ is $C_{1-6}$ alkyl.

8. The compound of claim 1 or a pharmaceutically acceptable salt thereof, wherein $R^3$ is hydrogen, or $C_{1-3}$ alkyl which is optionally substituted with 1-3 hydroxy.

9. The compound of claim 1 or a pharmaceutically acceptable salt thereof, wherein
L is a linker selected from —O—, —$NR^Y$—, —C(O)—, —C(O)O—, —OC(O)—, —C(O) $NR^Y$—, —$NR^YC(O)$—, —$CH_2NR^Y$—, —$CH_2O$—, —OC(O)O—, —$NR^7C(O)O$—, —$OC(O)NR^Y$—, —$NR^7C(O)NR^Y$—, —$OC(S)NR^Y$—, and —$NR^7C(S)NR^Y$—; wherein $R^7$ is hydrogen or $C_{1-6}$ alkyl; and $R^Y$ is hydrogen, $C_{1-6}$ alkyl, or $Y^2$; wherein $Y^2$ is —$(CH_2CH_2O)_n$—$R^8$; and wherein $R^8$ is hydrogen atom or $C_{1-6}$ alkyl, and n is an integer from 3-100.

10. The compound of claim 9 or a pharmaceutically acceptable salt thereof, wherein L is —$C(O)NR^Y$—, —$CH_2NR^Y$—, —C(O)O—, or —$CH_2O$—.

11. The compound of claim 9 or a pharmaceutically acceptable salt thereof, wherein
L is —$CH_2NR^Y$—, and
$R^Y$ is hydrogen, $C_{1-6}$ alkyl, or $Y^2$.

12. The compound of claim 1 or a pharmaceutically acceptable salt thereof, wherein
$Y^1$ is —$(CH_2CH_2O)_m$—$R^6$,
$R^6$ is hydrogen or $C_{1-6}$ alkyl, and
m is an integer from 3-40.

13. The compound of claim 1 or a pharmaceutically acceptable salt thereof, wherein the compound is a compound of formula (2):

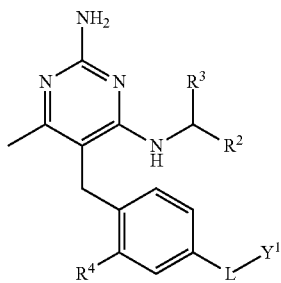

(2)

or formula (3):

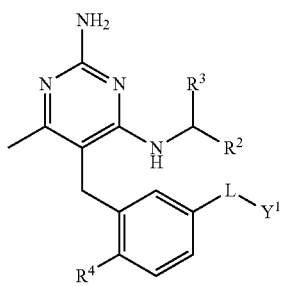

(3)

wherein
$R^2$ is $C_{1-6}$ alkyl,
$R^3$ is hydrogen or $C_{1-3}$ alkyl, which is optionally substituted with 1-3 hydroxy,
$R^4$ is hydrogen, hydroxy, or methoxy,
L is —$CH_2NR^Y$—,
$R^Y$ is hydrogen or $C_{1-6}$ alkyl,
$Y^1$ is —$(CH_2CH_2O)_m$—$R^6$,
$R^6$ is hydrogen or $C_{1-6}$ alkyl, and
m is an integer from 3-20.

14. The compound of claim 1 or a pharmaceutically acceptable salt thereof, wherein the compound is a compound of formula (2):

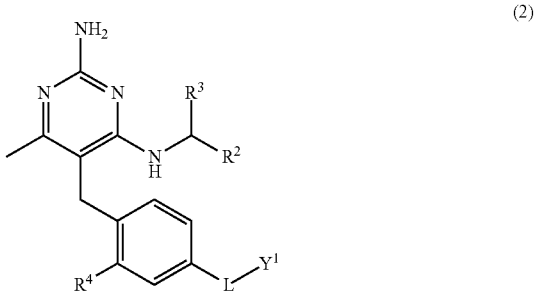

(2)

wherein
$R^2$ is $C_{1-6}$ alkyl,
$R^3$ is hydrogen or $C_{1-3}$ alkyl, which is optionally substituted with one hydroxy,
$R^4$ is hydrogen or methoxy,
L is —$CH_2NR^Y$—,
$R^Y$ is hydrogen or $C_{1-6}$ alkyl,
$Y^1$ is —$(CH_2CH_2O)_m$—$R^6$,
$R^6$ is hydrogen or $C_{1-6}$ alkyl, and
m is selected from 3-40.

15. The compound of claim 1 or a pharmaceutically acceptable salt thereof, which is selected from:
1-(4- {[2-amino-4-methyl-6-(pentylamino)pyrimidin-5-yl]methyl}-3-methoxyphenyl)-2-methyl-5,8, 11, 14-tetraoxa-2-azahexadecan-16-ol;
1-{4-[(2-amino-4- {[(3S)-1-hydroxyhexan-3-yl]amino}-6-methylpyrimidin-5-yl)methyl]-3-methoxyphenyl}-2-methyl-5,8,11,14-tetraoxa-2-azahexadecan-16-ol;
1-(3- {[2-amino-4-methyl-6-(pentylamino)pyrimidin-5-yl]methyl}-4-methoxyphenyl)-2-methyl-5,8, 11, 14-tetraoxa-2-azahexadecan-16-ol;
1-(3- {[2-amino-4-methyl-6-(pentylamino)pyrimidin-5-yl]methyl}-4-hydroxyphenyl)-2-methyl-5,8, 11, 14-tetraoxa-2-azahexadecan-16-ol;
4-[(2-amino-4- {[(2S)-1-hydroxypentan-2-yl]amino}-6-methylpyrimidin-5-yl)methyl]-N-(20-hydroxy-3,6,9, 12,15, 18-hexaoxaicosan-1-yl)-3-methoxybenzamide;
2,5,8, 11-tetraoxatridecan-13-yl 4-[(2-amino-4- {[(2S)-1-hydroxypentan-2-yl]amino}-6-methylpyrimidin-5-yl) methyl]-3-methoxybenzoate;
5- {[2-methoxy-4-(2,5,8,11,14-pentaoxapentadecan-1-yl) phenyl]methyl}-6-methyl-N4-pentylpyrimidine-2,4-diamine;
1-(4- {[2-amino-4-methyl-6-(pentylamino)pyrimidin-5-yl]methyl}-3-methoxyphenyl)-2-methyl-5,8, 11, 14, 17,20,23,26,29-nonaoxa-2-azahentriacontan-31-ol;
1-(4- {[2-amino-4-methyl-6-(pentylamino)pyrimidin-5-yl]methyl}-3-methoxyphenyl)-2-methyl-5,8,11,14,17, 20,23,26,29,32,35,38,41,44,47,50,53,56,59,62,65,68, 71-tricosaoxa-2-azatriheptacontan-73-ol;
1-(4- {[2-amino-4-methyl-6-(pentylamino)pyrimidin-5-yl]methyl}-3-methoxyphenyl)-2-methyl- 5,8,11,14,17,20,23,26,29,32,35,38,41,44,47,50,53,56,59,62, 65,68,71,74,77,80,83,86,89,92,95,98, 101,104, 107-pentatriacontaoxa-2-azanonahectan-109-ol; and 12-[(4- {[2-amino-4-methyl-6-(pentylamino)pyrimidin-5-yl]methyl}-3-methoxyphenyl)methyl]-3,6,9,15,18, 21-hexaoxa-12-azatricosan-1,23-diol.

16. The compound of claim 1 or a pharmaceutically acceptable salt thereof, which is selected from:

1-(4- {[2-amino-4-methyl-6-(pentylamino)pyrimidin-5-yl]methyl}-3-methoxyphenyl)-2-methyl-5,8, 11, 14-tetraoxa-2-azahexadecan-16-ol;

1-(4- {[2-amino-4-methyl-6-(pentylamino)pyrimidin-5-yl]methyl}-3-methoxyphenyl)-2-methyl-5,8,11, 14,17, 20,23,26,29-nonaoxa-2-azahentriacontan-31-ol;

1-(4- {[2-amino-4-methyl-6-(pentylamino)pyrimidin-5-yl]methyl}-3-methoxyphenyl)-2-methyl-5,8,11,14,17, 20,23,26,29,32,35,38,41,44,47,50,53,56,59,62,65,68, 71-tricosaoxa-2-azatriheptacontan-73-ol;

1-(4- {[2-amino-4-methyl-6-(pentylamino)pyrimidin-5-yl]methyl}-3-methoxyphenyl)-2-methyl-5,8,11,14,17, 20,23,26,29,32,35,38,41,44,47,50,53,56,59,62,65,68, 71,74,77,80,83,86,89,92,95,98, 101,104, 107-pentatriacontaoxa-2-azanonahectan-109-ol; and 12-[(4- {[2-amino-4-methyl-6-(pentylamino)pyrimidin-5-yl]methyl}-3-methoxyphenyl)methyl]-3,6,9,15,18, 21-hexaoxa-12-azatricosan-1,23-diol.

17. A pharmaceutical composition comprising the compound of claim 1, or a pharmaceutically acceptable salt thereof, and a pharmaceutically acceptable diluent or carrier.

18. The pharmaceutical composition of claim 17, which is an emulsion formulation, an oil-based suspension, a hydrogel formulation, or a lipid formulation.

19. The pharmaceutical composition of claim 18, which is an emulsion formulation.

20. The pharmaceutical composition of claim 19, wherein the emulsion formulation is a water-in-oil emulsion.

21. The pharmaceutical composition of claim 20, wherein the emulsion formulation comprises (1) ethyl oleate, octyldodecyl myristate, sorbitan monooleate, glyceryl monooleate, polyoxyethylene hydrogenated castor oil 20, glycerin, and sodium dihydrogen phosphate; or (2) Montanide ISA 51VG.

22. The pharmaceutical composition of claim 18, which is a lipid formulation.

23. The pharmaceutical composition of claim 22, wherein the lipid formulation is a liposome formulation comprising phospholipid.

24. The pharmaceutical composition of claim 23, wherein the liposome formulation comprises at least one additive selected from the group consisting of inorganic acid, inorganic acid salt, organic acid, organic acid salt, sugars, buffering agent, antioxidant, and polymers.

25. The pharmaceutical composition of claim 22, wherein the lipid formulation is a liposome formulation comprising sterols.

26. The pharmaceutical composition of claim 25, wherein the sterols are cholesterol.

27. The pharmaceutical composition of claim 17, further comprising a tumor antigen.

28. The pharmaceutical composition of claim 27, wherein the tumor antigen is a tumor antigen peptide.

29. The pharmaceutical composition of claim 28, wherein the tumor antigen peptide is a combination of a peptide represented by the amino acid sequence of formula (4):

CRMFPNAPYL (SEQ ID NO: 19)
|
CYTWNQMNL (SEQ ID NO: 2)

wherein the bond between C—C is a disulfide bond, or a pharmaceutically acceptable salt thereof, and
a peptide represented by the amino acid sequence of SEQ ID NO 3: WAPVLDFAPPGASAYGSL, or a pharmaceutically acceptable salt thereof.

30. A kit comprising
a) the pharmaceutical composition of claim 17; and
b) a tumor antigen or a pharmaceutical composition comprising a tumor antigen.

31. A kit comprising:
a) the pharmaceutical composition of claim 17; and
b) an antigen or a pharmaceutical composition comprising an antigen.

32. A kit comprising
a) the pharmaceutical composition of claim 17; and
b) a pathogen-derived antigen or a pharmaceutical composition comprising a pathogen-derived antigen.

33. A kit comprising
a) the compound of claim 1 or a pharmaceutically acceptable salt thereof; and
b) a tumor antigen or a pharmaceutical composition comprising a tumor antigen.

34. A method of treating cancer comprising administering to a subject therapeutically effective amount of the compound of claim 1, or a pharmaceutically acceptable salt thereof.

35. A kit comprising
a) the compound of claim 1 or a pharmaceutically acceptable salt thereof, and
b) an antigen or a pharmaceutical composition comprising an antigen.

36. A kit comprising
a) the compound of claim 1 or a pharmaceutically acceptable salt thereof; and
b) a pathogen-derived antigen or a pharmaceutical composition comprising a pathogen-derived antigen.

37. A method for inducing cytotoxic T-lymphocyte in a mammal, comprising administering the compound of claim 1, or a pharmaceutically acceptable salt thereof, to the mammal.

38. A method for enhancing the cytotoxic T-lymphocyte induction in a mammal, comprising administering the compound of claim 1, or a pharmaceutically acceptable salt thereof, to the mammal.

39. A method for enhancing specific immune response in a mammal to an antigen, comprising administering the compound of claim 1, or a pharmaceutically acceptable salt thereof, to the mammal.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<223> OTHER INFORMATION: Peptide

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide

<400> SEQUENCE: 2

Cys Tyr Thr Trp Asn Gln Met Asn Leu
1               5

<210> SEQ ID NO 3
<211> LENGTH: 18
<212> TYPE: PRT
<213> ORGANISM: Artificial Sequence
<220> FEATURE:
<223> OTHER INFORMATION: Peptide

<400> SEQUENCE: 3

Trp Ala Pro Val Leu Asp Phe Ala Pro Pro Gly Ala Ser Ala Tyr Gly
1               5                   10                  15

Ser Leu

<210> SEQ ID NO 4
<211> LENGTH: 9
<212> TYPE: PRT
<213> ORGANISM: Artificial Sequence
<220> FEATURE:
<223> OTHER INFORMATION: Peptide

<400> SEQUENCE: 4

Val Leu Asp Phe Ala Pro Pro Gly Ala
1               5

<210> SEQ ID NO 5
<211> LENGTH: 9
```

```
<212> TYPE: PRT
<213> ORGANISM: Artificial Sequence
<220> FEATURE:
<223> OTHER INFORMATION: Peptide

<400> SEQUENCE: 5

Val Leu Gln Glu Leu Asn Val Thr Val
1               5

<210> SEQ ID NO 6
<211> LENGTH: 9
<212> TYPE: PRT
<213> ORGANISM: Artificial Sequence
<220> FEATURE:
<223> OTHER INFORMATION: Peptide

<400> SEQUENCE: 6

Gly Leu Tyr Asp Gly Met Glu His Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Peptide

<400> SEQUENCE: 7

Lys Ile Phe Gly Ser Leu Ala Phe Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Peptide

<400> SEQUENCE: 8

Ala Leu Leu Pro Ala Val Pro Ser Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Peptide

<400> SEQUENCE: 9

Ser Leu Gly Glu Gln Gln Tyr Ser Val
1               5

<210> SEQ ID NO 10
<211> LENGTH: 9
<212> TYPE: PRT
<213> ORGANISM: Artificial Sequence
<220> FEATURE:
<223> OTHER INFORMATION: Peptide

<400> SEQUENCE: 10

Arg Val Pro Gly Val Ala Pro Thr Leu
1               5

<210> SEQ ID NO 11
<211> LENGTH: 9
<212> TYPE: PRT
```

```
<213> ORGANISM: Artificial Sequence
<220> FEATURE:
<223> OTHER INFORMATION: Peptide

<400> SEQUENCE: 11

Cys Met Thr Trp Asn Gln Met Asn Leu
1               5

<210> SEQ ID NO 12
<211> LENGTH: 19
<212> TYPE: PRT
<213> ORGANISM: Artificial Sequence
<220> FEATURE:
<223> OTHER INFORMATION: Peptide

<400> SEQUENCE: 12

Cys Trp Ala Pro Val Leu Asp Phe Ala Pro Pro Gly Ala Ser Ala Tyr
1               5                   10                  15

Gly Ser Leu

<210> SEQ ID NO 13
<211> LENGTH: 19
<212> TYPE: PRT
<213> ORGANISM: Artificial Sequence
<220> FEATURE:
<223> OTHER INFORMATION: Peptide

<400> SEQUENCE: 13

Trp Ala Pro Val Leu Asp Phe Ala Pro Pro Gly Ala Ser Ala Tyr Gly
1               5                   10                  15

Ser Leu Cys

<210> SEQ ID NO 14
<211> LENGTH: 20
<212> TYPE: PRT
<213> ORGANISM: Artificial Sequence
<220> FEATURE:
<223> OTHER INFORMATION: Peptide

<400> SEQUENCE: 14

Cys Asn Lys Arg Tyr Phe Lys Leu Ser His Leu Gln Met His Ser Arg
1               5                   10                  15

Lys His Thr Gly
            20

<210> SEQ ID NO 15
<211> LENGTH: 18
<212> TYPE: PRT
<213> ORGANISM: Artificial Sequence
<220> FEATURE:
<223> OTHER INFORMATION: Peptide

<400> SEQUENCE: 15

Cys Asn Lys Arg Tyr Phe Lys Leu Ser His Leu Gln Met His Ser Arg
1               5                   10                  15

Lys His

<210> SEQ ID NO 16
<211> LENGTH: 17
<212> TYPE: PRT
<213> ORGANISM: Artificial Sequence
<220> FEATURE:
<223> OTHER INFORMATION: Peptide
```

```
<400> SEQUENCE: 16

Cys Asn Lys Arg Tyr Phe Lys Leu Ser His Leu Gln Met His Ser Arg
1               5                   10                  15

Lys

<210> SEQ ID NO 17
<211> LENGTH: 16
<212> TYPE: PRT
<213> ORGANISM: Artificial Sequence
<220> FEATURE:
<223> OTHER INFORMATION: Peptide

<400> SEQUENCE: 17

Lys Arg Tyr Phe Lys Leu Ser His Leu Gln Met His Ser Arg Lys His
1               5                   10                  15

<210> SEQ ID NO 18
<211> LENGTH: 10
<212> TYPE: PRT
<213> ORGANISM: Artificial Sequence
<220> FEATURE:
<223> OTHER INFORMATION: Peptide

<400> SEQUENCE: 18

Thr Tyr Ala Gly Cys Leu Ser Gln Ile Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Peptide

<400> SEQUENCE: 19

Cys Arg Met Phe Pro Asn Ala Pro Tyr Leu
1               5                   10
```